(12) United States Patent
Zhang et al.

(10) Patent No.: US 11,834,470 B2
(45) Date of Patent: Dec. 5, 2023

(54) 4-THIORIBOSE NAD ANALOGUES AND METHODS OF SYNTHESIZING AND USING THE SAME

(71) Applicant: University of Southern California, Los Angeles, CA (US)

(72) Inventors: Yong Zhang, Los Angeles, CA (US); Zhefu Dai, Los Angeles, CA (US); Xiao-Nan Zhang, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 239 days.

(21) Appl. No.: 17/281,424

(22) PCT Filed: Oct. 4, 2019

(86) PCT No.: PCT/US2019/054897
§ 371 (c)(1),
(2) Date: Mar. 30, 2021

(87) PCT Pub. No.: WO2020/073026
PCT Pub. Date: Apr. 9, 2020

(65) Prior Publication Data
US 2022/0227803 A1    Jul. 21, 2022

Related U.S. Application Data

(60) Provisional application No. 62/742,212, filed on Oct. 5, 2018.

(51) Int. Cl.
*A01N 43/04* (2006.01)
*A61K 31/70* (2006.01)
*C07H 19/20* (2006.01)
*A61K 31/7076* (2006.01)
*C12P 19/28* (2006.01)

(52) U.S. Cl.
CPC ......... *C07H 19/20* (2013.01); *A61K 31/7076* (2013.01); *C12P 19/28* (2013.01)

(58) Field of Classification Search
None
See application file for complete search history.

(56) References Cited

U.S. PATENT DOCUMENTS 9,926,340 B2    3/2018 Kraus et al.

FOREIGN PATENT DOCUMENTS

| CN | 102605026 A | 7/2012 |
| WO | WO-2018/227168 A1 | 12/2018 |

OTHER PUBLICATIONS

Dai et al., "Facile Chemoenzymatic Synthesis of a Novel Stable Mimic of NAD", Chemical Science, (2018), vol. 9, No. 44, pp. 8317-8464.
International Search Report and Written Opinion on International Patent Application No. PCT/US2019/054897 dated Dec. 19, 2019 (7 pages).

*Primary Examiner* — Patrick T Lewis
(74) *Attorney, Agent, or Firm* — Foley & Lardner LLP

(57) ABSTRACT

This disclosure provides a method of synthesis of 4'-thioribose NAD+ and analogues thereof, using an efficient chemoenzymatic approach. Also provided are methods of inhibiting the CD38 enzyme and compounds including 4'-thioribose NAD+ and compounds related thereto.

15 Claims, 33 Drawing Sheets

Specification includes a Sequence Listing.

4-THIORIBOSE NAD ANALOGUES AND METHODS OF SYNTHESIZING AND USING THE SAME

CROSS-REFERENCE TO RELATED APPLICATIONS

This application claims priority to International Patent Application No. PCT/US2019/054897, filed Oct. 4, 2019, which claims benefit under 35 U.S.C. § 119(e) to U.S. Provisional Application No. 62/742,212, filed Oct. 5, 2018, respectively, the contents of each of which are incorporated herein by reference in their entireties.

STATEMENT OF GOVERNMENT SUPPORT

This invention was made with a sponsor under the Grant No. 2P30DK048522, awarded by the National Institute for Health (NIH) and Grant No. V2016-021, awarded by the V Foundation for Cancer Research. The U.S. Government has certain rights to the invention.

SEQUENCE LISTING

The instant application contains a Sequence Listing which has been submitted electronically in ASCII format and is hereby incorporated by reference in its entirety. Said ASCII copy, created on Dec. 9, 2021, is named 064189-1261_SL.txt and is 8,684 bytes in size.

BACKGROUND

Nicotinamide adenine dinucleotide (NAD+) is an essential cofactor participating in a variety of important enzyme-mediated biological events, including electron transfer reactions, protein deacetylation, post-translational modification, and signaling transduction. Given the extensive involvements of NAD+-dependent enzymes in physiology and many human diseases, analogues of NAD+ have been generated to study and modulate chemical processes catalyzed by those enzymes.

SUMMARY

Applicant discloses herein the preparation of 4'-thioribose NAD+ using an easy and efficient chemoenzymatic approach. Substrate activities assays indicated the resulting 4'-thioribose NAD+ is chemically inert to human CD38 enzyme, but capable of participating in redox reactions in a manner similar to NAD+. X-ray crystallographic analysis revealed the binding of 4'-thioribose NAD+ to the active site of human CD38 and critical residues involved in leaving group activation and catalysis. By closely mimicking NAD+ in geometry and electrostatics, the generated 4'-thioribose NAD+ provide a unique and important tool that can be extended to study enzymes utilizing NAD+.

Thus in one aspect, provided herein are synthetic methods and novel intermediates for the synthesis of, e.g., a compound of formula I-A, I and VI.

In one aspect, a method of synthesizing a compound of formula I:

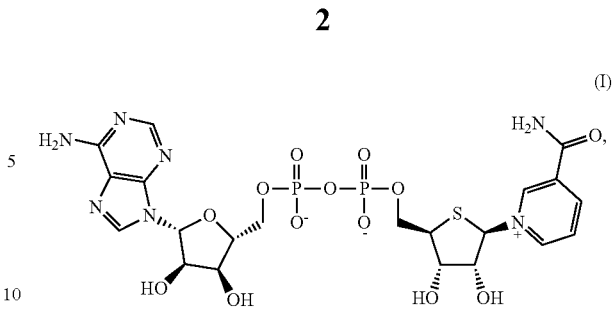

(I)

or a pharmaceutically acceptable salt or solvate thereof is provided, the method comprising, or consisting essentially of, or yet further consisting of, enzymatically converting a compound of formula IV:

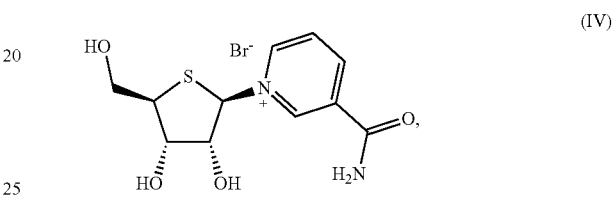

(IV)

to the compound of formula I.

Also provided herein are methods of synthesizing an analogue compound of formula VI:

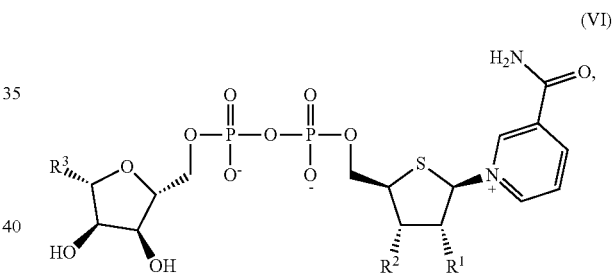

(VI)

or a pharmaceutically acceptable salt or solvate thereof, the method comprising, or consisting essentially of, or yet further consisting of, enzymatically converting a compound of formula VII:

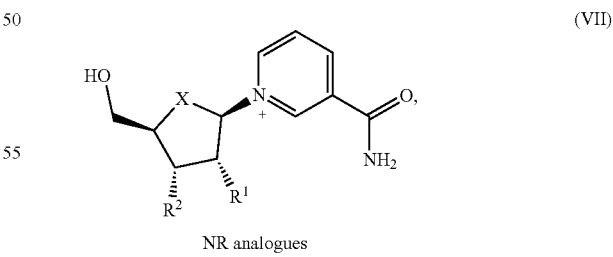

(VII)

NR analogues to the analogue compound of formula VI, wherein:
X is S or O;
$R^3$ is selected from thymine, cytosine, adenine, uracil or guanine; and
$R^1$ and $R^2$ are each independently selected from the group consisting of hydroxyl, thiol, optionally substituted $C_1$-$C_8$ alkyl, optionally substituted $C_1$-$C_8$ alkenyl, optionally substituted C₁-C₈ alkynyl, optionally substituted C₁-C₈ alkoxy, optionally substituted C₁-C₈ alkenyloxy, optionally substituted C₁-C₈ alkynyloxy, optionally substituted heteroaryloxy, optionally substituted aryloxy, acyl, acylamino, acyloxy, optionally substituted amino, halo, aminocarbonyl, aminothiocarbonyl, aminocarbonylamino, aminocarbonyloxy, aminosulfonyl, aminosulfonyloxy, aminosulfonylamino azidyl, cyano, nitro, oxo, amidino, arylthio, carboxylate, optionally substituted C₁-C₈ carboxyl ester, optionally substituted C₁-C₈ (carboxyl ester) amino, optionally substituted C₁-C₈ (carboxyl ester) oxy, optionally substituted C₁-C₈ cycloalkyl, optionally substituted heterocycloalkyl, optionally substituted C₁-C₈ cycloalkenyl, optionally substituted C₁-C₈ cycloalkoxy, optionally substituted C₁-C₈ cycloalkylthio, optionally substituted C₁-C₈ cycloalkenyloxy, optionally substituted C₁-C₈ heterocyclyloxy, and OP wherein P is a protecting group.

In one aspect, enzymatically converting the compound to the compound of an analogue formula I, the method comprises, or consists essentially of, or yet further consists of, contacting the compound of an analogue of formula IV with adenosine triphosphate (ATP), nicotinamide riboside kinase (NRK), and nicotinamide mononucleotide adenylyltransferase (NMNAT). In one aspect, the contacting is for less than 7 hours, or less than 6 hours, or less than 5 hours, or less than 4 hours, or less than 3 hours, or less than 2 hours, or less than 1 hour.

In one aspect, enzymatically converting the compound to the compound of an analogue formula VI, the method comprises, or consists essentially of, or yet further consists of, contacting the compound of an analogue of formula VII with adenosine triphosphate (ATP), nicotinamide riboside kinase (NRK), and nicotinamide mononucleotide adenylyltransferase (NMNAT). In one aspect, the contacting is for less than 7 hours, or less than 6 hours, or less than 5 hours, or less than 4 hours, or less than 3 hours, or less than 2 hours, or less than 1 hour.

The methods can be further modified by further comprising the step of converting a compound of formula II:

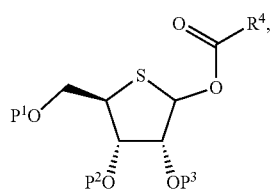

(II)

into a compound of formula III:

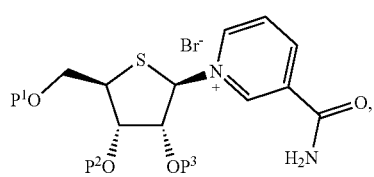

(III)

wherein R⁴ is an optionally substituted C₁-C₈ alkyl; P¹, P² and P³ are protecting groups each independently selected from 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), benzyloxymethyl acetal (BOM), methoxymethyl acetal (MOM), methoxypropyl acetal (MOP), methyl ether, tetrahydropyranyl acetal (THP), triethylsilyl ether (TES), triisopropylsilyl ether (TIPS), trimethylsilyl ether (TMS), tert-Butyldimethylsilyl ether (TBS, TBDMS), or tert-butyldiphenylsilyl ether (TBDPS); or P² and P³ together with the oxygens to which they are attached, together form an acetonide, benzaldehyde acetal or carbonate. In one aspect, R⁴ is methyl. In another embodiment, P¹ is Bz. In a yet further embodiment, P² and P³ along with the oxygens to which they are attached, together form an acetonide. In another aspect, the method further comprises, or consists essentially of, or yet further consists of the step of deprotecting the compound of formula III to produce the compound of formula IV. In one embodiment:

P¹ is Bz;

P² and P³ along with the oxygens to which they are attached, together form an acetonide; and wherein deprotecting the compound of formula III to produce the compound of formula IV comprises contacting the compound of formula III with trifluoroacetic acid (TFA) to produce a compound of formula V:

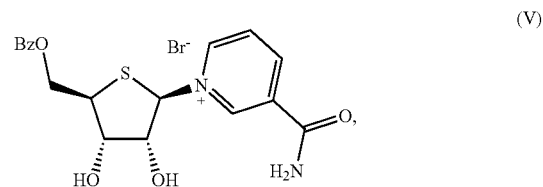

(V)

followed by deprotection of the compound of formula V to produce the compound of formula IV. In a further aspect of this method, deprotection of the compound of formula V to produce the compound of formula IV comprises or consists essentially of, or yet further consists of contacting the compound of formula V with ammonia and methanol.

In another aspect, a method of inhibiting enzymatic activity of CD38 is provided, comprising, or alternatively consisting essentially of, or yet further consisting of, contacting CD38 with a compound of formula I or an analogue compound of formula VI, or a pharmaceutically acceptable salt or solvate of either thereof, as well as a composition comprising the same:

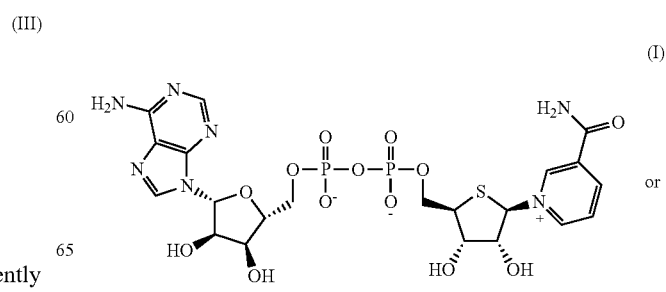

(I)

or

-continued

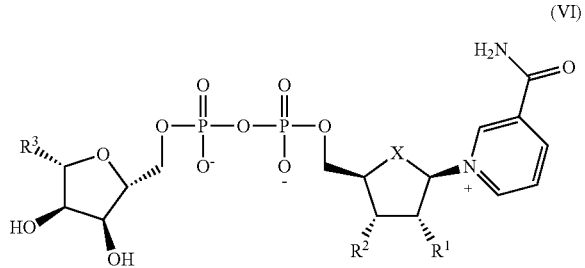

(VI)

wherein X is O or S;
R³ is selected from thymine, cytosine, adenine, uracil or guanine; and
R¹ and R² are each independently selected from the group consisting of hydroxyl, thiol, optionally substituted $C_1$-$C_8$ alkyl, optionally substituted $C_1$-$C_8$ alkenyl, optionally substituted $C_1$-$C_8$ alkynyl, optionally substituted $C_1$-$C_8$ alkoxy, optionally substituted $C_1$-$C_8$ alkenyloxy, optionally substituted $C_1$-$C_8$ alkynyloxy, optionally substituted heteroaryloxy, optionally substituted aryloxy, acyl, acylamino, acyloxy, optionally substituted amino, halo, aminocarbonyl, aminothiocarbonyl, aminocarbonylamino, aminocarbonyloxy, aminosulfonyl, aminosulfonyloxy, aminosulfonylamino azidyl, cyano, nitro, oxo, amidino, arylthio, carboxylate, optionally substituted $C_1$-$C_8$ carboxyl ester, optionally substituted $C_1$-$C_8$ (carboxyl ester) amino, optionally substituted $C_1$-$C_8$ (carboxyl ester) oxy, optionally substituted $C_1$-$C_8$ cycloalkyl, optionally substituted heterocycloalkyl, optionally substituted $C_1$-$C_8$ cycloalkenyl, optionally substituted $C_1$-$C_8$ cycloalkoxy, optionally substituted $C_1$-$C_8$ cycloalkylthio, optionally substituted $C_1$-$C_8$ cycloalkenyloxy, optionally substituted $C_1$-$C_8$ heterocyclyloxy, and OP wherein P is a protecting group.

In one aspect, the inhibition excludes or is not slow-onset inhibition. In some embodiments, the contacting can be in vitro or in vivo. When the contacting is in vivo, the subject is an animal or mammal, such as for example, a human, ovine, bovine, feline, canine, equine, simian, or murine. In a particular aspect, the subject is a human. In addition, when the contacting is in vivo, the contacting can comprises administering the compound of formula I, a pharmaceutically acceptable salt or a solvate thereof, to the subject.

In another aspect, a compound of formula I-A, or a pharmaceutically acceptable salt or solvate thereof, is provided:

(I-A)

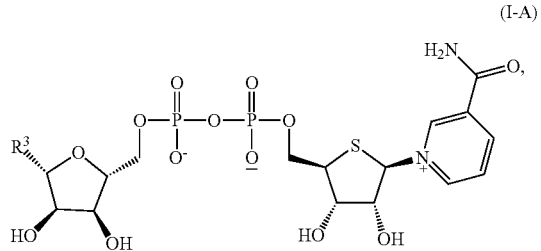

wherein R³ is selected from thymine, cytosine, adenine, uracil or guanine, as well as pharmaceutically acceptable salts and solvates thereof. The compounds can be combined with a carrier, such as a pharmaceutically acceptable carrier.

In another aspect, a compound of formula VI, or a pharmaceutically acceptable salt or solvate thereof, is provided:

(VI)

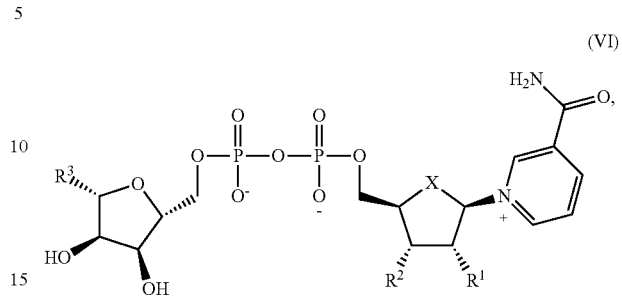

wherein:
X is O or S;
R³ is selected from thymine, cytosine, adenine, uracil or guanine; and
R¹ and R² are each independently selected from the group consisting of hydroxyl, thiol, optionally substituted $C_1$-$C_8$ alkyl, optionally substituted $C_1$-$C_8$ alkenyl, optionally substituted $C_1$-$C_8$ alkynyl, optionally substituted $C_1$-$C_8$ alkoxy, optionally substituted $C_1$-$C_8$ alkenyloxy, optionally substituted $C_1$-$C_8$ alkynyloxy, optionally substituted heteroaryloxy, optionally substituted aryloxy, acyl, acylamino, acyloxy, optionally substituted amino, halo, aminocarbonyl, aminothiocarbonyl, aminocarbonylamino, aminocarbonyloxy, aminosulfonyl, aminosulfonyloxy, aminosulfonylamino azidyl, cyano, nitro, oxo, amidino, arylthio, carboxylate, optionally substituted $C_1$-$C_8$ carboxyl ester, optionally substituted $C_1$-$C_8$ (carboxyl ester) amino, optionally substituted $C_1$-$C_8$ (carboxyl ester) oxy, optionally substituted $C_1$-$C_8$ cycloalkyl, optionally substituted heterocycloalkyl, optionally substituted $C_1$-$C_8$ cycloalkenyl, optionally substituted $C_1$-$C_8$ cycloalkoxy, optionally substituted $C_1$-$C_8$ cycloalkylthio, optionally substituted $C_1$-$C_8$ cycloalkenyloxy, optionally substituted $C_1$-$C_8$ heterocyclyloxy, and OP wherein P is a protecting group.

Also provided herein is a compound or composition as disclosed herein in a kit and instructions for use.

BRIEF DESCRIPTION OF DRAWINGS

(FIG. 2A) NR, (FIG. 2B) S—NR, (FIG. 2C) ATP, (FIG. 2D) NAD⁺, and (FIG. 2E) S-NAD⁺.

(FIG. 8A) 0.25 mM $NAD^+$ or $S-NAD^+$ was incubated with 250 µM Ac-RGK(Ac)-AMC peptide and 45.4 nM SIRT2 in reaction buffer (25 mM Tris, 150 mM NaCl, 1 mM DTT, pH 8.0) for overnight at room temperature, followed by additions of 50 nM bovine trypsin and measurements of fluorescence signals for 5 minutes. (FIG. 8B) 0.5 mM $NAD^+$ or $S-NAD^+$ or a mixture of 0.5 mM $NAD^+$ and 2 mM $S-NAD^+$ was incubated with 250 µM Ac-RGK(Ac)-AMC peptide and 45.4 nM SIRT2 in reaction buffer (25 mM Tris, 150 mM NaCl, 1 mM DTT, pH 8.0) for 30 minutes at room temperature. Following 15-minute incubation with 50 nM bovine trypsin, fluorescence intensities were determined.

(FIG. 10A) and (FIG. 10B) 0.5 mM $NAD^+$ was incubated with 2 mM L-glutamate and 20 unit/ml GDH in buffer containing 2 mM DTT, 50 mM Tris, pH 7.5 for 0 (FIG. 10A) or 30 minutes (FIG. 10B) at room temperature, followed by HPLC analysis. (FIG. 10C) and (FIG. 10D) 0.5 mM $NAD^+$ was incubated with 5 mM D-glucose 6-phosphate and 10 unit/ml G6PDH in buffer containing 5 mM $MgCl_2$, 50 mM Tris, pH 7.5 for 0 (FIG. 10C) or 30 minutes (FIG. 10D) at room temperature, followed by HPLC analysis.

(FIG. 11A) and (FIG. 11B) 0.5 mM $S-NAD^+$ was incubated with 2 mM L-glutamate and 20 unit/ml GDH in buffer containing 2 mM DTT, 50 mM Tris, pH 7.5 for 0 (FIG. 11A) or 30 minutes (FIG. 11B) at room temperature, followed by HPLC analysis. (FIG. 11C) and (FIG. 11D) 0.5 mM $S-NAD^+$ was incubated with 5 mM D-glucose 6-phosphate and 10 unit/ml G6PDH in buffer containing 5 mM $MgCl_2$, 50 mM Tris, pH 7.5 for 0 (FIG. 11C) or 30 minutes (FIG. 11D) at room temperature, followed by HPLC analysis.

(FIG. 12A) Overlaid x-ray structures of $S-NAD^+$-bound catalytically active CD38 (grey), $NAD^+$-bound catalytically inactive CD38 (green) (E226Q) (PDB ID: 2165), and apo-CD38 (blue) (PDB ID: 1YH3). (FIG. 12B) and (FIG. 12C) $NAD^+$ (green) and $S-NAD^+$ (magenta) at the binding sites of catalytically inactive CD38 (E226Q) (green) and active CD38 (grey) with indicated key interacting residues.

(FIG. 14A) Schemes of enzymatic conversion of NR and S—NR to $NAD^+$ and $S-NAD^+$. (FIG. 14B)-(FIG. 14E) HPLC analysis of enzymatic synthesis of $NAD^+$ ((FIG. 14B) and (FIG. 14C)) and $S-NAD^+$ ((FIG. 14D) and (FIG. 14E)) by human NRK1 and NMNAT1 as measured by UV absorbance at 260 nm. 2 mM NR or S—NR was incubated with 6 mM ATP and 5 µM NRK1 and 5 µM NMNAT1 at RT for 0 h and 4 h, followed by HPLC analysis.

(FIG. 17A) Overall crystal complex structure of human CD38-S-$NAD^+$. (FIG. 17B) and (FIG. 17C) Bound $S-NAD^+$ at the active site of human CD38 with indicated catalytic residues and interacting water molecules. PDB ID: 6EDR.

DETAILED DESCRIPTION

Figure 1:
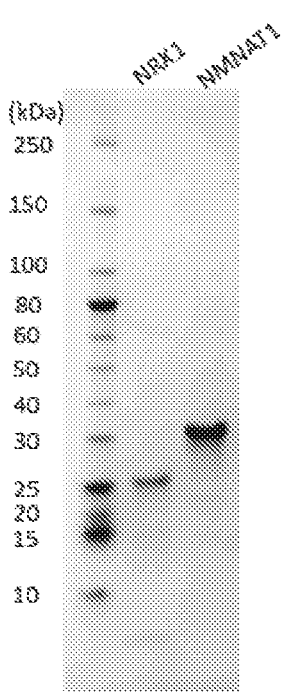
FIG. 1: SDS-PAGE gel of the purified human NRK1 and NMNAT1.
Figures 2A, 2B, 2C, 2D, 2E:
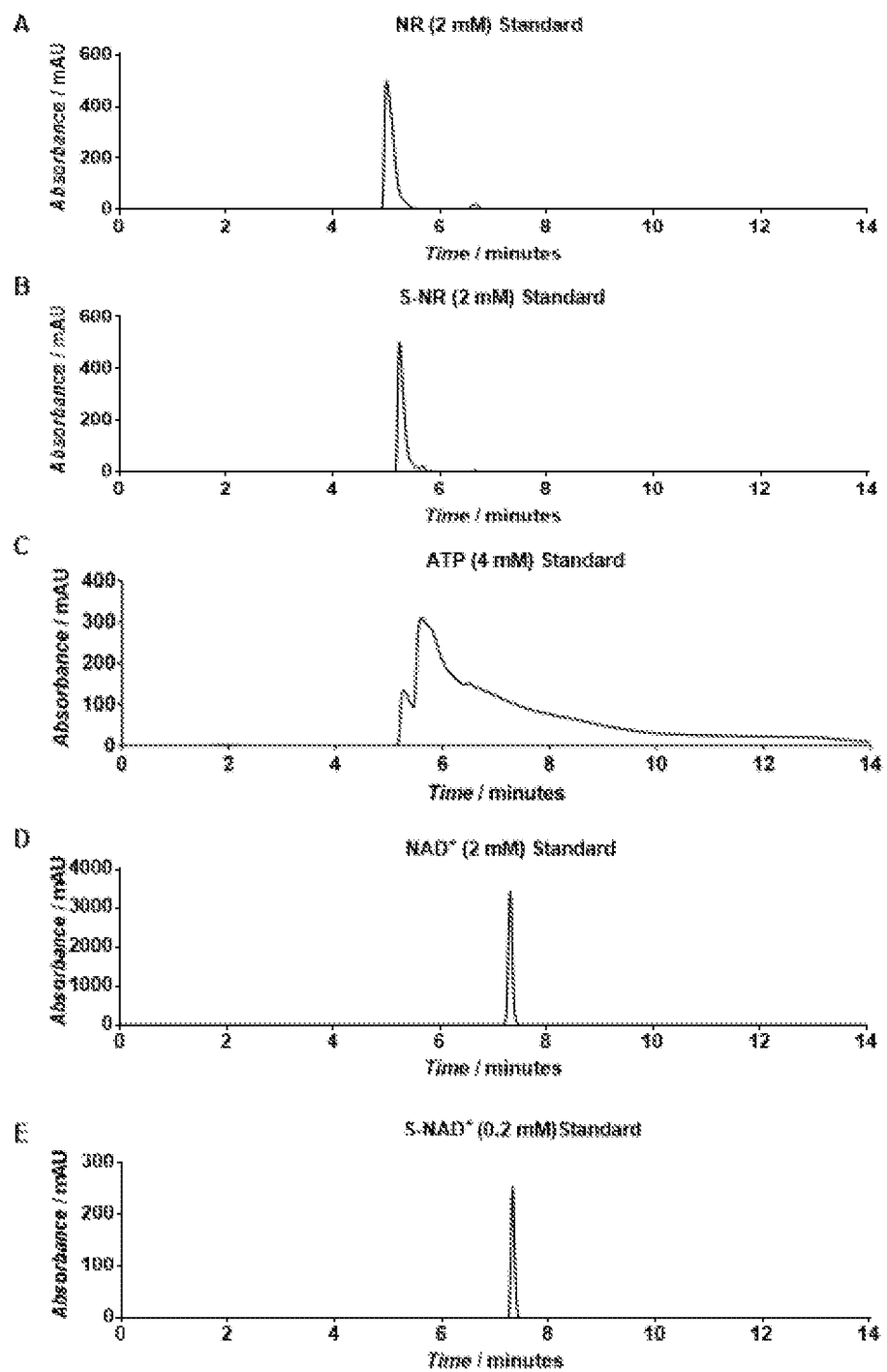
FIGS. 2A-2E: HPLC analysis of standard compounds as measured by UV absorbance at 260 nm.
Figures 3A, 3B, 3C, 3D:
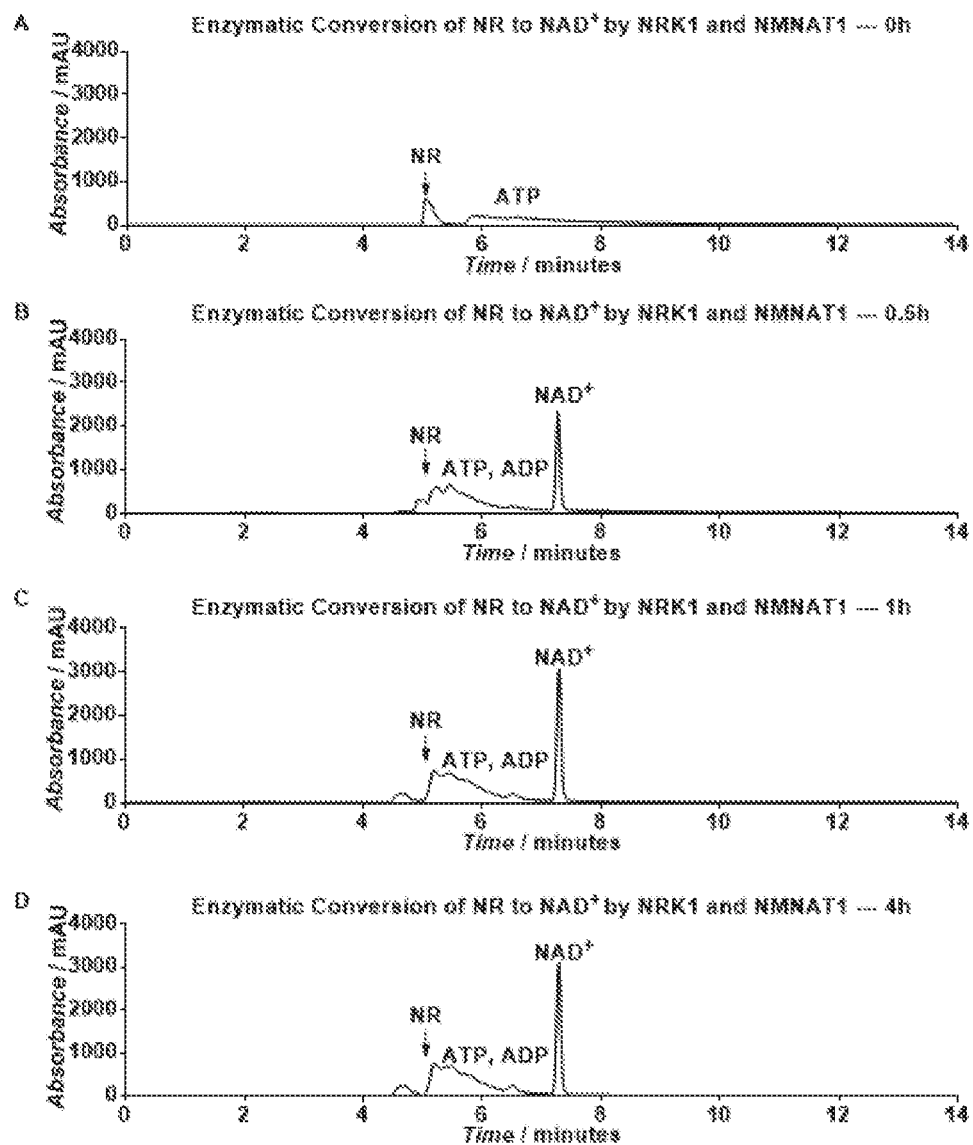
FIGS. 3A-3D: HPLC analysis of enzymatic synthesis of NAD⁺ by the purified NRK1 and NMNAT1 as measured by UV absorbance at 260 nm. 2 mM NR was incubated with 6 mM ATP and 5 μM NRK1 and 5 μM NMNAT1 at RT for 0 h (FIG. 3A), 0.5 h (FIG. 3B), 1 h (FIG. 3C), and 4 h (FIG. 3D), followed by HPLC analysis.
Figures 4A, 4B, 4C, 4D:
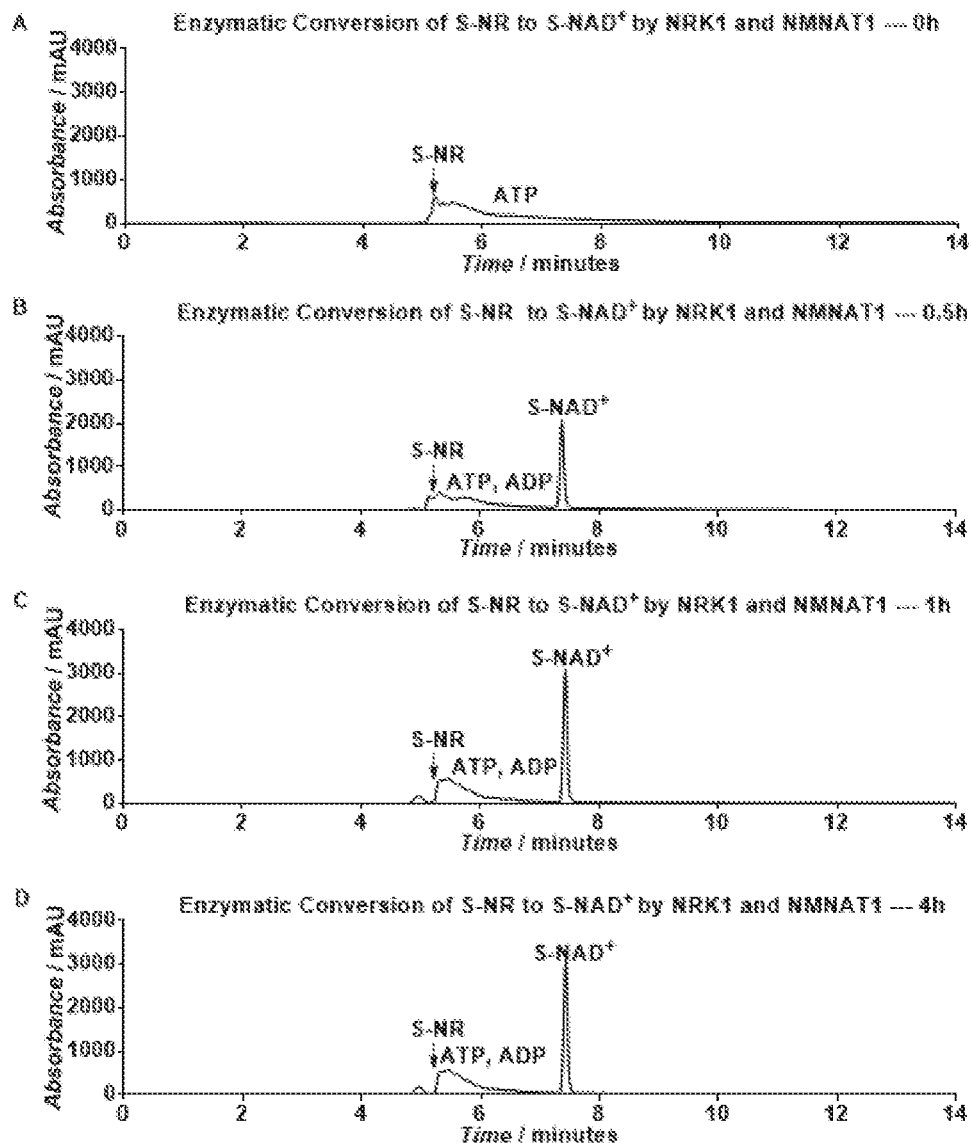
FIGS. 4A-4D: HPLC analysis of enzymatic synthesis of S-NAD⁺ by the purified NRK1 and NMNAT1 as measured by UV absorbance at 260 nm. 2 mM S—NR was incubated with 6 mM ATP and 5 μM NRK1 and 5 μM NMNAT1 at RT for 0 h (FIG. 4A), 0.5 h (FIG. 4B), 1 h (FIG. 4C), and 4 h (FIG. 4D), followed by HPLC analysis.

Throughout this disclosure, various publications, patents and published patent specifications are referenced by an identifying citation. Several references are referenced by an Arabic number, and the complete citation for is found preceding the claims in the References section of this disclosure. The disclosures of these publications, patents and published patent specifications are hereby incorporated by reference into the present disclosure in their entirety to more fully describe the state of the art to which this invention pertains.

Definitions

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2$^{nd}$ edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Names and G. R. Taylor eds. (1995)), Harlow and Lane, eds. (1988) Antibodies, a Laboratory Manual, and Animal Cell Culture (R. I. Freshney, ed. (1987)).

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

"Slow-onset inhibition," as used herein, intends that binding of an inhibitor to an enzyme target induces structural changes for the enzyme molecule and results in tighter binding over reaction time. If this occurs to an inhibitor, it typically indicates potentially higher potency for inhibiting the target enzyme.

"Optionally substituted" refers to a group selected from that group and a substituted form of that group. A "substituted" group, refers to that group substituted with a substituent described or defined below. Substituted groups are defined herein. In one embodiment, substituents are selected from, for example, $C_1$-$C_{10}$ or $C_1$-$C_6$ alkyl, $C_2$-$C_6$ alkenyl, $C_2$-$C_6$ alkynyl, $C_6$-$C_{10}$ aryl, $C_3$-$C_8$ cycloalkyl, $C_2$-$C_{10}$ heterocyclyl, $C_1$-$C_{10}$ heteroaryl, halo, —$N_3$, nitro, cyano, —$CO_2H$ or a $C_1$-$C_6$ alkyl ester thereof, or any of the functional groups described or defined below.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). A Cx-Cy alkyl will be understood to have from x to y carbons.

"Alkenyl" refers to monovalent straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$— or —$CH(CH_3)CH_2$—), butylene (—$CH_2CH_2CH_2CH_2$—), isobutylene (—$CH_2CH(CH_3)CH_2$—), sec-butylene (—$CH_2CH_2(CH_3)CH$—), and the like. Similarly, "alkenylene" and "alkynylene" refer to an alkylene moiety containing respective 1 or 2 carbon carbon double bonds or a carbon carbon triple bond.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups, or having from 1-3 carbon atoms replaced with —O—, —S—, or $NR^Q$— moieties where $R^Q$ is H or $C_1$-$C_6$ alkyl. It is to be noted that when the alkylene is substituted by an oxo group, 2 hydrogens attached to the same carbon of the alkylene group are replaced by "═O". "Substituted alkenylene" and "substituted alkynylene" refer to alkenylene and substituted alkynylene moieties substituted with substituents as described for substituted alkylene.

A "protecting group" or "PZ" (wherein z is an integer) intends any protecting group for an alcohol(s) well known in the art. Non-limiting examples include 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), benzyloxymethyl acetal (BOM), methoxymethyl acetal (MOM), methoxypropyl acetal (MOP), methyl ether, tetrahydropyranyl acetal (THP), triethylsilyl ether (TES), triisopropylsilyl ether (TIPS), trimethylsilyl ether (TMS), tert-Butyldimethylsilyl ether (TBS, TBDMS), or tert-butyldiphenylsilyl ether (TBDPS). In the case of a 1,2 diol suitable protecting groups include acetonide, benzaldehyde acetal or carbonate. These protecting groups and others are well known to the skilled artisan, as evidenced by Green et al: Greene's Protective Groups in Organic Synthesis, Fourth Edition Author(s): Peter G. M. Wuts and Theodora W. Greene First published: 10 Apr. 2006, Copyright (c) 2007 John Wiley & Sons, Inc, the disclosure of which is incorporated by reference.

"Deprotection," "deprotecting," and the like, intend removal of the protecting group by any conventional means known to the skilled artisan or present in Green et al. It will be readily apparent that the conditions for deprotecting depend upon which protecting group is used.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{47}C(O)$alkyl, —$NR^{47}C(O)$substituted alkyl, —$NR^{47}C(O)$cycloalkyl, —$NR^{47}C(O)$substituted cycloalkyl, —$NR^{47}C(O)$cycloalkenyl, —$NR^{47}C(O)$substituted cycloalkenyl, —$NR^{47}C(O)$alkenyl, —$NR^{47}C(O)$substituted alkenyl, —$NR^{47}C(O)$alkynyl, —$NR^{47}C(O)$substituted alkynyl, —$NR^{47}C(O)$aryl, —$NR^{47}C(O)$substituted aryl, —$NR^{47}C(O)$heteroaryl, —$NR^{47}C(O)$substituted heteroaryl, —$NR^{47}C(O)$heterocyclic, and —$NR^{47}C(O)$substituted heterocyclic wherein $R^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{48}R^{49}$ where $R^{48}$ and $R^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R$^{48}$ and R$^{49}$ are optionally joined, together with the nitrogen bound thereto to form a heterocyclic or substituted heterocyclic group, provided that R$^{48}$ and R$^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R$^{48}$ is hydrogen and R$^{49}$ is alkyl, the substituted amino group is sometimes referred to herein as alkylamino. When R$^{48}$ and R$^{49}$ are alkyl, the substituted amino group is sometimes referred to herein as dialkylamino. When referring to a monosubstituted amino, it is meant that either R$^{48}$ or R$^{49}$ is hydrogen but not both. When referring to a disubstituted amino, it is meant that neither R$^{48}$ nor R$^{49}$ are hydrogen.

"Aminocarbonyl" refers to the group —C(O)NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{47}$C(O)NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^{47}$C(S)NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —SO$_2$NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—SO$_2$NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{47}$SO$_2$NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{52}$)NR$^{50}$R$^{51}$ where $R^{50}$, $R^{51}$, and $R^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Azide" refers to the group —N=N$^{\oplus}$=N$^{\ominus}$.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR$^{47}$C(O)O-alkyl, —NR$^{47}$C(O)O-substituted alkyl, —NR$^{47}$C(O)O-alkenyl, —NR$^{47}$C(O)O-substituted alkenyl, —NR$^{47}$C(O)O-alkynyl, —NR$^{47}$C(O)O-substituted alkynyl, —NR$^{47}$C(O)O-aryl, —NR$^{47}$C(O)O-substituted aryl, —NR$^{47}$C(O)O-cycloalkyl, —NR$^{47}$C(O)O-substituted cycloalkyl, —NR$^{47}$C(O)O-cycloalkenyl, —NR$^{47}$C(O)O-substituted cycloalkenyl, —NR$^{47}$C(O)O-heteroaryl, —NR$^{47}$C(O)O-substituted heteroaryl, —NR$^{47}$C(O)O-heterocyclic, and —NR$^{47}$C(O)O-substituted heterocyclic wherein $R^{47}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. The fused ring can be an aryl ring provided that the non aryl part is joined to the rest of the molecule. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidine" refers to the group —NHC(=NH)NH$_2$.

"Substituted guanidino" refers to —NR$^{53}$C(=NR$^{53}$)N(R$^{53}$)$_2$ where each R$^{53}$ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two R$^{53}$ groups attached to a common guanidino nitrogen atom are optionally joined together with the nitrogen bound thereto to form a heterocyclic or substituted heterocyclic group, provided that at least one R$^{53}$ is not hydrogen, and wherein said substituents are as defined herein.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Certain non-limiting examples include pyridinyl, pyrrolyl, indolyl, thiophenyl, oxazolyl, thizolyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and Spiro ring systems. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O).

Phenylene refers to a divalent aryl ring, where the ring contains 6 carbon atoms.

Substituted phenylene refers to phenylenes which are substituted with 1 to 4, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

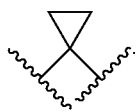 [SMILES: *C1(*)CC1]

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-SO$_2$—, phenyl-SO$_2$—, and 4-methylphenyl-SO$_2$—.

"Substituted sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —C(=S)—.

"Thioxo" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

An animal, subject or patient for diagnosis, treatment, or administration of the compounds if the disclosure thereto, refers to an animal such as a mammal, or a human, ovine, bovine, feline, canine, equine, simian, etc. Non-human animals subject to diagnosis, treatment, or administration thereto of compounds of the disclosure include, for example, simians, murine, such as, rat, mice, canine, leporid, livestock, sport animals, and pets.

A "composition" "pharmaceutical composition" as used herein, intends an active agent, such as a compound as disclosed herein and a carrier, inert or active. The carrier can be, without limitation, solid such as a bead or resin, or liquid, such as phosphate buffered saline.

Administration or treatment in "combination" refers to administering two agents such that their pharmacological effects are manifest at the same time. Combination does not require administration at the same time or substantially the same time, although combination can include such administrations.

"Pharmaceutically acceptable salt" refers to salts of a compound, which salts are suitable for pharmaceutical use and are derived from a variety of organic and inorganic counter ions well known in the art and include, when the compound contains an acidic functionality, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "Handbook of Pharmaceutically Acceptable Salts," (2002), Verlag Helvetica Chimica Acta, Zurich, Switzerland), for a discussion of pharmaceutical salts, their selection, preparation, and use.

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

A solvate of a compound is a solid-form of a compound that crystallizes with less than one, one or more than one molecules of a solvent inside in the crystal lattice. A few examples of solvents that can be used to create solvates, such as pharmaceutically acceptable solvates, include, but are not limited to, water, $C_1$-$C_6$ alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some embodiments, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

An "effective amount" is an amount sufficient to effect beneficial or desired results. An effective amount can be administered in one or more administrations, applications or dosages and is determined by the system in which the drug or compound is delivered, e.g., an effective amount for in vitro purposes is not the same as an effective amount for in vivo purposes. For in vivo purposes, the delivery and "effective amount" is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

Nicotinamide riboside kinase (NRK) is an enzyme with systematic name ATP:beta-D-ribosylnicotinate 5-phosphotransferase. This enzyme catalyzes the following chemical reaction:

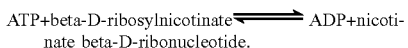
ATP+beta-D-ribosylnicotinate ⇌ ADP+nicotinate beta-D-ribonucleotide.

Nicotinamide mononucleotide adenylyltransferase (NM-NAT) is an enzyme that catalyzes the chemical reaction:

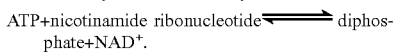
ATP+nicotinamide ribonucleotide ⇌ diphosphate+NAD⁺.

"Nicotinamide adenine dinucleotide ($NAD^+$) (also known as diphosphopyridine nucleotide (DPN+) and Coenzyme I) intends the coenzyme found in all cells. The compound is a dinucleotide, and it consists of two nucleotides joined through their phosphate groups. The chemical structure is provide below:

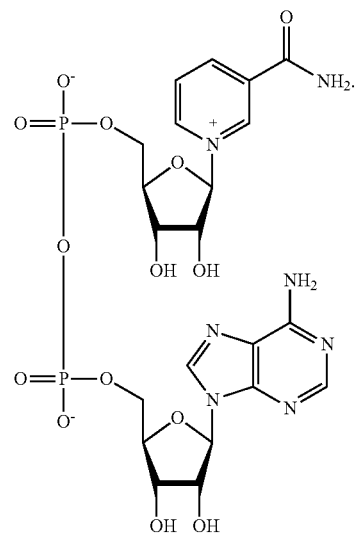

4'-thioribose NAD+ (S-NAD+) intends the coenzyme thiol analogue shown below. This compound is a compound of formula I. The chemical structure is provide below:

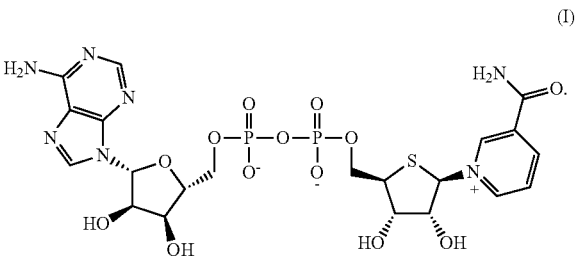

(I)

As used herein, the term "detectable label" intends a directly or indirectly detectable compound or composition that is conjugated directly or indirectly to the composition to be detected, e.g., N-terminal histidine tags (N-His), magnetically active isotopes, e.g., $^{115}Sn$, $^{117}Sn$ and $^{119}Sn$, a non-radioactive isotopes such as $^{13}C$ and $^{15}N$, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

"Affinity label" as used herein refers to a compound, that way be appended to a protein or another compound so that the protein or other compound can be purified from its crude source using an affinity purification technique, for example affinity chromatography, wherein the purification processes selects for the affinity label and the protein or other compound appended thereto based on the label's interactions with an affinity matrix used for the purification. These interactions include, but are not limited to, antigen-antibody interactions, enzyme-substrate interactions, receptor-ligand interactions, hydrogen bonding, ionic interactions or electrostatic interactions. Non-limiting examples of affinity labels include chitin binding protein (CBP), maltose binding protein (MBP), Strep-tag, glutathione-S-transferase (GST), poly(His) tags, NE-tag, Spot-tag, albumin-binding protein (ABP), alkaline phosphatase (AP), AU epitopes, bacteriophage T7 or V5 epitope, HSV epitope, biotin-carboxy carrier protein, biotin, and bluetongue virus tag (B-tag). Non limiting examples of matrices include, but are not limited to, albumin/low pH, mAb/low pH, avidin or streptavidin/biotin or denaturation, calmodulin/EGTA or EGTA and high salt, chloramphenicol/chloramphenicol, chitin, choline, methotrexate/folate, galactose, glutathione, and a divalent metal.

As used herein, the term "contacting" intends bringing the reagents into close proximity with each other so that a chemical or biochemical reaction can occur among the reagents. In one aspect, the term intends admixing the components, either in a reaction vessel or on a plate or dish. In another aspect, it intends in vivo administration to a subject.

The term "binding" or "binds" as used herein are meant to include interactions between molecules that may be covalent or non-covalent which, in one embodiment, can be detected using, for example, a hybridization assay. The terms are also meant to include "binding" interactions between molecules. Interactions may be, for example, protein-protein, antibody-protein, protein-nucleic acid, protein-small molecule or small molecule-nucleic acid in nature. This binding can result in the formation of a "complex" comprising the interacting molecules. A "complex" refers to the binding of two or more molecules held together by covalent or non-covalent bonds, interactions or forces.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein. The term "peptide fragment," as used herein, also refers to a peptide chain.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid.

Compounds

In another aspect, a compound of formula I-A, or a pharmaceutically acceptable salt or solvate thereof, is provided:

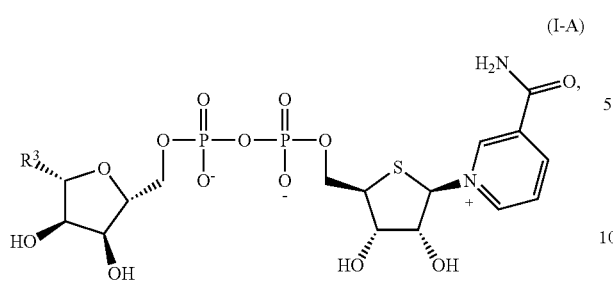

(I-A)

wherein R³ is selected from thymine, cytosine, adenine, uracil or guanine, as well as pharmaceutically acceptable salts and solvates thereof. The compounds can be combined with a carrier, such as a pharmaceutically acceptable carrier.

In a preferred embodiment, the compound of formula I-A is a compound of formula I:

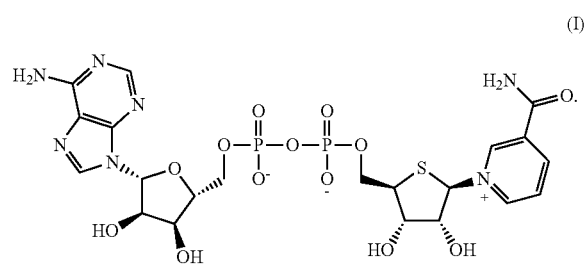

(I)

In another aspect, a compound of formula VI, or a pharmaceutically acceptable salt or solvate thereof, is provided:

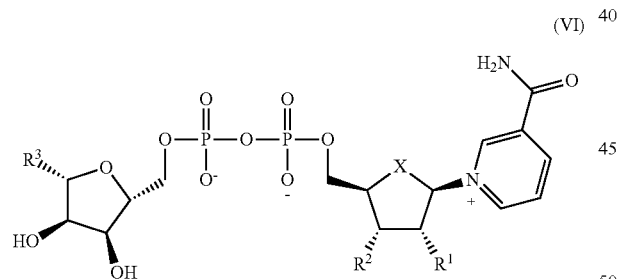

(VI)

wherein:
X is O or S;
R³ is selected from thymine, cytosine, adenine, uracil or guanine; and
R¹ and R² are each independently selected from the group consisting of hydroxyl, thiol, optionally substituted $C_1$-$C_8$ alkyl, optionally substituted $C_1$-$C_8$ alkenyl, optionally substituted $C_1$-$C_8$ alkynyl, optionally substituted $C_1$-$C_8$ alkoxy, optionally substituted $C_1$-$C_8$ alkenyloxy, optionally substituted $C_1$-$C_8$ alkynyloxy, optionally substituted heteroaryloxy, optionally substituted aryloxy, acyl, acylamino, acyloxy, optionally substituted amino, halo, aminocarbonyl, aminothiocarbonyl, aminocarbonylamino, aminocarbonyloxy, aminosulfonyl, aminosulfonyloxy, aminosulfonylamino azidyl, cyano, nitro, oxo, amidino, arylthio, carboxylate, optionally substituted $C_1$-$C_8$ carboxyl ester, optionally substituted $C_1$-$C_8$ (carboxyl ester) amino, optionally substituted $C_1$-$C_8$ (carboxyl ester) oxy, optionally substituted $C_1$-$C_8$ cycloalkyl, optionally substituted heterocycloalkyl, optionally substituted $C_1$-$C_8$ cycloalkenyl, optionally substituted $C_1$-$C_8$ cycloalkoxy, optionally substituted $C_1$-$C_8$ cycloalkylthio, optionally substituted $C_1$-$C_8$ cycloalkenyloxy, optionally substituted $C_1$-$C_8$ heterocyclyloxy, and OP wherein P is a protecting group.

In some embodiments, the protecting groups is selected from 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), benzyloxymethyl acetal (BOM), methoxymethyl acetal (MOM), methoxypropyl acetal (MOP), methyl ether, tetrahydropyranyl acetal (THP), triethylsilyl ether (TES), triisopropylsilyl ether (TIPS), trimethylsilyl ether (TMS), tert-Butyldimethylsilyl ether (TBS, TBDMS), or tert-butyldiphenylsilyl ether (TBDPS).

In some embodiments, R¹ and R² are each independently selected from the group consisting of hydroxyl, optionally substituted $C_1$-$C_8$ alkyl, optionally substituted $C_1$-$C_8$ alkenyl, optionally substituted $C_1$-$C_8$ alkynyl, optionally substituted $C_1$-$C_8$ alkoxy, optionally substituted $C_1$-$C_8$ alkenyloxy, optionally substituted $C_1$-$C_8$ alkynyloxy, optionally substituted heteroaryloxy, optionally substituted aryloxy, optionally substituted $C_1$-$C_8$ cycloalkoxy, optionally substituted $C_1$-$C_8$ heterocyclyloxy and azidyl.

In some embodiments,
R¹ and R² are both hydroxyl;
R¹ is propargyl and R² is hydroxyl;
R¹ is hydroxyl and R² is propargyl;
R¹ is pent-4-yn-1-yloxy and R² is hydroxyl;
R¹ is hydroxyl and R² is pent-4-yn-1-yloxy;
R¹ is azidyl and R² is hydroxyl; or
R¹ is hydroxyl and R² is azidyl.

Methods of Synthesis

Also provided herein are methods of synthesizing an analogue compound of formula VI:

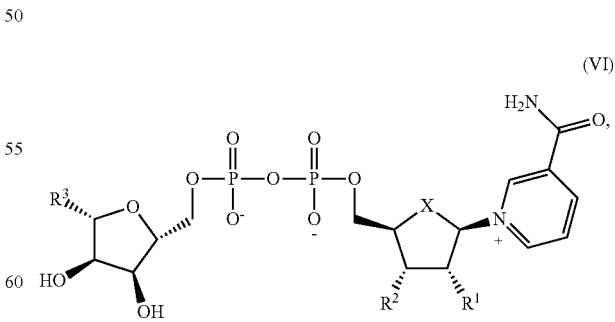

(VI)

or a pharmaceutically acceptable salt or solvate thereof, the method comprising, or consisting essentially of, or yet further consisting of, enzymatically converting a compound of formula VII:

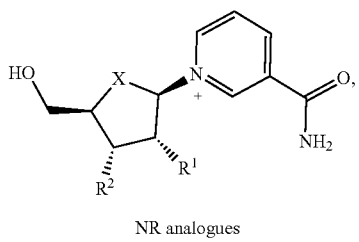

NR analogues to the analogue compound of Formula VI, wherein:
X is S or O;
R³ is selected from thymine, cytosine, adenine, uracil or guanine; and
R¹ and R² are each independently selected from the group consisting of hydroxyl, thiol, optionally substituted $C_1$-$C_8$ alkyl, optionally substituted $C_1$-$C_8$ alkenyl, optionally substituted $C_1$-$C_8$ alkynyl, optionally substituted $C_1$-$C_8$ alkoxy, optionally substituted $C_1$-$C_8$ alkenyloxy, optionally substituted $C_1$-$C_8$ alkynyloxy, optionally substituted heteroaryloxy, optionally substituted aryloxy, acyl, acylamino, acyloxy, optionally substituted amino, halo, aminocarbonyl, aminothiocarbonyl, aminocarbonylamino, aminocarbonyloxy, aminosulfonyl, aminosulfonyloxy, aminosulfonylamino azidyl, cyano, nitro, oxo, amidino, arylthio, carboxylate, optionally substituted $C_1$-$C_8$ carboxyl ester, optionally substituted $C_1$-$C_8$ (carboxyl ester) amino, optionally substituted $C_1$-$C_8$ (carboxyl ester) oxy, optionally substituted $C_1$-$C_8$ cycloalkyl, optionally substituted heterocycloalkyl, optionally substituted $C_1$-$C_8$ cycloalkenyl, optionally substituted $C_1$-$C_8$ cycloalkoxy, optionally substituted $C_1$-$C_8$ cycloalkylthio, optionally substituted $C_1$-$C_8$ cycloalkenyloxy, optionally substituted $C_1$-$C_8$ heterocyclyloxy, and OP wherein P is a protecting group.

In some embodiments, the protecting groups is selected from 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), benzyloxymethyl acetal (BOM), methoxymethyl acetal (MOM), methoxypropyl acetal (MOP), methyl ether, tetrahydropyranyl acetal (THP), triethylsilyl ether (TES), triisopropylsilyl ether (TIPS), trimethylsilyl ether (TMS), tert-Butyldimethylsilyl ether (TBS, TBDMS), or tert-butyldiphenylsilyl ether (TBDPS).

In some embodiments, R¹ and R² are each independently selected from the group consisting of hydroxyl, optionally substituted $C_1$-$C_8$ alkyl, optionally substituted $C_1$-$C_8$ alkenyl, optionally substituted $C_1$-$C_8$ alkynyl, optionally substituted $C_1$-$C_8$ alkoxy, optionally substituted $C_1$-$C_8$ alkenyloxy, optionally substituted $C_1$-$C_8$ alkynyloxy, optionally substituted heteroaryloxy, optionally substituted aryloxy, optionally substituted $C_1$-$C_8$ cycloalkoxy, optionally substituted $C_1$-$C_8$ heterocyclyloxy and azidyl.

In some embodiments,
R¹ and R² are both hydroxyl;
R¹ is propargyl and R² is hydroxyl;
R¹ is hydroxyl and R² is propargyl;
R¹ is pent-4-yn-1-yloxy and R² is hydroxyl;
R¹ is hydroxyl and R² is pent-4-yn-1-yloxy;
R¹ is azidyl and R² is hydroxyl; or
R¹ is hydroxyl and R² is azidyl.

In one aspect, enzymatically converting the compound to the compound of an analogue formula VI, the method comprises, or consists essentially of, or yet further consists of, contacting the compound of an analogue of formula VII with adenosine triphosphate (ATP), nicotinamide riboside kinase (NRK), and nicotinamide mononucleotide adenylyltransferase (NMNAT). In one aspect, the contacting is for less than 7 hours, or less than 6 hours, or less than 5 hours, or less than 4 hours, or less than 3 hours, or less than 2 hours, or less than 1 hour.

More specifically, enzymatic synthesis of NAD⁺ analogues from their corresponding nicotinamide riboside (NR) analogues may be carried out as follows. NR analogue is added to the reaction with NRK (5 μM), NMNAT (5 μM), and ATP (5 mM) in reaction buffer (50 mM Tris-HCl, pH 7.5, 100 mM NaCl, 20 mM $MgCl_2$, 1 mM DTT) to the final concentration of 1 mM. After the reaction is completed (monitoring by HPLC), the reaction is quenched by adding 50% TCA to a final concentration of 10% and purified by HPLC.

The present disclosure also includes synthetic methods and novel intermediates for the synthesis of, e.g., a compound of formula I-A or I.

In one aspect, a method of synthesizing a compound of formula I:

or a pharmaceutically acceptable salt or solvate thereof is provided, comprising the step of enzymatically converting a compound of formula IV:

to the compound of formula I.

In one aspect, a method of synthesizing a compound of formula I-A:

or a pharmaceutically acceptable salt or solvate thereof is provided, comprising the step of enzymatically converting a compound of formula IV:

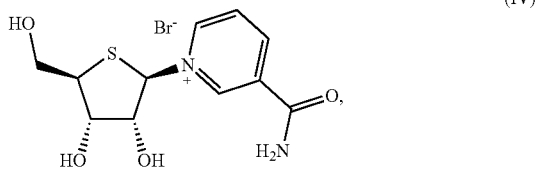

(IV)

to the compound of formula I-A, wherein R³ is selected from thymine, cytosine, adenine, uracil or guanine.

In some embodiments, enzymatically converting the compound of formula IV to the compound of formula I or I-A comprises, consists essentially of, or yet further consists of, contacting the compound of formula IV with adenosine triphosphate (ATP), nicotinamide riboside kinase (NRK), and nicotinamide mononucleotide adenylyltransferase (NMNAT). In some embodiments, the contacting is for less than 5 hours. In some embodiments, the contacting is for less than 4 hours. In some embodiments, the contacting is for less than 3 hours. In some embodiments, the contacting is for less than 2 hours. In some embodiments, the contacting is for less than 1 hour.

In some embodiments, the method further comprises the step of converting a compound of formula II:

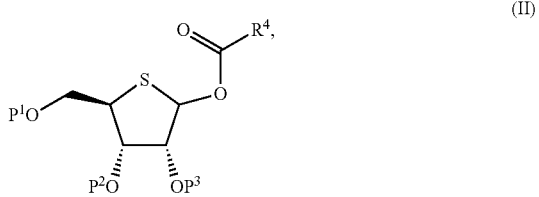

(II)

into a compound of formula III:

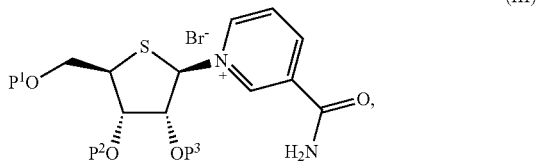

(III)

wherein R⁴ is an optionally substituted C₁-C₈ alkyl;
P¹, P² and P³ are protecting groups each independently selected from 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), benzyloxymethyl acetal (BOM), methoxymethyl acetal (MOM), methoxypropyl acetal (MOP), methyl ether, tetrahydropyranyl acetal (THP), triethylsilyl ether (TES), triisopropylsilyl ether (TIPS), trimethylsilyl ether (TMS), tert-Butyldimethylsilyl ether (TBS, TBDMS), or tert-butyldiphenylsilyl ether (TBDPS); or P² and P³ together with the oxygens to which they are attached, together form an acetonide, benzaldehyde acetal or carbonate.

In some embodiments, R⁴ is methyl. In some embodiments, P¹ is Bz. In some embodiments, P² and P³ along with the oxygens to which they are attached, together form an acetonide. In some embodiments, R⁴ is methyl; P¹ is Bz; and P² and P³ along with the oxygens to which they are attached, together form an acetonide.

In some embodiments, the method further comprises, the step of deprotecting the compound of formula III to produce the compound of formula IV. In some embodiments, R⁴ is methyl; P¹ is Bz; and P² and P³ along with the oxygens to which they are attached, together form an acetonide, and deprotecting the compound of formula III to produce the compound of formula IV comprises contacting the compound of formula III with trifluoroacetic acid (TFA) to produce a compound of formula V:

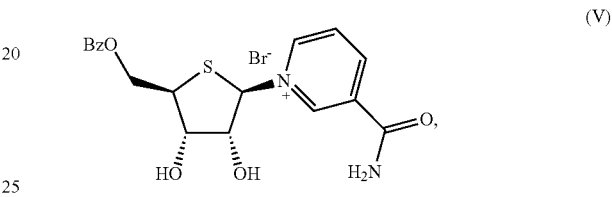

(V)

followed by deprotection of the compound of formula V to produce the compound of formula IV. In some embodiments, deprotection of the compound of formula V to produce the compound of formula IV comprises contacting the compound of formula V with ammonia and methanol.

Methods of Inhibiting CD38

In another aspect, a method of inhibiting enzymatic activity of CD38 is provided, comprising, or alternatively consisting essentially of, or yet further consists of, contacting CD38 with a compound of formula I or an analogue compound of formula VI, or a pharmaceutically acceptable salt or solvate of either thereof, as well as a composition comprising the same:

(I)

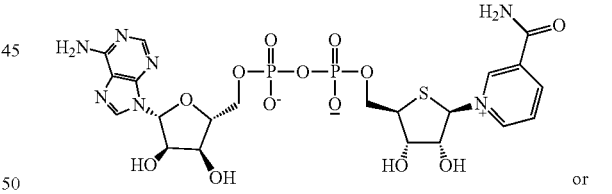

or

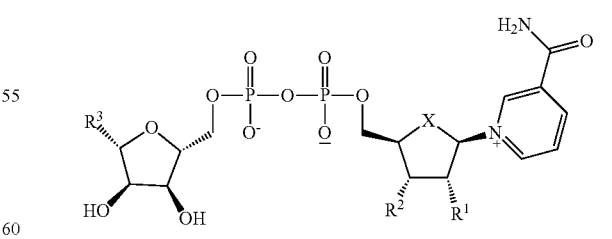

(VI)

wherein X is O or S;
R³ is selected from thymine, cytosine, adenine, uracil or guanine; and
R¹ and R² are each independently selected from the group consisting of hydroxyl, thiol, optionally substituted C₁-C₈ alkyl, optionally substituted C₁-C₈ alkenyl, optionally substituted $C_1$-$C_8$ alkynyl, optionally substituted $C_1$-$C_8$ alkoxy, optionally substituted $C_1$-$C_8$ alkenyloxy, optionally substituted $C_1$-$C_8$ alkynyloxy, optionally substituted heteroaryloxy, optionally substituted aryloxy, acyl, acylamino, acyloxy, optionally substituted amino, halo, aminocarbonyl, aminothiocarbonyl, aminocarbonylamino, aminocarbonyloxy, aminosulfonyl, aminosulfonyloxy, aminosulfonylamino azidyl, cyano, nitro, oxo, amidino, arylthio, carboxylate, optionally substituted $C_1$-$C_8$ carboxyl ester, optionally substituted $C_1$-$C_8$ (carboxyl ester) amino, optionally substituted $C_1$-$C_8$ (carboxyl ester) oxy, optionally substituted $C_1$-$C_8$ cycloalkyl, optionally substituted heterocycloalkyl, optionally substituted $C_1$-$C_8$ cycloalkenyl, optionally substituted $C_1$-$C_8$ cycloalkoxy, optionally substituted $C_1$-$C_8$ cycloalkylthio, optionally substituted $C_1$-$C_8$ cycloalkenyloxy, optionally substituted $C_1$-$C_8$ heterocyclyloxy, and OP wherein P is a protecting group.

In some embodiments, $R^1$ and $R^2$ are each independently selected from the group consisting of hydroxyl, optionally substituted $C_1$-$C_8$ alkyl, optionally substituted $C_1$-$C_8$ alkenyl, optionally substituted $C_1$-$C_8$ alkynyl, optionally substituted $C_1$-$C_8$ alkoxy, optionally substituted $C_1$-$C_8$ alkenyloxy, optionally substituted $C_1$-$C_8$ alkynyloxy, optionally substituted heteroaryloxy, optionally substituted aryloxy, optionally substituted $C_1$-$C_8$ cycloalkoxy, optionally substituted $C_1$-$C_8$ heterocyclyloxy and azidyl.

In some embodiments,
$R^1$ and $R^2$ are both hydroxyl;
$R^1$ is propargyl and $R^2$ is hydroxyl;
$R^1$ is hydroxyl and $R^2$ is propargyl;
$R^1$ is pent-4-yn-1-yloxy and $R^2$ is hydroxyl;
$R^1$ is hydroxyl and $R^2$ is pent-4-yn-1-yloxy;
$R^1$ is azidyl and $R^2$ is hydroxyl; or
$R^1$ is hydroxyl and $R^2$ is azidyl.

In one aspect, the inhibition excludes or is not slow-onset inhibition. In some embodiments, the contacting can be in vitro or in vivo. When the contacting is in vivo, the subject is an animal or mammal, such as for example, a human, ovine, bovine, feline, canine, equine, simian, or murine. In a particular aspect, the subject is a human. In addition, when the contacting is in vivo, the contacting can comprises administering the compound of formula I, a pharmaceutically acceptable salt or a solvate thereof, to the subject.

In another aspect, a method of inhibiting enzymatic activity of CD38 is provided, the method comprising, or alternatively consisting essentially of, or yet further consisting of, contacting CD38 with a compound of formula I:

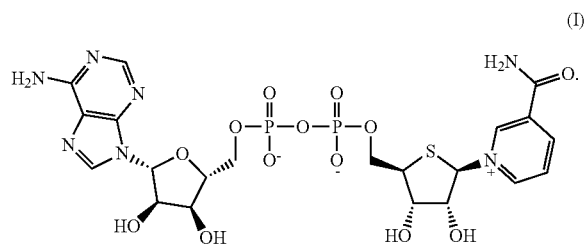

(I)

In some embodiments, the inhibition is not slow-onset inhibition. In some embodiments, the contacting is in vitro or in vivo. In some embodiments, the contacting is in vitro. In some embodiments, the contacting is in vivo. In some embodiments, the contacting is in vivo in a subject selected from a human, ovine, bovine, feline, canine, equine, simian, or murine. In some embodiments, the subject is a human.

In some embodiments, contacting comprises administering the compound of formula I to the subject. The compounds of the technology can be administered by admixing in an in vitro system, parenteral (e.g., intramuscular, intraperitoneal, intravenous, ICV, intracisternal injection or infusion, subcutaneous injection, or implant), oral, by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration.

Compositions

Compositions, including pharmaceutical compositions comprising the compounds described herein can be manufactured by means of conventional mixing, dissolving, granulating, dragee-making levigating, emulsifying, encapsulating, entrapping, or lyophilization processes. The compositions can be formulated in conventional manner using one or more physiologically acceptable carriers, diluents, excipients, or auxiliaries which facilitate processing of the compounds provided herein into preparations which can be used pharmaceutically.

In one embodiment, this disclosure relates to a composition comprising a compound as described herein and a carrier.

In another embodiment, this disclosure relates to a pharmaceutical composition comprising a compound as described herein and a pharmaceutically acceptable carrier.

In another embodiment, this disclosure relates to a pharmaceutical composition comprising a therapeutically effective amount of a compound as described herein and a pharmaceutically acceptable carrier.

The pharmaceutical compositions for the administration of the compounds can be conveniently presented in dosage unit form and can be prepared by any of the methods well known in the art of pharmacy. The pharmaceutical compositions can be, for example, prepared by uniformly and intimately bringing the compounds provided herein into association with a liquid carrier, a finely divided solid carrier or both, and then, if necessary, shaping the product into the desired formulation. In the pharmaceutical composition the compound provided herein is included in an amount sufficient to produce the desired therapeutic effect. For example, pharmaceutical compositions of this disclosure may take a form suitable for virtually any mode of administration, including, for example, topical, ocular, oral, buccal, systemic, nasal, injection, infusion, transdermal, rectal, and vaginal, or a form suitable for administration by inhalation or insufflation.

For topical administration, the compounds can be formulated as solutions, gels, ointments, creams, suspensions, etc., as is well-known in the art.

Systemic formulations include those designed for administration by injection (e.g., subcutaneous, intravenous, infusion, intramuscular, intrathecal, or intraperitoneal injection) as well as those designed for transdermal, transmucosal, oral, or pulmonary administration.

Useful injectable preparations include sterile suspensions, solutions, or emulsions of the compounds provided herein in aqueous or oily vehicles. The compositions may also contain formulating agents, such as suspending, stabilizing, and/or dispersing agents. The formulations for injection can be presented in unit dosage form, e.g., in ampules or in multidose containers, and may contain added preservatives.

Alternatively, the injectable formulation can be provided in powder form for reconstitution with a suitable vehicle, including but not limited to sterile pyrogen free water, buffer, and dextrose solution, before use. To this end, the compounds provided herein can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets, or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets can be coated by methods well known in the art with, for example, sugars, films, or enteric coatings.

Compositions intended for oral use can be prepared according to any method known to the art for the manufacture of pharmaceutical compositions, and such compositions may contain one or more agents selected from the group consisting of sweetening agents, flavoring agents, coloring agents, and preserving agents in order to provide pharmaceutically elegant and palatable preparations. Tablets contain the compounds provided herein in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch or alginic acid); binding agents (e.g. starch, gelatin, or acacia); and lubricating agents (e.g., magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques well known to the skilled artisan. The pharmaceutical compositions of the technology may also be in the form of oil-in-water emulsions.

Liquid preparations for oral administration may take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin, or acacia); non-aqueous vehicles (e.g., almond oil, oily esters, ethyl alcohol, Cremophore™, or fractionated vegetable oils); and preservatives (e.g., methyl or propyl-p-hydroxybenzoates or sorbic acid). The preparations may also contain buffer salts, preservatives, flavoring, coloring, and sweetening agents as appropriate.

Use of Compounds for Preparing Medicaments

The compounds and compositions of the present invention are also useful in the preparation of medicaments. The methods and techniques for preparing medicaments of a composition are known in the art. For the purpose of illustration only, pharmaceutical formulations and routes of delivery are detailed herein.

Thus, one of skill in the art would readily appreciate that any one or more of the compositions described above, including the many specific embodiments, can be used by applying standard pharmaceutical manufacturing procedures to prepare medicaments to treat the many disorders described herein. Such medicaments can be delivered to the subject by using delivery methods known in the pharmaceutical arts.

Kits

The compounds and compositions, as described herein, can be provided in kits. The kits can further contain instructions for use.

The following examples are included to demonstrate some embodiments of the disclosure. However, those of skill in the art should, in light of the present disclosure, appreciate that many changes can be made in the specific embodiments which are disclosed and still obtain a like or similar result without departing from the spirit and scope of the disclosure.

EXAMPLES

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

In addition, where features or aspects of the invention are described in terms of Markush groups, those skilled in the art will recognize that the invention is also thereby described in terms of any individual member or subgroup of members of the Markush group.

Materials and Methods $^1$H NMR spectra were recorded on an Oxford AM-400 spectrometer for solution in $CDCl_3$, $CD_3OD$ or $D_2O$. Coupling constants J are shown in Hz. $^{13}$C NMR spectra were recorded on an Oxford AM-400 spectrophotometer (100 MHz) with a complete proton decoupling spectrophotometer ($CDCl_3$: 77.0 ppm). Flash column chromatography was performed using 230-400 mesh silica gel (Sigma-Aldrich, St. Louis, MO). For thin-layer chromatography (TLC), silica gel plates (Sigma-Aldrich GF254) were used. HPLC was performed on a Waters 2487 series with a C18 Kinetex column (5 μm, 100 Å, 150×10.0 mm, from Phenomenex Inc, Torrance, CA). All other reagents were purchased from readily available commercial sources and used without further purification.

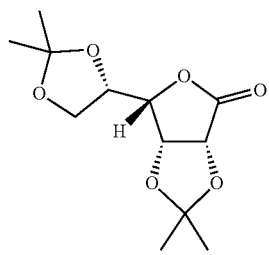

2

General procedure for the synthesis of compound 2. To a stirred solution of compound 1 (8.9 g, 50 mmol) in dry acetone (200 mL) was added CuSO$_4$ (16.0 g, 100 mmol, 2 eq) followed by the addition of concentrated H$_2$SO$_4$ (266 µL, 0.1 eq) at 0° C. Then, the reaction mixture was allowed to warm to room temperature and stirred at the same temperature for 24 hours. The pH of the solution was adjusted to 7 with NaHCO$_3$, and the resulting slurry was filtered and evaporated to give a residue. The residue was dissolved in ethyl ether (200 mL) and washed with water (3×50 mL), dried over anhydrous Na$_2$SO$_4$, filtered and concentrated to give the compound 2 (8.0 g, 62%) as a colorless oil.

(3aR,6S,6aR)-6-((S)-2,2-dimethyl-1,3-dioxolan-4-yl)-2,2-dimethyldihydrofuro[3,4-d][1,3]dioxol-4(3aH)-one (2).[1] NMR (400 MHz, CDCl$_3$): δ 1.38 (s, 3H, CH$_3$), 1.39 (s, 3H, CH$_3$), 1.466 (s, 3H, CH$_3$), 1.472 (s, 3H, CH$_3$), 3.82 (dd, 1H, J=8.8, 5.6 Hz, CH$_2$), 4.22 (dd, 1H, J=8.8, 6.0 Hz, CH$_2$), 4.40-4.47 (m, 2H, 2CH), 4.74 (dd, 1H, J=6.0, 3.2 Hz, CH), 4.83 (d, 1H, J=6.0 Hz, CH).

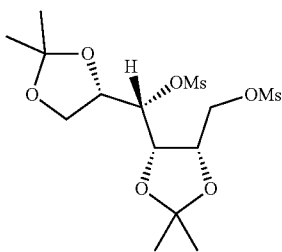

3

General procedure for the synthesis of compound 3. To a stirred solution of compound 2 (4.5 g, 17.4 mmol) in anhydrous THF (50 mL) was added LiAlH$_4$ (9.9 mL, 34.8 mmol, 2 eq, a 3.5 M solution in THF) in several portions at 0° C. Then, the reaction mixture was allowed to warm to room temperature and stirred at the same temperature for 8 hours. The reaction mixture was then quenched with ice, dried over anhydrous MgSO$_4$, filtered through a celite pad and evaporated to give a residue. The residue was dissolved in pyridine (20 mL) and the mixture was cooled to 0° C. MsCl (6.8 mL, 52.2 mmol, 3 eq) was added dropwise and the resulting mixture was then allowed to warm to room temperature. After stirring for 16 hours, the reaction was quenched with MeOH (10 mL) and the mixture was concentrated under reduced pressure to give a residue. The residue was dissolved in EtOAc (50 mL), and the organic phase was washed successively with saturated aqueous CuSO$_4$ (3×50 mL), brine (50 mL), dried over anhydrous Na$_2$SO$_4$, filtered, concentrated and purified by a flash column chromatography on silica gel to afford the compound 3 (5.8 g, 80%) as a colorless oil.

(S)-((S)-2,2-dimethyl-1,3-dioxolan-4-yl)((4S,5S)-2,2-dimethyl-5-(((methylsulfonyl)oxy)methyl)-1,3-dioxolan-4-yl)methyl methanesulfonate (3). $^1$H NMR (400 MHz, CDCl$_3$): δ 1.37 (s, 3H, CH$_3$), 1.39 (s, 3H, CH$_3$), 1.46 (s, 3H, CH$_3$), 1.52 (s, 3H, CH$_3$), 3.08 (s, 3H, CH$_3$), 3.17 (s, 3H, CH$_3$), 4.00 (dd, 1H, J=8.8, 6.8 Hz, CH$_2$), 4.15 (dd, 1H, J=8.8, 6.8 Hz, CH$_2$), 4.36-4.49 (m, 5H, CH), 4.83 (dd, 1H, J=6.8, 4.8 Hz, CH).

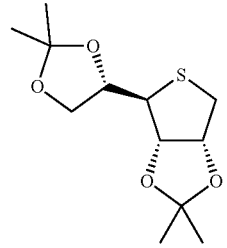

4

General procedure for the synthesis of compound 4. To a stirred solution of compound 3 (5.8 g, 13.9 mmol) in DMF (100 mL) was added sodium sulfide nonahydrate (4.0 g, 16.7 mmol, 1.2 eq) and the reaction mixture was heated to 100° C. for 18 h. After being cooled to room temperature, the mixture was diluted with ethyl ether (300 mL) and washed with water (5×50 mL) and brine (50 mL). The organic layer was dried over anhydrous Na$_2$SO$_4$, filtered, concentrated and purified by a flash column chromatography on silica gel to afford the compound 4 (2.3 g, 64%) as a colorless oil.

(3aS,4R,6aR)-4-((S)-2,2-dimethyl-1,3-dioxolan-4-yl)-2,2-dimethyltetrahydrothieno[3,4-d][1,3]dioxole (4).[1] $^1$H NMR (400 MHz, CDCl$_3$): δ 1.32 (s, 3H, CH$_3$), 1.34 (s, 3H, CH$_3$), 1.43 (s, 3H, CH$_3$), 1.51 (s, 3H, CH$_3$), 2.89 (d, 1H, J=12.8 Hz, CH$_2$), 3.09 (dt, 1H, J=12.8, 2.0 Hz, CH$_2$), 3.23 (d, 1H, J=8.8 Hz, CH), 3.76 (dd, 1H, J=8.4, 6.0 Hz, CH$_2$), 3.98 (dt, 1H, J=8.8, 6.4 Hz, CH), 4.15 (dd, 1H, J=8.8, 6.4 Hz, CH$_2$), 4.92 (d, 2H, J=2.0 Hz, 2CH).

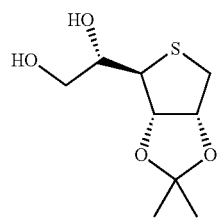

5

General procedure for the synthesis of compound 5. Compound 4 (2.1 g, 8.0 mmol) was dissolved in 30% aqueous AcOH (60 mL) and the resulting mixture was stirred at room temperature for 6 h. The reaction was then concentrated under reduced pressure to give a residue. The residue was purified by a flash column chromatography on silica gel to afford the compound 5 (599 mg, 34%) as a colorless oil.

(S)-1-((3aS,4R,6aR)-2,2-dimethyltetrahydrothieno[3,4-d][1,3]dioxol-4-yl)ethane-1,2-diol (5).[1] $^1$H NMR (400 MHz, CDCl$_3$): δ 1.33 (s, 3H, CH$_3$), 1.53 (s, 3H, CH$_3$), 2.94 (dd, 1H, J=12.4, 2.0 Hz, CH$_2$), 3.09 (dt, 1H, J=12.4, 4.8 Hz, CH$_2$), 3.32 (dd, 1H, J=6.8, 2.4 Hz, CH), 3.64-3.72 (m, 2H, CH$_2$+CH), 3.82 (dd, 1H, J=10.4, 3.6 Hz, CH$_2$), 4.89-4.96 (m, 2H, 2CH).

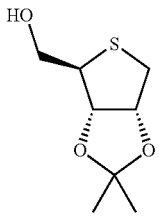

6

General procedure for the synthesis of compound 6. To a stirred solution of compound 5 (1.1 g, 5.0 mmol) in ethyl acetate (25 mL) was added Pb(OAc)$_4$ (2.4 g, 5.5 mmol, 1.1 eq) at 0° C. and the reaction mixture was stirred at same temperature for 20 min. The reaction mixture was filtered, the filtrate was diluted with EtOAc (100 mL) and washed with saturated aqueous NaHCO$_3$ solution (3×20 mL), water (20 mL) and brine (15 mL). The organic layer was dried over anhydrous Na$_2$SO$_4$, filtered, concentrated to give a residue. The residue was dissolved in MeOH (20 mL) and NaBH$_4$ (246 mg, 6.5 mmol, 1.3 eq) was added carefully in several portions. The resulting mixture was stirred for 30 min at the same temperature and neutralized with glacial AcOH (1 mL). The mixture was diluted with ethyl ether (200 mL) and washed with water (3×20 mL) and brine (20 mL). The organic layer was dried over anhydrous Na$_2$SO$_4$, filtered, concentrated and purified by a flash column chromatography on silica gel to afford the compound 6 (580 mg, 61%) as a colorless oil.

((3aS,4R,6aR)-2,2-dimethyltetrahydrothieno[3,4-d][1,3]dioxol-4-yl)methanol (6).[1] $^1$H NMR (400 MHz, CDCl$_3$): δ 1.30 (s, 3H, CH$_3$), 1.50 (s, 3H, CH$_3$), 2.88 (d, 1H, J=12.8 Hz, CH$_2$), 3.07 (dd, 1H, J=12.8, 3.6 Hz, CH$_2$), 3.40-3.45 (m, 1H, CH), 3.50-3.62 (m, 2H, CH$_2$), 4.70 (d, 1H, J=5.6 Hz, CH$_2$), 4.89 (t, 1H, J=4.8 Hz, CH).

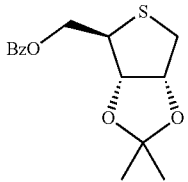

7

General procedure for the synthesis of compound 7. To a stirred solution of compound 6 (570 mg, 3.0 mmol) in a mixture of anhydrous DCM (15 mL) and pyridine (15 mL) was added BzCl (523 μL, 4.5 mmol, 1.5 eq) at 0° C. Then, the reaction mixture was allowed to warm to room temperature. After stirring for 14 hours, the reaction was quenched with MeOH (2 mL) and the mixture was concentrated under reduced pressure to give a residue. The residue was dissolved in EtOAc (80 mL), and the organic phase was washed successively with saturated aqueous CuSO$_4$ (3×20 mL), brine (20 mL), dried over anhydrous Na$_2$SO$_4$, filtered, concentrated and purified by a flash column chromatography on silica gel to afford the compound 7 (645 mg, 73%) as a colorless oil.

((3aS,4R,6aR)-2,2-dimethyltetrahydrothieno[3,4-d][1,3]dioxol-4-yl)methyl benzoate (7).[1] $^1$H NMR (400 MHz, CDCl$_3$): δ 1.33 (s, 3H, CH$_3$), 1.54 (s, 3H, CH$_3$), 2.97 (dd, 1H, J=12.8, 1.6 Hz, CH$_2$), 3.18 (dd, 1H, J=12.8, 4.8 Hz, CH$_2$), 3.62-3.66 (m, 1H, CH), 4.32 (dd, 1H, J=11.6, 8.0 Hz, CH$_2$), 4.42 (dd, 1H, J=11.6, 6.0 Hz, CH$_2$), 4.80 (dd, 1H, J=6.0, 1.6 Hz, CH), 4.97-5.00 (m, 1H, CH), 7.44-7.48 (m, 2H, ArH), 7.56-7.61 (m, 1H, ArH), 8.03-8.05 (m, 2H, ArH).

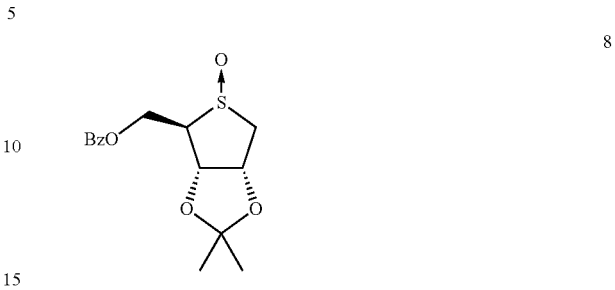

8

General procedure for the synthesis of compound 8. To a stirred solution of compound 7 (589 mg, 2.0 mmol) in anhydrous DCM (15 mL) was added m-CPBA (380 mg, 2.2 mmol, 1.1 eq) in several portions at −78° C. and the resulting mixture was stirred at the same temperature for 2 h. Then, the reaction was quenched with saturated aqueous NaHCO$_3$ (15 mL) and extracted with DCM (3×20 mL). The combined organic layers were washed with brine (20 mL), dried over anhydrous Na$_2$SO$_4$, filtered, concentrated and purified by a flash column chromatography on silica gel to afford the compound 8 (341 mg, 55%) as a colorless oil.

Compound 8.[1] $^1$H NMR (400 MHz, CDCl$_3$): δ 1.35 (s, 3H, CH$_3$), 1.52 (s, 3H, CH$_3$), 3.25 (dd, 1H, J=14.4, 4.0 Hz, CH$_2$), 3.40 (dd, 1H, J=14.4, 6.0 Hz, CH$_2$), 3.49 (dt, 1H, J=8.8, 5.2 Hz, CH), 4.75 (dd, 1H, J=12.0, 8.8 Hz, CH$_2$), 4.91 (dd, 1H, J=12.0, 4.8 Hz, CH$_2$), 5.05 (t, 1H, J=6.0 Hz, CH), 5.27 (dt, 1H, J=4.0, 6.0 Hz, CH), 7.44-7.47 (m, 2H, ArH), 7.56-7.61 (m, 1H, ArH), 8.03-8.06 (m, 21-1, ArH).

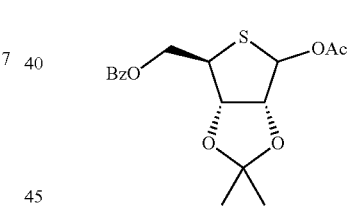

9

General procedure for the synthesis of compound 9. Compound 8 (310 mg, 1.0 mmol) was dissolved in AcOH (10 mL) and the mixture was heated to 100° C. for 8 h. Then, the reaction was concentrated to give a residue. The residue was dissolved in EtOAc (80 mL), and the organic phase was washed successively with saturated aqueous NaHCO$_3$ (3×10 mL), brine (20 mL), dried over anhydrous Na$_2$SO$_4$, filtered, concentrated and purified by a flash column chromatography on silica gel to afford the compound 9 (190 mg, 54%) as a colorless oil.

((3aS,4R,6aR)-6-acetoxy-2,2-dimethyltetrahydrothieno[3,4-d][1,3]dioxol-4-yl)methyl benzoate (9).[1] $^1$H NMR (400 MHz, CDCl$_3$) of one isomer: δ 1.32 (s, 3H, CH$_3$), 1.53 (s, 3H, CH$_3$), 3.79 (dd, 1H, J=9.6, 6.0 Hz, CH), 4.38 (dd, 1H, J=12.0, 9.6 Hz, CH$_2$), 4.45 (dd, 1H, J=12.0, 6.0 Hz, CH$_2$), 4.95 (d, 1H, J=4.8 Hz, CH$_2$), 5.01 (d, 1H, J=4.8 Hz, CH), 6.08 (s, 1H, CH), 7.47 (t, 2H, J=8.0 Hz, ArH), 7.57-7.61 (m, 1H, ArH), 8.06-8.09 (m, 2H, ArH).

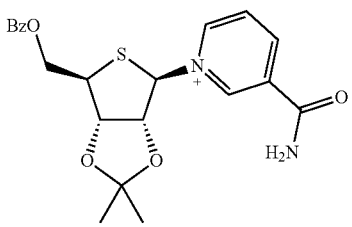

General procedure for the synthesis of compound 3. Compound 9[1] (106 mg, 0.3 mmol) was dissolved in toluene (10 mL) and cooled to 0° C. HBr (33% (wt) in acetic acid) (110 mg, 0.45 mmol, 1.5 eq) was added dropwise and the reaction was stirred at 0° C. for 5 hours. After the starting material was consumed, the reaction was concentrated under reduced pressure to give a residue. The residue was azeotroped with toluene (3×20 mL) to remove remaining acetic acid and dried in vacuo. The crude product and nicotinamide (44 mg, 0.36 mmol, 1.2 eq) was dissolved in $CH_3CN$ (10 mL). The reaction was stirred under Ar gas at room temperature for 24 hours. The reaction was concentrated in vacuo (the temperature was kept below 35° C.) and purified by a flash column chromatography on silica gel to afford the desired compound 10 (86 mg, 58% yield) as a colorless solid.

1-((3aR,4R,6R,6aS)-6-((benzoyloxy)methyl)-2,2-dimethyltetrahydrothieno[3,4-d][1,3]dioxol-4-yl)-3-carbamoylpyridin-1-ium bromide (10). $^1$H NMR (400 MHz, $CD_3OD$): δ 1.45 (s, 3H, $CH_3$), 1.67 (s, 3H, $CH_3$), 4.31 (t, 1H, J=4.4 Hz, CH), 4.57 (dd, 1H, J=12.0, 4.4 Hz, $CH_2$), 4.75 (dd, 1H, J=12.0, 4.4 Hz, $CH_2$), 5.22 (dd, 1H, J=4.8, 0.8 Hz, CH), 5.46 (d, 1H, J=4.8 Hz, CH), 6.51 (s, 1H, CH), 7.36 (t, 2H, J=8.0 Hz, ArH), 7.55-7.59 (m, 1H, ArH), 7.65-7.67 (m, 2H, ArH), 8.03 (t, 1H, J=6.8 Hz, ArH), 8.70 (d, 1H, J=8.0 Hz, ArH), 9.44 (d, 1H, J=6.8 Hz, ArH), 9.70 (s, 1H, ArH); $^{13}$C NMR (100 MHz, $CD_3OD$): δ 23.8, 26.0, 54.4, 66.4, 86.2, 86.6, 92.6, 112.9, 127.9, 128.4, 128.8, 129.3, 133.2, 133.8, 142.7, 144.1, 144.4, 163.0, 165.8.

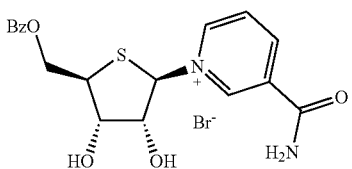

General procedure for the synthesis of compound 11. Compound 10 (50 mg, 0.1 mmol) was dissolved in a mixture of TFA/H2O (9/1, 15 mL) at 0° C. and the resulting mixture was stirred at the same temperature until the reaction complete (monitoring by TLC). The reaction was concentrated under reduced pressure and the crude product was dissolved in MeOH (0.3 mL). Addition of ethyl ether (20 mL) resulted in ppt of the desired product. The procedure was repeated four times to yield the desired product 11 (35 mg, 76%) as a colorless solid.

1-((2R,3R,4S,5R)-5-((benzoyloxy)methyl)-3,4-dihydroxytetrahydrothiophen-2-yl)-3-carbamoylpyridin-1-ium bromide (11). $^1$H NMR (400 MHz, $CD_3OD$): δ 3.92 (td, 1H, J=6.8, 2.8 Hz, CH), 4.43 (t, 1H, J=3.2 Hz, CH), 4.52 (dd, 1H, J=6.8, 3.2 Hz, CH), 4.74 (d, 2H, J=6.8 Hz, $CH_2$), 6.23 (d, 1H, J=6.8 Hz, CH), 7.51 (t, 2H, J=8.0 Hz, ArH), 7.63-7.67 (m, 1H, ArH), 8.05-8.07 (m, 2H, ArH), 8.21 (dd, 1H, J=8.0, 6.4 Hz, ArH), 9.03 (d, 1H, J=8.0 Hz, ArH), 9.46 (d, 1H, J=6.4 Hz, ArH), 9.68 (s, 1H, ArH); $^{13}$C NMR (100 MHz, $CD_3OD$): δ 51.5, 65.1, 73.9, 80.4, 81.4, 128.0, 128.4, 129.2, 129.4, 133.3, 134.5, 143.6, 144.9, 145.1, 163.4, 166.2.

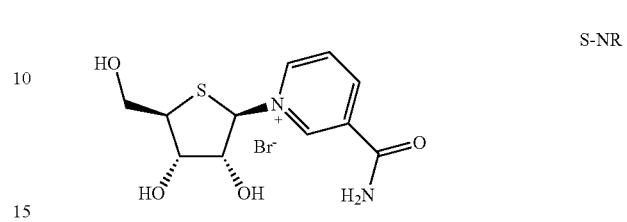

General procedure for the synthesis of S—NR. Compound 11 (23 mg, 0.05 mmol) was dissolved in ammonia (5 mL, 7 N in MeOH) and the reaction was stirred at 0° C. for 48 hours. The reaction was concentrated under reduced pressure and the crude product was dissolved in MeOH (0.2 mL). Addition of ethyl ether (20 mL) resulted in ppt of the desired product. The procedure was repeated five times to yield the desired product S—NR (11 mg, 64%) as a colorless solid.

3-carbamoyl-1-((2R,3R,4S,5R)-3,4-dihydroxy-5-(hydroxymethyl)tetrahydrothiophen-2-yl)pyridin-1-ium (S—NR). $^1$H NMR (400 MHz, $D_2O$): δ 3.67-3.70 (m, 1H, CH), 3.92-4.01 (m, 2H, $CH_2$), 4.38 (t, 1H, J=3.6 Hz, CH), 4.62 (dd, 1H, J=5.6, 3.6 Hz, CH), 6.19 (d, 1H, J=5.6 Hz, CH), 8.26 (dd, 1H, J=8.0, 6.4 Hz, ArH), 8.97 (dt, 1H, J=8.0, 1.2 Hz, ArH), 9.45 (dt, 1H, J=6.4, 1.2 Hz, ArH), 9.78 (t, 1H, J=1.2 Hz, ArH); $^{13}$C NMR (100 MHz, $D_2O$): δ 53.9, 61.5, 73.8, 80.6, 80.9, 128.4, 134.1, 143.2, 145.4, 145.5, 165.6; HRMS (ESI) for $C_{11}H_{15}N_2O_4S^+$ (M)$^+$ Calcd.: 271.0763 Da; Obs: 271.0753 Da.

Enzymatic Conversion of S—NR to S-NAD$^+$.

Human nicotinamide riboside kinase 1 (NRK1) and nicotinamide mononucleotide adenylyltransferase 1 (NMNAT1) were expressed and purified based on previous publications.[2,3]

TABLE S1

List of primer sequences used for molecular cloning of human NRK1 and NMNAT1. Restriction enzyme sites for NcoI and XhoI are underlined and in italics.

| Name | Sequence |
| --- | --- |
| NRK1-Fw | 5'-*CCATGG*ATGAAAACATTTATCATTGGAATCAGTGG-3' (SEQ ID NO: 1) |
| NRK1-Rv | 5'-*CTCGAG*TGCTGTCACTTGCAAACACTTTTG-3' (SEQ ID NO: 2) |
| NMNAT1-Fw | 5'-*CCATGG*ATGCACCACCACCACCACCACGAAAATTCCGAGAAGACTGAAGTG-3' (SEQ ID NO: 3) |
| NMNAT1-Rv | 5'-*CTCGAG*CTACTACTATGTCTTAGCTTCTGCAGTGTTTC-3' (SEQ ID NO: 4) |

Protein sequences of human NRK1 and NMNAT1:

NRK1
(SEQ ID NO: 5)
MKRFVIGIGGVTNGGKTTLAKSLQKHLPNCSVISQDDFFKPESEIDIDE

NGFLQYDVLEALNMEKMMSAVSCWMENPGSSAGPAALESAQGVPILIIE

GFLLFNYKPLDTIWNRSYFLTVPYEECKRRRSTRVYEPPDPPGYFDGHV

WPMYLKHRQEMSSITWDIVYLDGTRSEEDLFSQVYEDVKQELEKQNGLH

HHHHH

NMNAT1
(SEQ ID NO: 6)
MENSEKTEVVLLACGSFNPITNIVIHLRLFELAKDYMNGTGRYTVVKGI

ISPVGDAYKKKGLIPAYHRVIMAELATKNSKWVEVDTWESLQKEWKETL

KVLRHHQEKLEASDCDHQQNSPTLERPGRKRKWTETQDSSQKKSLEPKT

KAVPKVKLLCGADLLESFAVPNLWKSEDITQIVANYGLICVTRAGNDAQ

KFIYESDVLWKHRSNIHVVNEWIANDISSTKIRRALRRGQSIRYLVPDL

VQEYIEKHNLYSSESEDRNAGVILAPLQRNTAEAKTHHHHHH

Molecular Cloning and Protein Expression and Purification. The open reading frames (ORFs) of human NRK1 (528 bp) and NMNAT1 (840 bp) with N-terminal $His_6$-tags (SEQ ID NO: 10) were amplified through polymerase chain reaction (PCR) using primers of NRK1-Fw/Rv and NMNAT1-Fw/Rv, respectively (Table S1), which contained NcoI and XhoI restriction enzyme sites at 5'- and 3'-end, respectively. The amplified DNA fragments were digested by NcoI and XhoI restriction enzymes and then ligated into pET-28a (+) using T4 DNA ligase (New England Biolabs, Ipswich, MA). All generated expression vectors were confirmed by DNA sequencing provided by Genewiz LLC (South Plainfield, NJ).

BL21 (DE3) cells were transformed with the generated constructs for bacterial protein expression in LB Broth supplemented with kanamycin (50 μg mL$^{-1}$). The overnight bacterial culture (5 mL) was diluted into 1 liter of LB Broth with kanamycin (50 μg mL$^{-1}$) for growth at 37° C. in an incubator shaker at a speed of 250 rpm (Series 25, New Brunswick Scientific, NJ). When $OD_{600\,nm}$ reached 0.6-0.8, protein expression was induced with 0.5 mM isopropyl β-D-1-thiogalactopyranoside (IPTG) for overnight at 18° C. Cells were then harvested by centrifugation at 4,550 g (Beckman J6B Centrifuge, JS-4.2 rotor), resuspended in equilibrium buffer (20 mM Tris-HCl, pH 8.0, 200 mM NaCl, 20 mM imidazole), and lysed using a French Press (Glen-Mills, NJ) at 25,000 psi for three cycles. Cell debris was removed by centrifugation at 14,000 g for 1 hour (Beckman Coulter centrifuge, JA-17 rotor) and supernatants were filtered through 0.45 μm membranes. The filtrate was loaded on a gravity flow column packed with 1 mL Ni-NTA agarose resin (Thermo Fisher Scientific, Waltham, MA), followed by washing with 15 column volumes of wash buffer (20 mM Tris-HCl, pH 8.0, 200 mM NaCl, 30 mM imidazole). Proteins were then eluted in 15 column volumes of elution buffer (20 mM Tris-HCl, pH 8.0, 200 mM NaCl, 400 mM imidazole), dialyzed in storage buffer (20 mM Tris-HCl, pH 8.0, 300 mM NaCl, 1 mM DTT, 10% glycerol) at 4° C. for overnight and another 6 hours in fresh storage buffer, and concentrated using Amicon centrifugal concentrators (EMD Millipore, Temecula, CA) with 10 kDa cut-off. Purified proteins were examined by SDS-PAGE and a NanoDrop 2000C spectrophotometer (Thermo Fisher Scientific, Waltham, MA), and aliquoted and flash-frozen in liquid nitrogen for storage at −80° C. Calculated molecular extinction coefficient values are 1.537 for NRK1-6×His and 1.592 for NMNAT1-6×His.

Purified S—NR (0.5 mg in the form of bromide salt) was incubated with 6 mM ATP, 5 uM of purified NRK1 and NMNAT1 at the final concentration of 2 mM at room temperature for overnight in the reaction buffer (50 mM Tris, 100 mM NaCl, 12 mM $MgCl_2$, 1 mM DTT, and pH 7.5). After centrifugation at 4,000 g for 5 minutes, supernatants were analyzed by HPLC and the fraction containing S-NAD$^+$ (0.68 mg, 70%) were pooled and confirmed by both NMR and mass spectrometry. All analysis and purifications on HPLC were performed with a semipreparative C18 Kinetex column (5 μm, 100 Å, 150×10.0 mm, from Phenomenex Inc, Torrance, CA) using the following method, mobile phase A: 0.1% formic acid (aq); mobile phase B: 0.1% formic acid in methanol; flow rate: 2.0 ml/min; 0-2 min: 0-4% B, 2-4 min: 4-10% B; 4-6 min: 10-20% B; 6-9 min: 20% B; 9-12 min: 20-50% B; and 12-14 min: 50-0% B.

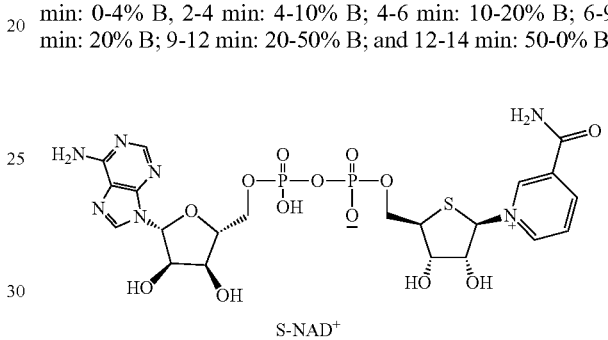

S-NAD$^+$

S-NAD$^+$. $^1$H NMR (400 MHz, $D_2O$): δ 3.76-3.79 (m, 1H, CH), 4.22-4.40 (m, 5H, $2CH_2$+CH), 4.48 (t, 1H, J=3.2 Hz, CH), 4.51-4.54 (m, 1H, CH), 4.68 (dd, 1H, J=6.4, 3.6 Hz, CH), 4.75 (t, 1H, J=5.2 Hz, ArH), 6.13-6.15 (m, 2H, 2CH), 8.26 (dd, 1H, J=8.0, 6.4 Hz, ArH), 8.41 (s, 1H, ArH), 8.62 (s, 1H, ArH), 8.92 (d, 1H, J=8.0 Hz, ArH), 9.55 (d, 1H, J=6.4 Hz, ArH), 9.60 (s, 1H, ArH); $^{13}$C NMR (100 MHz, $D_2O$): δ 52.6 (d, J=8.0 Hz), 65.0-65.1 (m), 65.9-66.1 (m), 70.2, 74.5, 74.9, 81.0, 81.2, 84.0 (d, J=8.9 Hz), 87.7, 128.7, 133.9, 142.2, 142.8, 145.2, 145.4, 145.8, 150.2, 165.4; FIRMS (ESI) for $C_{21}H_{27}N_7O_{13}P_2SNa^+$ (M+Na)$^+$: Calcd.: 702.0766 Da; Obs: 702.0760 Da.

Expression and Purification of Recombinant Human CD38.

Synthetic DNA encoding extracellular domain of human CD38 (R45-I300) was purchased from Integrated DNA Technologies, Inc. (Coralville, Iowa), in which four asparagine residues were mutated to eliminate N-glycosylation. Below is the amino acid sequence of human CD38 used for expression and purification: RWRQQWSGPGTTKRF-PETVLARCVKYTEIHPEMRHVDCQSVWDAFK-GAFISKHPCD ITEEDYQPLMKLGTQTVPCNKILL-WSRIKDLAHQFTQVQRDMFTLEDTLLGYLADDL TWCGE-FATSKINYQSCPDWRKDCSNNPVSVFWKTVSRR-FAEAACDVVHVMLDGSR SKIFDKDSTFGSVE VHNLQPEKVQTLEAWVIHGGREDSRDLCQDPTIKE-LESIISKRNI QFSCKNIYRPDKFLQCVKNPEDSSCTSEI (SEQ ID NO: 7).[4] An N-terminal $His_6$-tag (SEQ ID NO: 10) followed by a TEV protease cleave site was placed in front of the gene encoding human CD38. The designed insert was amplified by PCR using primers (1) 5'-AGTCTTGCACTTGTCACGAATTCGCATCATCAC-3' (SEQ ID NO: 8) and (2) 5'-ATGTCTGGCCAGCTAGCACTTATCAG-3' (SEQ ID NO: 9), followed by enzymatic digestion using NheI and EcoRI (New England Biolabs, Ipswich, MA), and ligation into pFuse mammalian expression vector using T4 DNA ligase (New England Biolabs, Ipswich, MA). The expression vector expressing human CD38 was confirmed by DNA sequencing provided by Genewiz LLC (South Plainfield, NJ).

Recombinant CD38 was expressed in Expi293 expression system (Thermo Scientific, MA) through transient transfection by following manufacturer's instruction. Culture media of Expi293 cells containing secreted recombinant human CD38 were collected 4 days post transfection. Expressed human CD38 was purified by Ni-NTA affinity chromatography by following the same procedures as described above for purification of human NRK1 and NMNAT1. The N terminal poly-histidine tag was removed by incubating purified CD38 with TEV protease (Thermo Scientific, MA) at 30° C. for 4 hours, followed by passing through a Ni-NTA column to collect $His_6$-tag-free CD38 ("$His_6$" disclosed as SEQ ID NO: 10). Purified CD38 was then dialyzed against storage buffer (25 mM HEPES, 250 mM NaCl, pH 7.5) overnight at 4° C. and another 6 hours in fresh storage buffer, and concentrated using Amicon centrifugal concentrators (EMD Millipore, Temecula, CA) with 10 kDa cut-off. Purified human CD38 was examined by SDS-PAGE and a NanoDrop 2000C spectrophotometer (Thermo Fisher Scientific, Waltham, MA), and aliquoted and flash-frozen in liquid nitrogen for storage at −80° C. The calculated molecular extinction coefficient is 1.756 for human CD38. For crystallization, $His_6$-tag-free CD38 ("$His_6$" disclosed as SEQ ID NO: 10) was further purified by gel filtration chromatography using Superdex 75 Increase 10/300 GL (GE Healthcare Life Sciences, Pittsburgh, PA) in 15 mM HEPES pH 7.0 and 50 mM NaCl. Fractions with CD38 were pooled and concentrated using Amicon centrifugal concentrators with 10 kDa cut-off.

CD38 Kinetic Studies with Nicotinamide Guanine Dinucleotide ($NGD^+$) as the Substrate.

$NGD^+$ (Sigma-Aldrich, MO) was used as a substrate to determine ADP-ribosyl cyclase activity of purified CD38, because cyclic GDP-ribose (cGDPR) product is characterized by distinctive UV absorbance at 295 nm and fluorescence emission at 410 nm (excitation at 300 nm).[5] To characterize kinetic parameters, reactions were initiated by additions of recombinant CD38 (8.3 nM final) into assay wells with various concentrations of $NGD^+$ in 20 mM MES, pH 6.5, followed by monitoring the reactions through fluorescence at 410 nm (excitation at 300 nm) to determine initial reaction rates. Inhibition activities of $S-NAD^+$ were determined by carried out enzymatic formation of cyclic GDP-ribose in the presence of $S-NAD^+$. Reactions were initiated by additions of recombinant CD38 (8.3 nM final) into assay wells with 50 uM of NGD and various concentrations of $S-NAD^+$ in 20 mM MES, pH 6.5. All reactions were carried out in black 96-well plates and the resulting fluorescence was measured using a BioTek Synergy H1 Hybrid Multi-Mode Microplate Reader (BioTek, VT) in the kinetic mode. The $K_m$ of $NGD^+$ for CD38 was calculated by fitting data with Michaelis-Menten function implemented in GraphPad Prism (La Jolla, CA). The inhibition constant ($K_i$) of $NGD^+$ was determined by fitting the initial reaction rates and inhibitor concentrations to the expression for competitive inhibition: $(V'_0/V_0)=(K_m+[S])/(K_m+[S]+(K_m[I]/K_i))$, where $V'_0$ is the initial reaction rate in the presence of inhibitor, $V_0$ is the initial reaction rate in the absence of inhibitor, [S] is the substrate concentration, and [I] is the inhibitor concentration.

Substrate Activity of $S-NAD+$ for Human CD38.

1 mM $S-NAD^+$ and $NAD^+$ in 50 mM MES, pH 6.5 were incubated with 13.4 nM recombinant human CD38 for overnight at room temperature, followed HPLC analysis of the reaction mixtures. HPLC analysis was performed with a semipreparative C18 Kinetex column (5 μm, 100 Å, 150× 10.0 mm, from Phenomenex Inc, Torrance, CA) using following method: mobile phase A: 0.1% formic acid (aq); mobile phase B: 0.1% formic acid in methanol; flow rate: 2.0 ml/min; 0-2 min: 0-4% B, 2-4 min: 4-10% B; 4-6 min: 10-20% B; 6-9 min: 20% B; 9-12 min: 20-50% B; and 12-14 min: 50-0% B.

Substrate Activities of $S-NAD^+$ with Redox Enzymes.

Bovine glutamate dehydrogenase (GDH) and *Leuconostoc mesenteroides* glucose-6-phosphate dehydrogenase (G6PDH) were purchased from Sigma-Aldrich (St. Louis, MO) and used for determining the substrate activities of $NAD^+$ and $S-NAD^+$. To examine substrate activity with bovine GDH, 0.1 mM $NAD^+$ or $S-NAD^+$ was incubated with 1 mM L-glutamate and 0.1 unit/ml GDH in buffer containing 2 mM DTT, 50 mM Tris, pH 7.5 for 15 minutes at room temperature. To determine substrate activity with G6PDH, 0.5 mM $NAD^+$ or $S-NAD^+$ was incubated with 5 mM D-glucose 6-phosphate and 0.01 unit/ml G6PDH in buffer containing 5 mM $MgCl_2$, 50 mM Tris, pH 7.5 for 15 minutes at room temperature. Formation of NADH and S-NADH were monitored by UV absorbance at 340 nm under kinetic mode using a NanoDrop 2000C spectrophotometer (Thermo Scientific, MA).

HPLC Analysis of Reduction of $NAD^+$ and $S-NAD^+$ by Redox Enzymes.

To examine the bovine GDH-catalyzed reactions, 0.5 mM $NAD^+$ or $S-NAD^+$ was incubated with 2 mM L-glutamate and 20 unit/ml GDH in buffer containing 2 mM DTT, 50 mM Tris, pH 7.5 for 30 minutes at room temperature, followed by HPLC analysis with detection of UV absorbance at 340 nm. To evaluate the *L. mesenteroides* G6PDH-catalyzed reactions, 0.5 mM $NAD^+$ or $S-NAD^+$ was incubated with 5 mM D-glucose 6-phosphate and 10 unit/ml G6PDH in buffer containing 5 mM $MgCl_2$, 50 mM Tris, pH 7.5 for 30 minutes at room temperature, followed by HPLC analysis with detection of UV absorbance at 340 nm. The HPLC method used for analysis of reactions by GDH and G6PDH was the same as described above.

X-Ray Crystallographic Study of $S-NAD^+$ with Human CD38.

Crystallization was performed using a vapor diffusion method in a hanging-drop manner with a 1:1 ratio of 1 μL of reservoir solution and 1 μL of protein-ligand solution. The initial crystals grew under the previously published conditions.[6,7] To prepare the Protein-Ligand complex, 18.5 μl of 0.1 mM protein in 15 mM HEPES, pH 7.0, 50 mM NaCl was mixed with 1.5 μl of 69 mM ligand in the same buffer. This produced a mixture of the protein:ligand close to 1:50 molar ratio at their final concentration. The complex was incubated on ice for 30 minutes before crystallization. Single crystals appeared after 5 days and grew to their maximum size within 10-40 days. The best crystals grew in 100 mM HEPES, pH 7.0, 14-18% PEG 4000 at 22° C. Crystals were dipped into a 10% glycerol cryosolution and were flash-frozen in liquid nitrogen before they were mounted for data collection.

X-Ray Diffraction Data Collection and Structure Determination.

Data was collected at Synchrotron Radiation Light Source (SSRL) using beamline 12-2 equipped with a Dectris-Pilatus 6M detector. The collected data were indexed and integrated with XDS and scaled using Scala, a part of the CCP4 suite.[8-10] Initial phase information was obtained by molecular replacement using PHASER with the previously solved structure of human cyclic-ADP-ribosyl synthetase/NAD+ glycohydrolase (PDB ID code 1ZVM) as the search model.[11] Waters were added using ArpWarp during the initial round of the refinement.[12-14] The Ligand was built using Ligand Builder in Coot and restrain generation and optimization by elbow part of Phenix Crystallography suit and also ProDrg part of CCP4 suit.[9,14-16] The structure was improved by iterative rounds of model building and refinement using the programs Coot and Refmac5.[13,14] The crystals belong to space group P1 2$_1$1 and it contains two molecules per asymmetric unit. Crystallographic details and statistics are listed in Table S2.

TABLE S2

Cyrstallographic statistics for the S-NAD+ with human CD38.

| Data collection[a] | |
|---|---|
| Wavelength (Å) | 0.97946 |
| Space group | P 1 2$_1$ 1 |
| Unit cell dimensions | a = 57.74 |
| [a, b, c (Å)] | b = 51.11 |
|  | c = 100.67 |
| Resolution range (Å) | 29.31-2.40 |
| Highest resolution shell (Å) | 2.53-2.40 |
| No. of observed reflections | 202072 |
| No. of unique reflections | 23158 |
| Multiplicity | 8.7 (8.7) |
| Completeness (%) | 99.9 (99.9) |
| <I/σI> | 6.0 (1.3) |
| $R_{merge}$ (%) | 36.8 (146.8) |
| $R_{pim}$ (%) | 13.3 (52.5) |
| $CC_{1/2}$ (%) | 96.1 (73.6) |
| Wilson B-factor | 48.5 |
| Refinement | |
| $R_{work}$ (%) | 21.57 |
| $R_{free}$ (%) | 26.17 |
| No. atoms | |
| Macromolecules | 3908 |
| Ligand | 88 |
| Water | 87 |
| B-factor (Å$^2$) | |
| Macromolecule | A: 48.1 |
|  | B: 54.3 |
| Solvent | C: 42.3 |
| R.m.s deviations | |
| Bond lengths (Å) | 0.01 |
| Bond angles (deg) | 1.42 |
| Ramachandran statistics (%) | |
| Favored | 97.15 |
| Outliers | 0.20 |
| Molprobity score | 1.03 |
| PDB ID | 6EDR |

[a]Values in parentheses are for the highest-resolution shell.

Results and Discussion

Figures 12A, 12B, 12C:
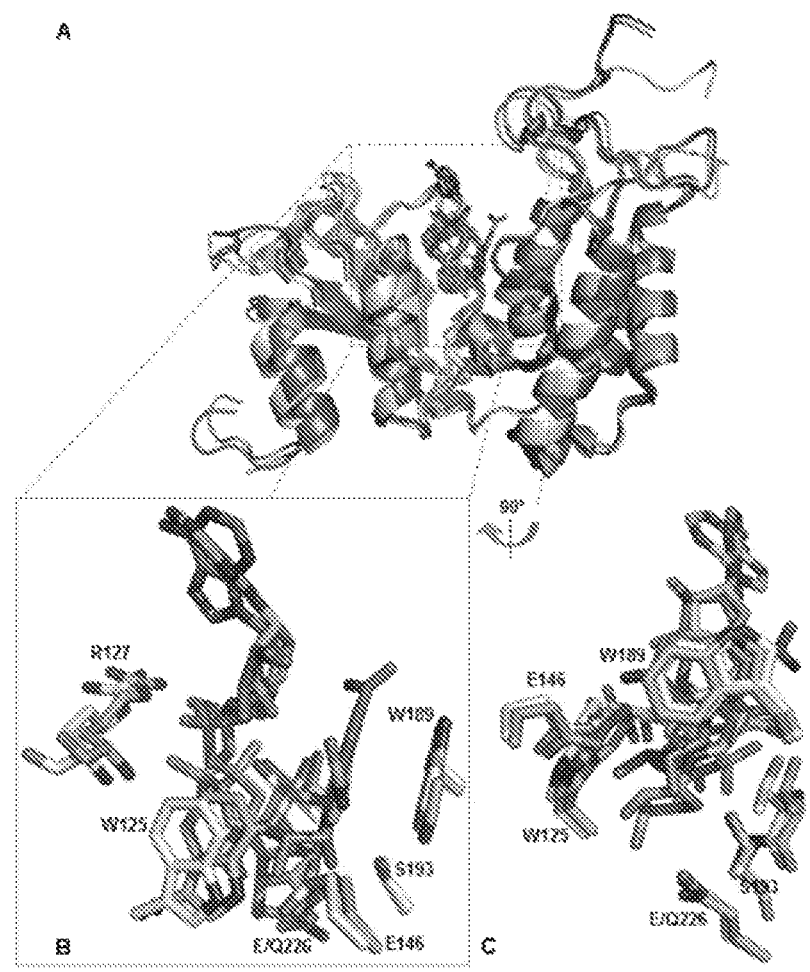
FIGS. 12A-12C: Structural comparison of $S-NAD^+$-bound CD38 with $NAD^+$-bound CD38 and apo-CD38.

Considering the chemical structure of NAD+, Applicant envisioned that replacing the endocyclic oxygen with sulfur can possibly generate a stable analogue more closely mimicking NAD+ in geometry and electrostatics. Furthermore, inspired by nicotinamide riboside (NR) kinase (NRK)– and nicotinamide mononucleotide adenylyltransferase (NMNAT)-mediated biosynthesis of NAD+ from its NR precursor, Applicant hypothesized that S—NR may be enzymatically converted to S-NAD+ in high efficiency by human NRK and NMNAT enzymes (FIG. 12A). The human genome encodes two NRK isoforms (NRK1 and 2) and three NMNAT isoforms (NMNAT1-3). Previous studies indicated that human NRK1 and NMNAT1 exhibit adequate catalytic activities for NR+ adenosine triphosphate (ATP) and nicotinamide mononucleotide (NMN)+ ATP, respectively, and promiscuity towards other substrate analogues.[40-42] In contrast to total chemical synthesis of NAD+ analogues which has proven challenging due to synthetic complexity and low yields for the difficult pyrophosphate coupling, using recombinant NRK and NMNAT may afford a facile and efficient approach for the generation of stable NAD+ mimics.

Figure 18:
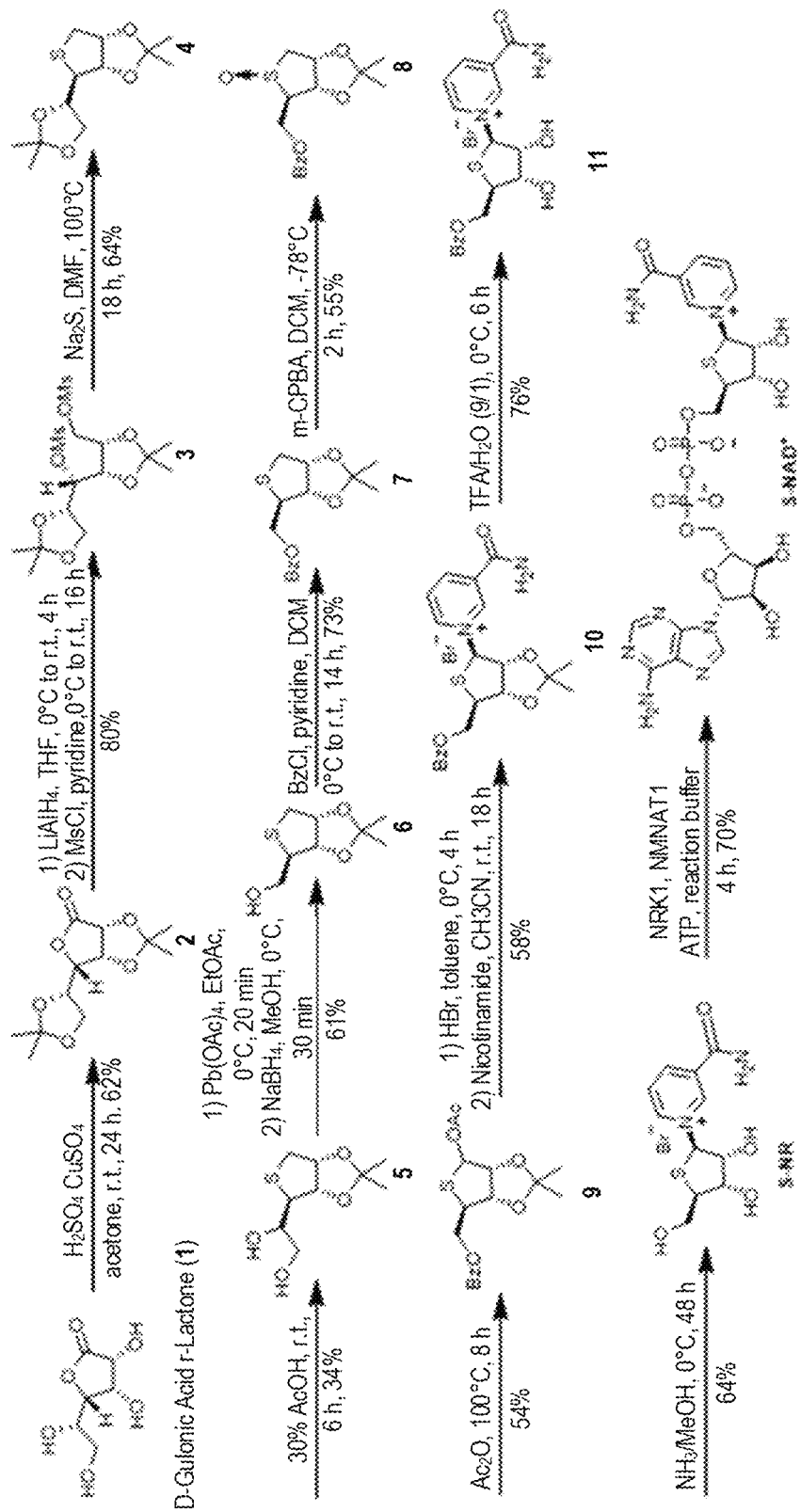
FIG. 18: Chemoenzymatic synthesis of $S-NAD^+$.
Figure 19:
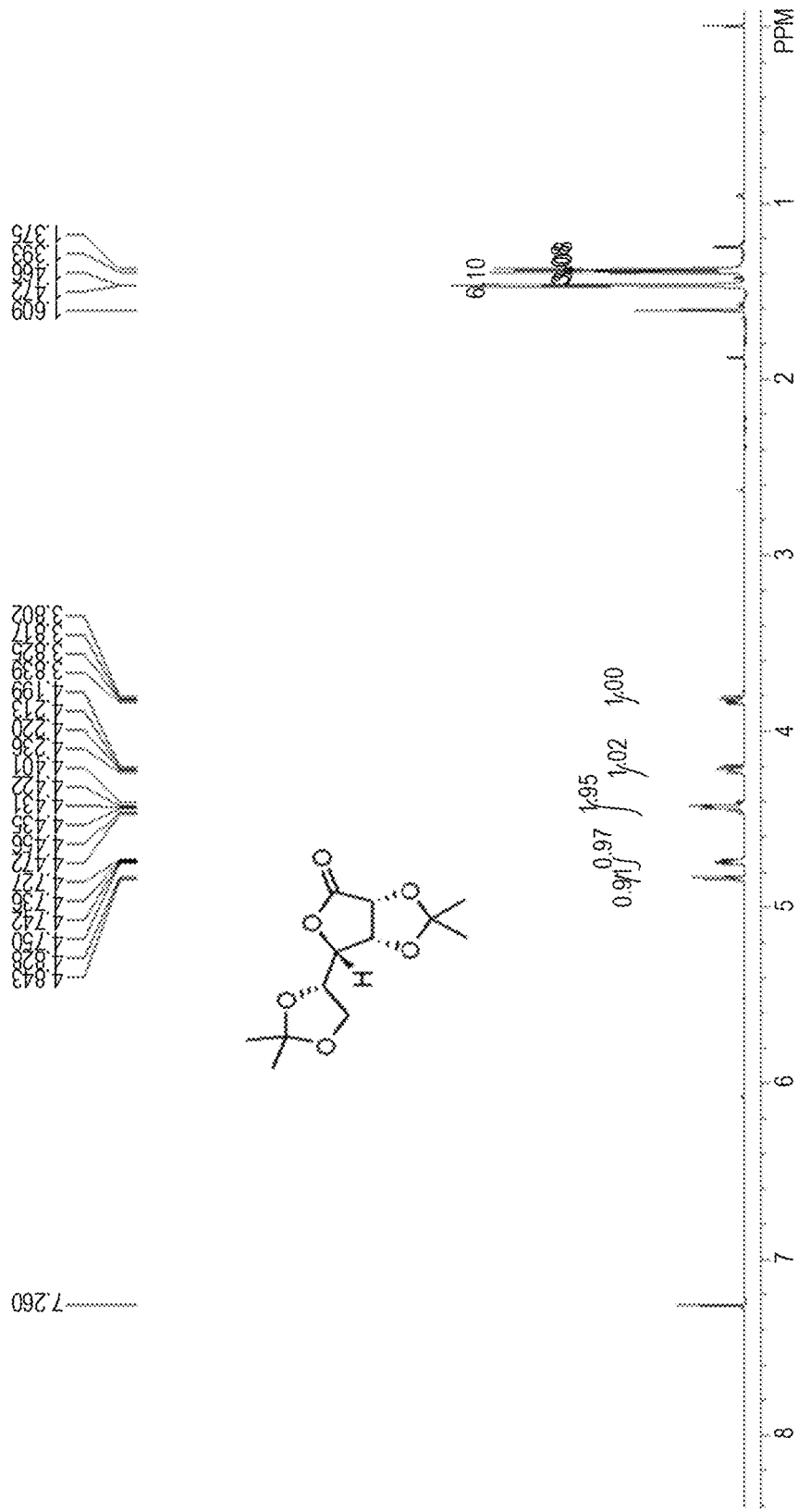
FIG. 19: $^1H$ NMR spectra of (3 aR,6S,6aR)-6-((S)-2,2-dimethyl-1,3-dioxolan-4-yl)-2,2-dimethyldihydrofuro[3,4-d][1,3]dioxol-4(3aH)-one (Compound 2).
Figure 20:
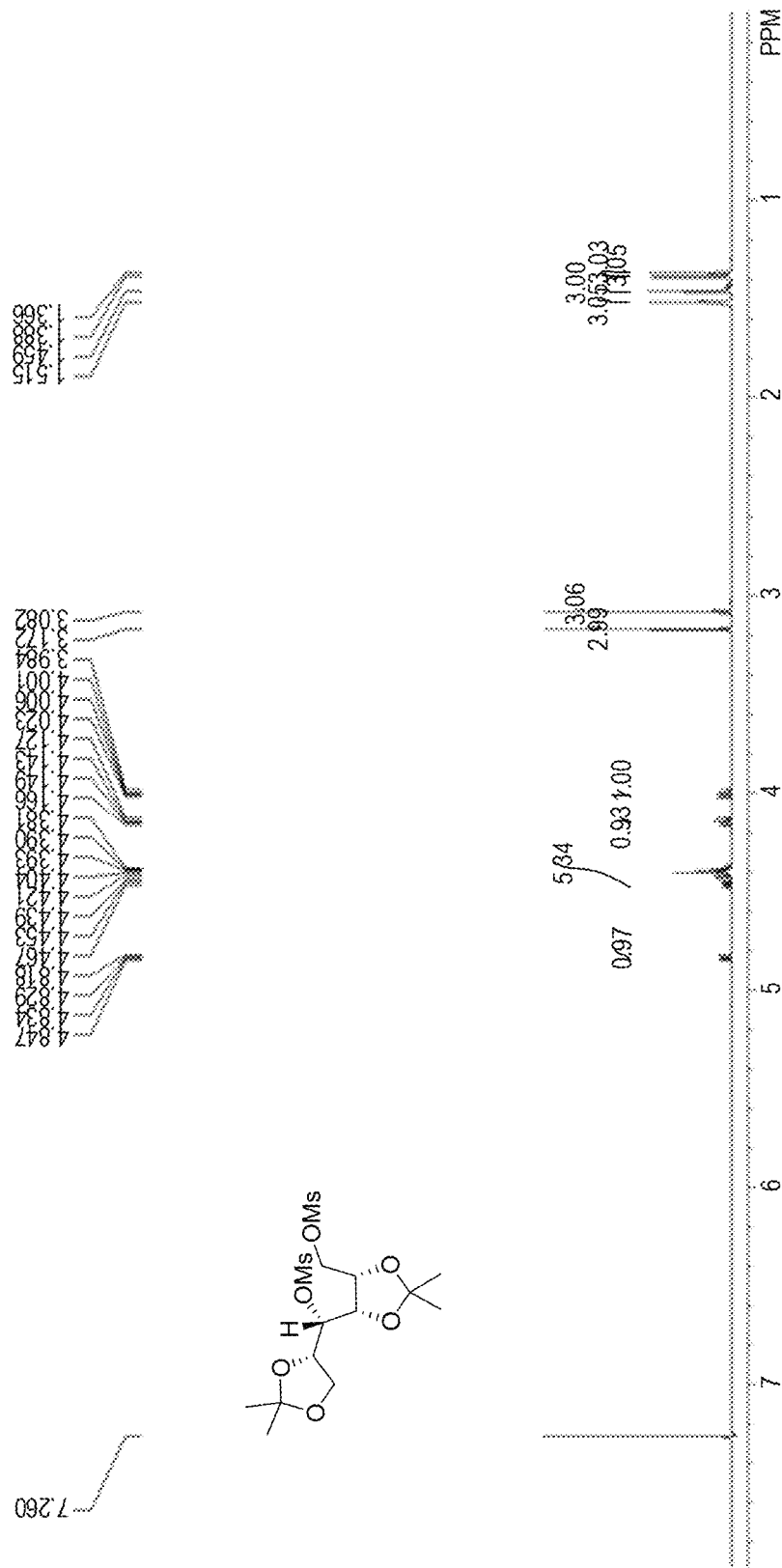
FIG. 20: $^1H$ NMR spectra of (S)—((S)-2,2-dimethyl-1,3-dioxolan-4-yl)((4S,5S)-2,2-dimethyl-5-(((methylsulfonyl)oxy)methyl)-1,3-dioxolan-4-yl)methyl methanesulfonate (Compound 3).
Figure 21:
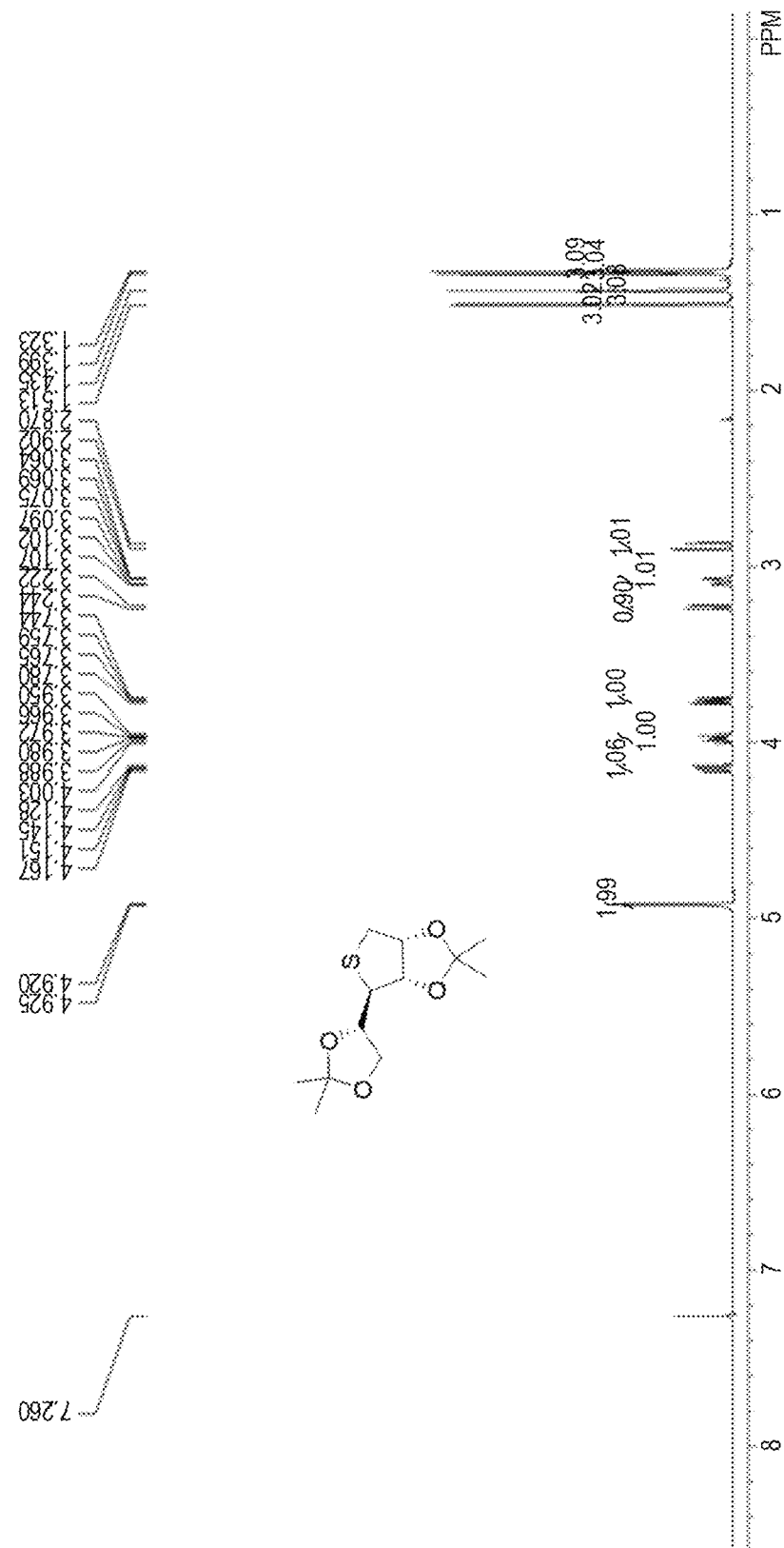
FIG. 21: $^1H$ NMR spectra of (3aS,4R,6aR)-4-((5)-2,2-dimethyl-1,3-dioxolan-4-yl)-2,2-dimethyltetrahydrothieno[3,4-d][1,3]dioxole (Compound 4).
Figure 22:
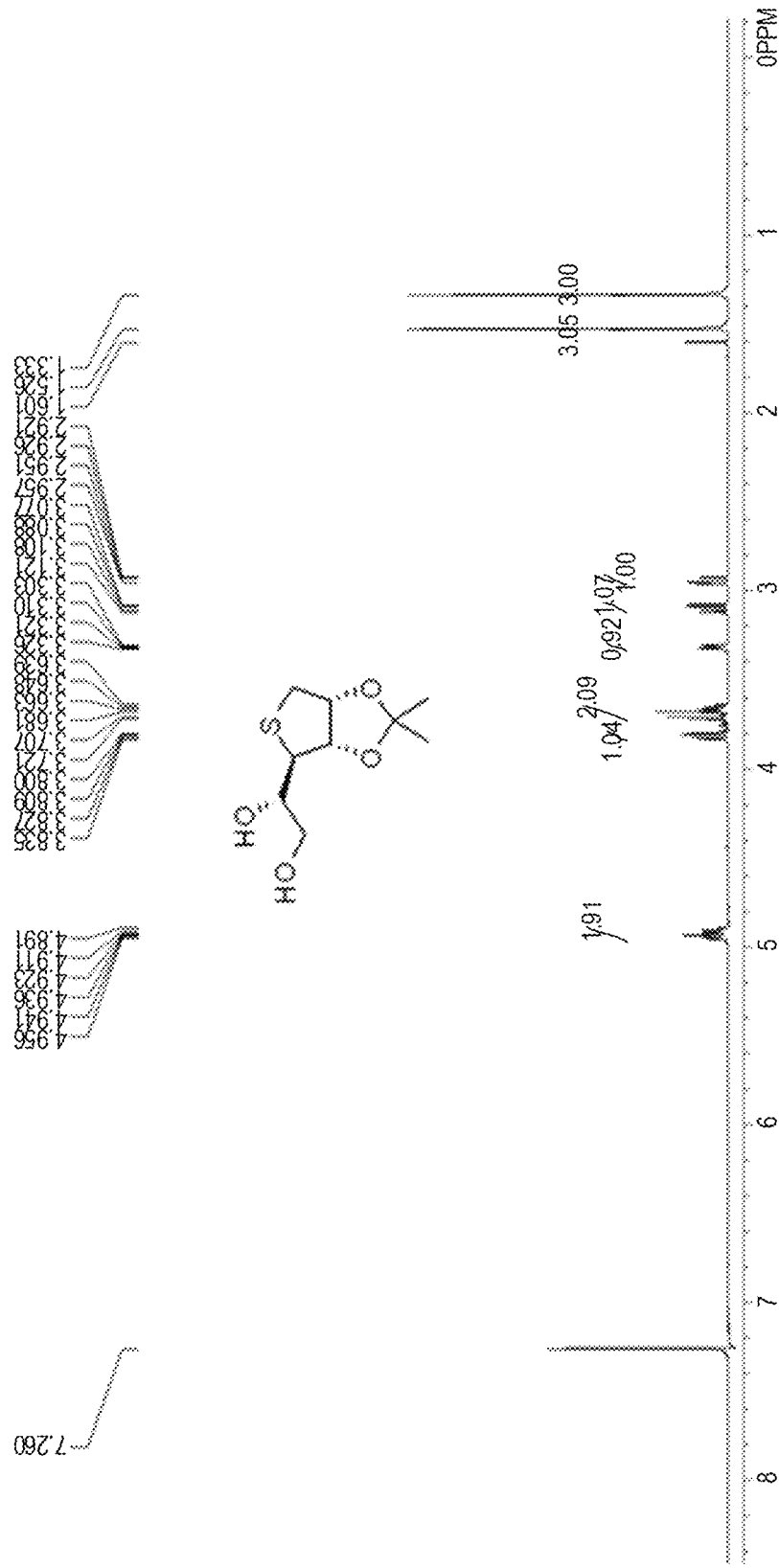
FIG. 22: $^1H$ NMR spectra of (S)-1-((3aS,4R,6aR)-2,2-dimethyltetrahydrothieno[3,4-d][1,3]dioxol-4-yl)ethane-1,2-diol (Compound 5)
Figure 23:
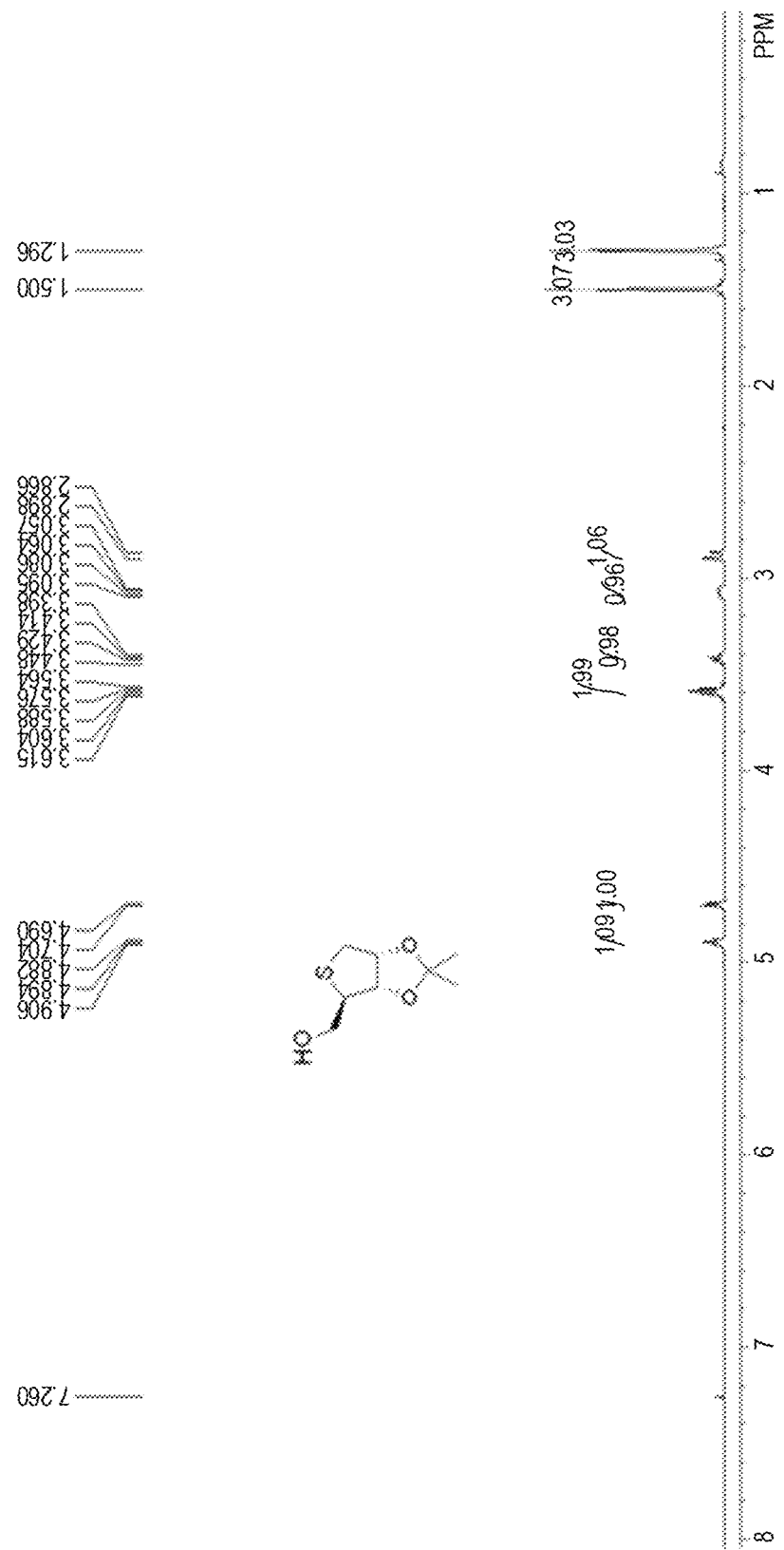
FIG. 23: $^1H$ NMR spectra of ((3 aS,4R,6aR)-2,2-dimethyltetrahydrothieno[3,4-d][1,3]dioxol-4-yl)methanol (Compound 6).
Figure 24:
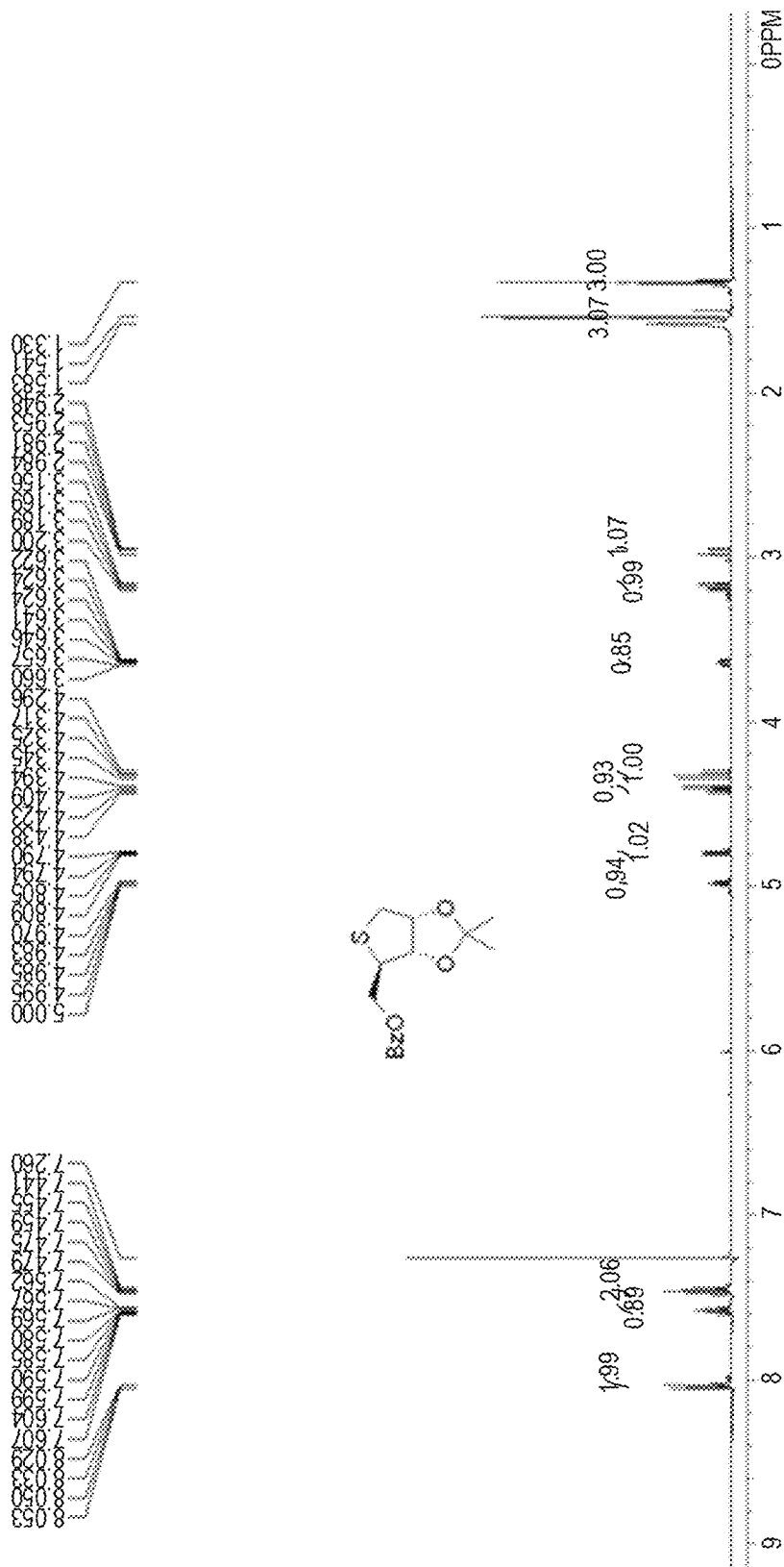
FIG. 24: $^1H$ NMR spectra of ((3 aS,4R,6aR)-2,2-dimethyltetrahydrothieno[3,4-d][1,3]dioxol-4-yl)methyl benzoate (Compound 7).
Figure 25:
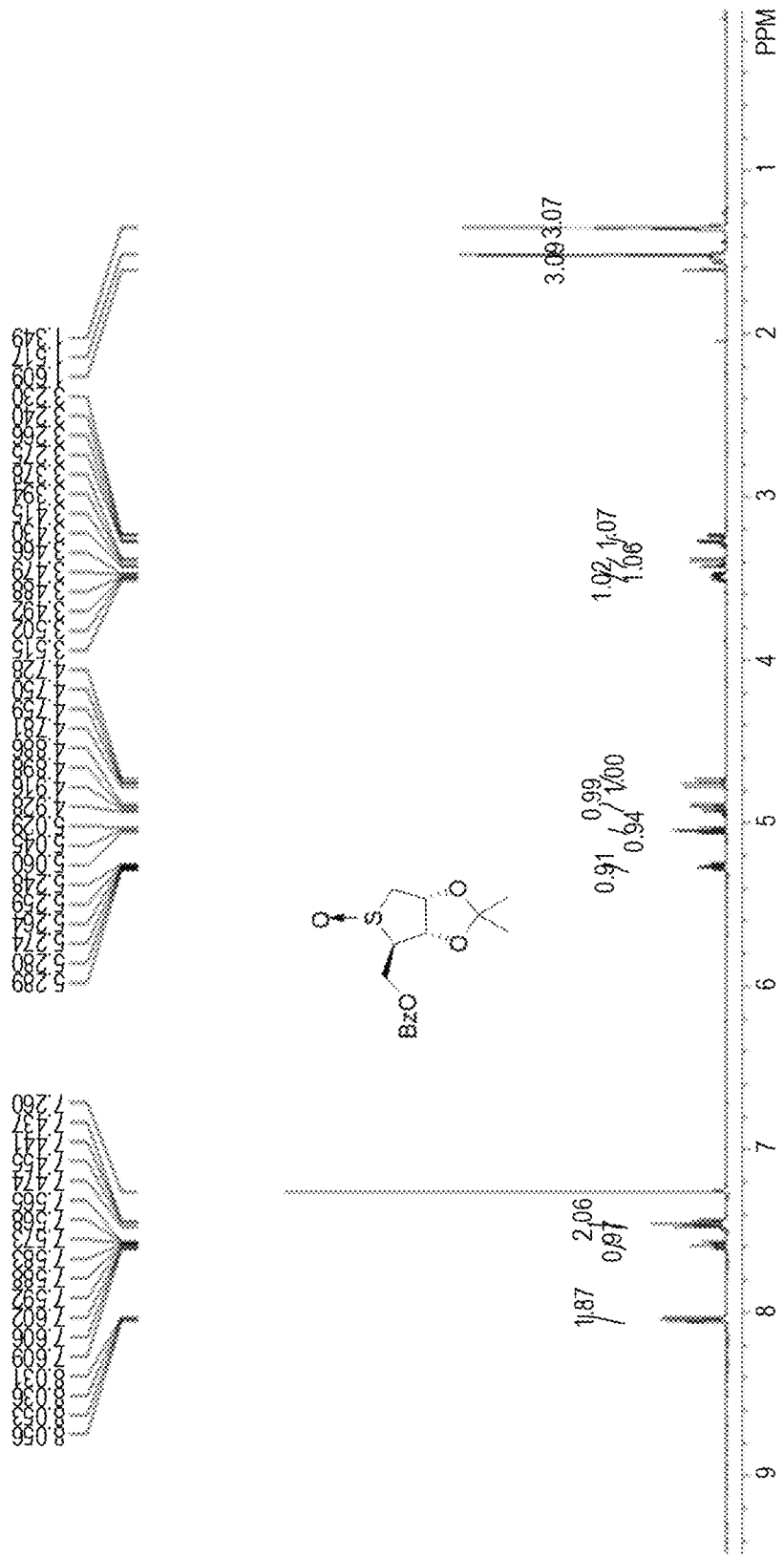
FIG. 25: $^1H$ NMR spectra of Compound 8.
Figure 26:
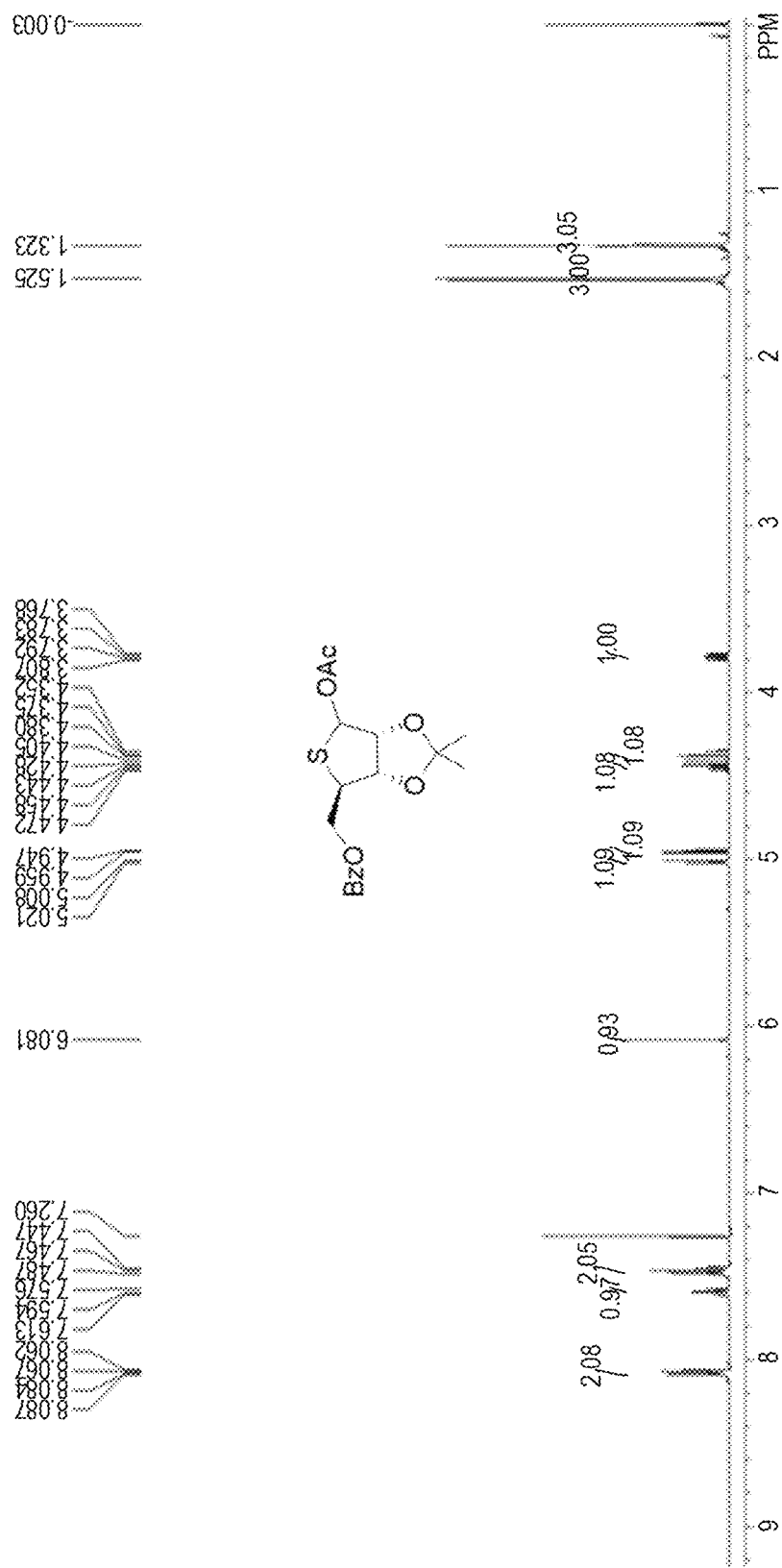
FIG. 26: $^1H$ NMR spectra of ((3aS,4R,6aR)-6-acetoxy-2,2-dimethyltetrahydrothieno[3,4-d][1,3]dioxol-4-yl)methyl benzoate (Compound 9).
Figure 27A:
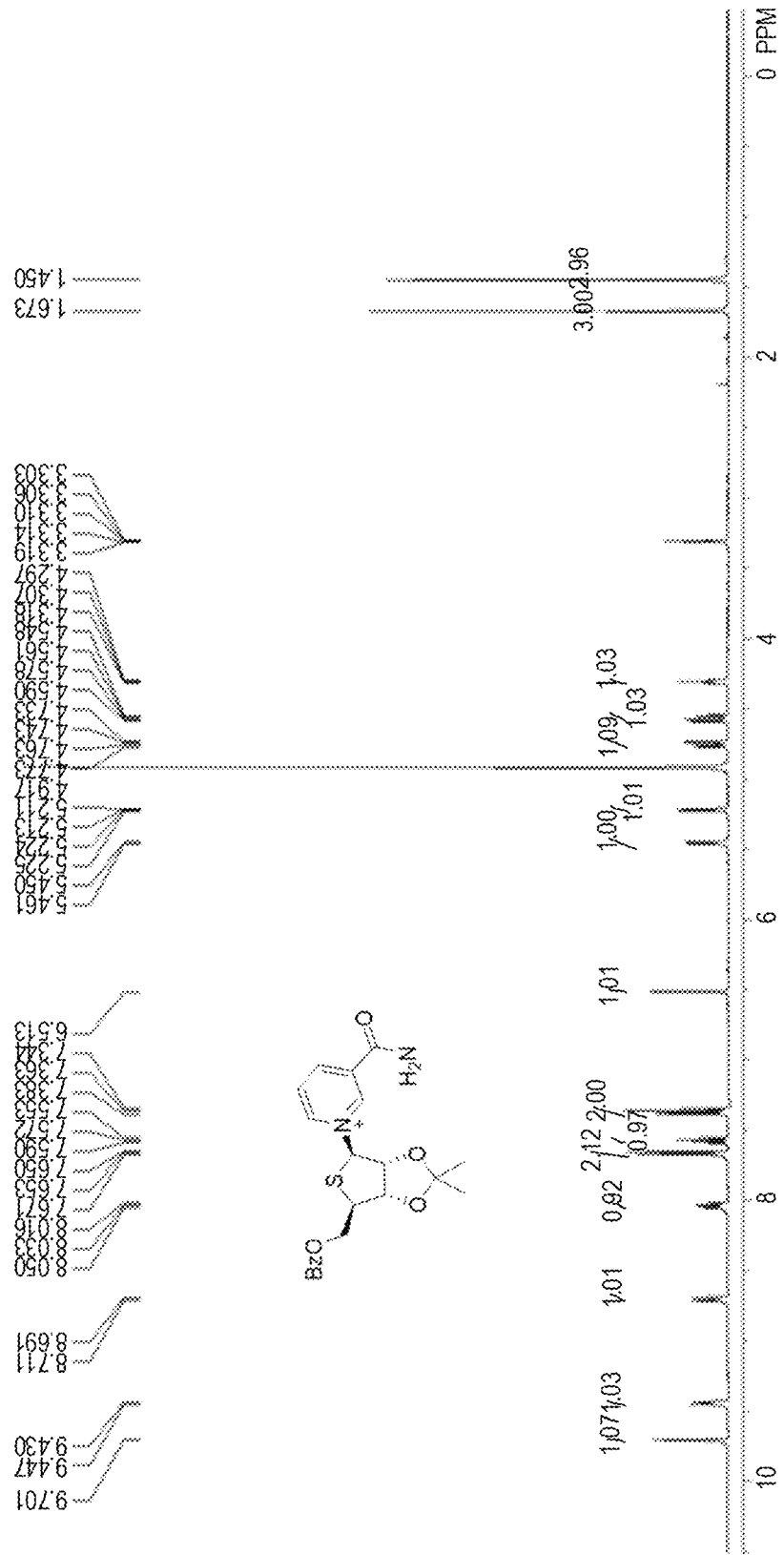
FIGS. 27A-27B: $^1H$ NMR spectra (FIG. 27A) and $^{13}C$ NMR spectra (FIG. 27B) of 1-((3aR,4R,6R,6aS)-6-((benzoyloxy)methyl)-2,2-dimethyltetrahydrothieno[3,4-d][1,3]dioxol-4-yl)-3-carbamoylpyridin-1-ium bromide (Compound 10).
Figure 27B:
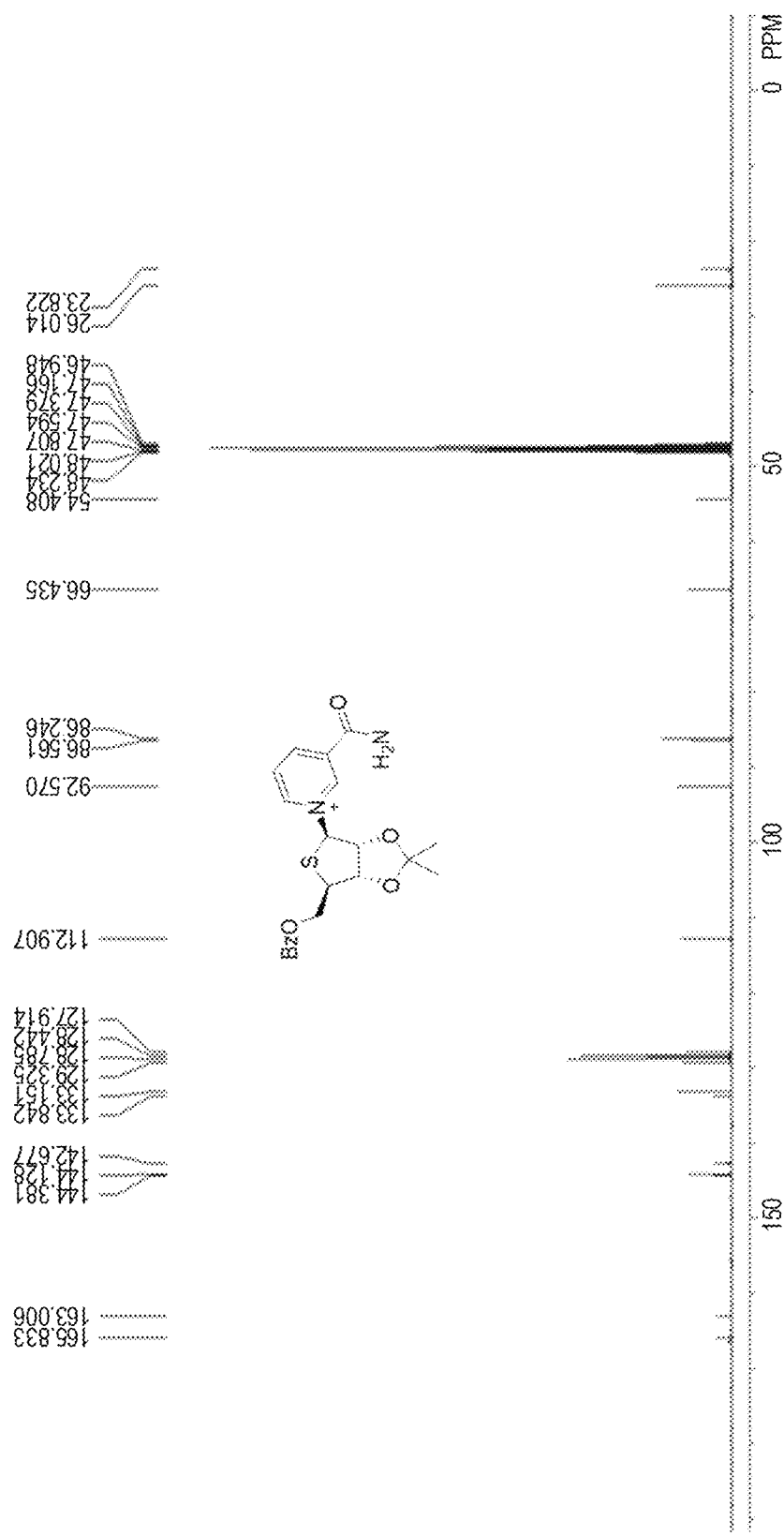
Figure 28A:
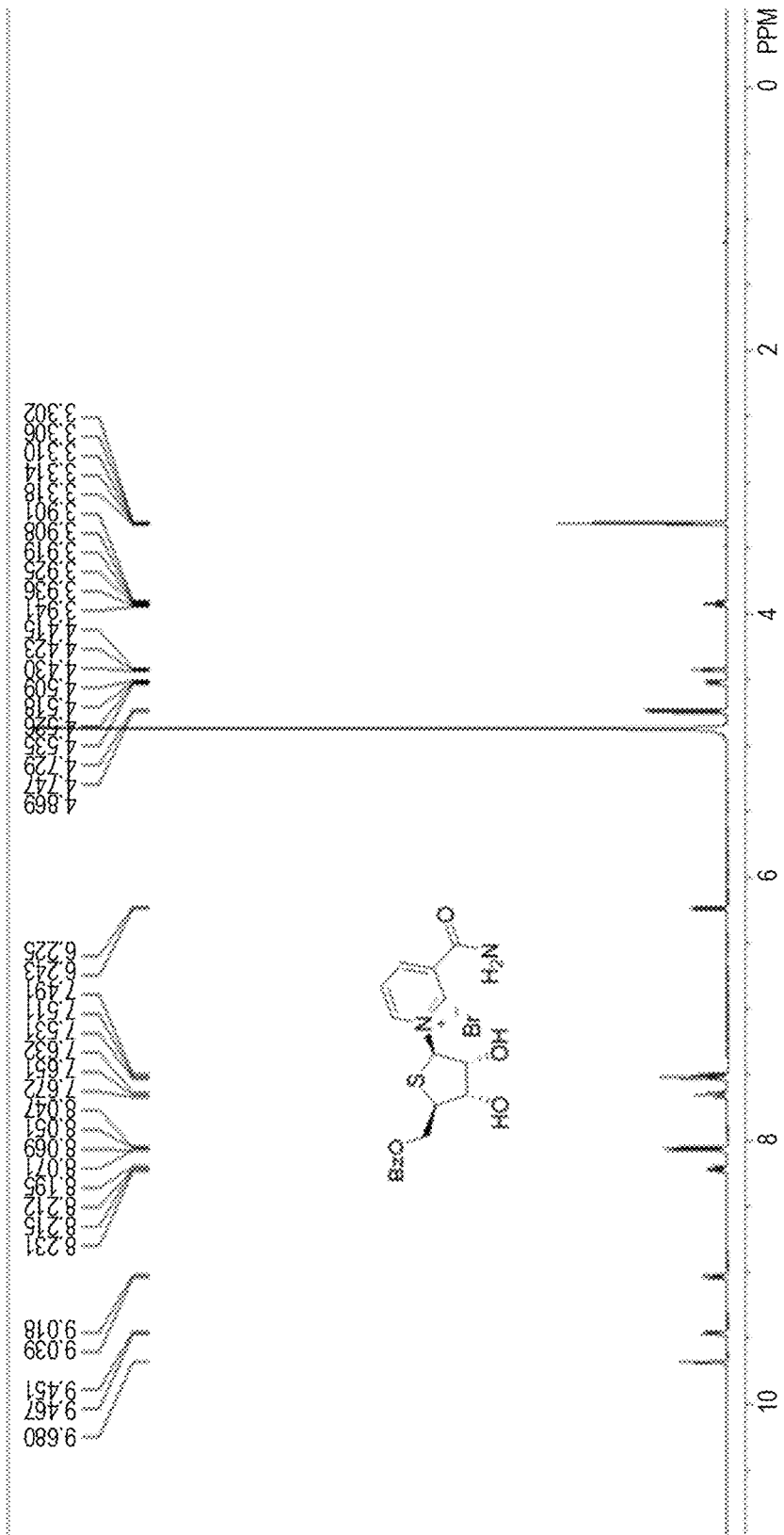
FIGS. 28A-28B: $^1H$ NMR spectra (FIG. 28A) and $^{13}C$ NMR spectra (FIG. 28B) of 1-((2R,3R,4S,5R)-5-((benzoyloxy)methyl)-3,4-dihydroxytetrahydrothiophen-2-yl)-3-carbamoylpyridin-1-ium bromide (Compound 11).
Figure 28B:
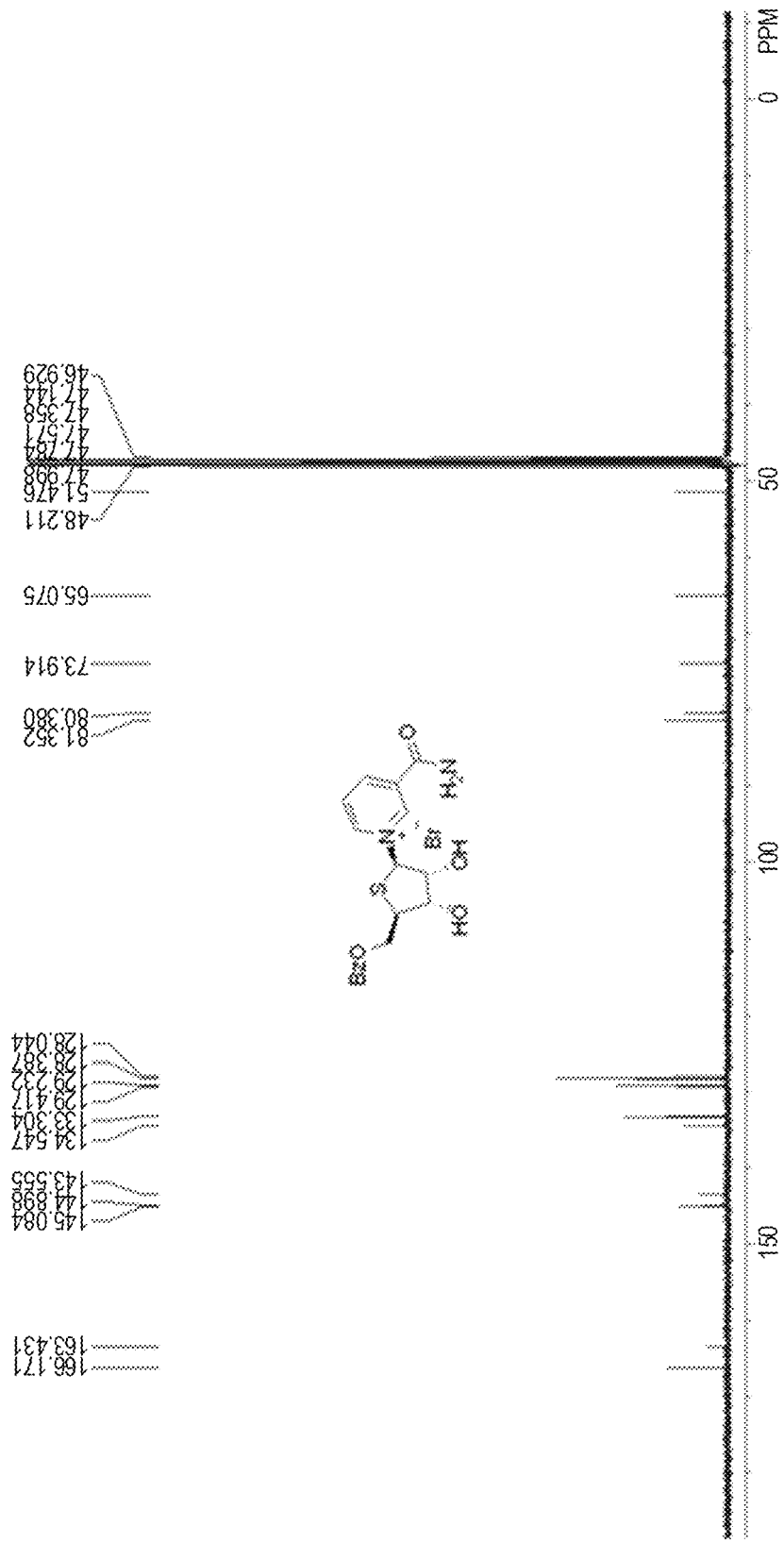
Figure 29A:
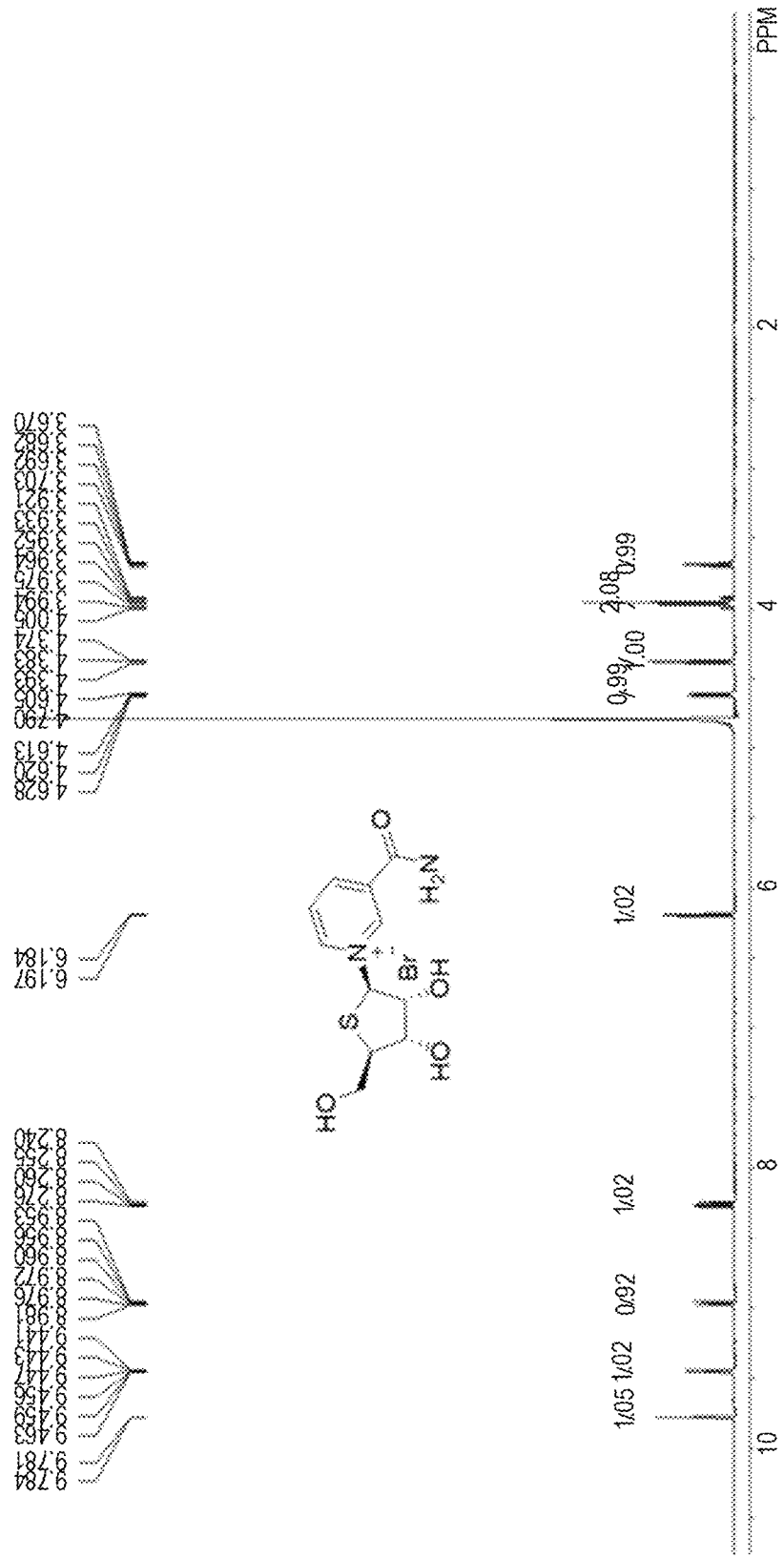
FIGS. 29A-29B: $^1H$ NMR spectra (FIG. 29A) and $^{13}C$ NMR spectra (FIG. 29B) of 3-carbamoyl-1-((2R,3R,4S,5R)-3,4-dihydroxy-5-(hydroxymethyl)tetrahydrothiophen-2-yl)pyridin-1-ium (Compound S—NR).
Figure 29B:
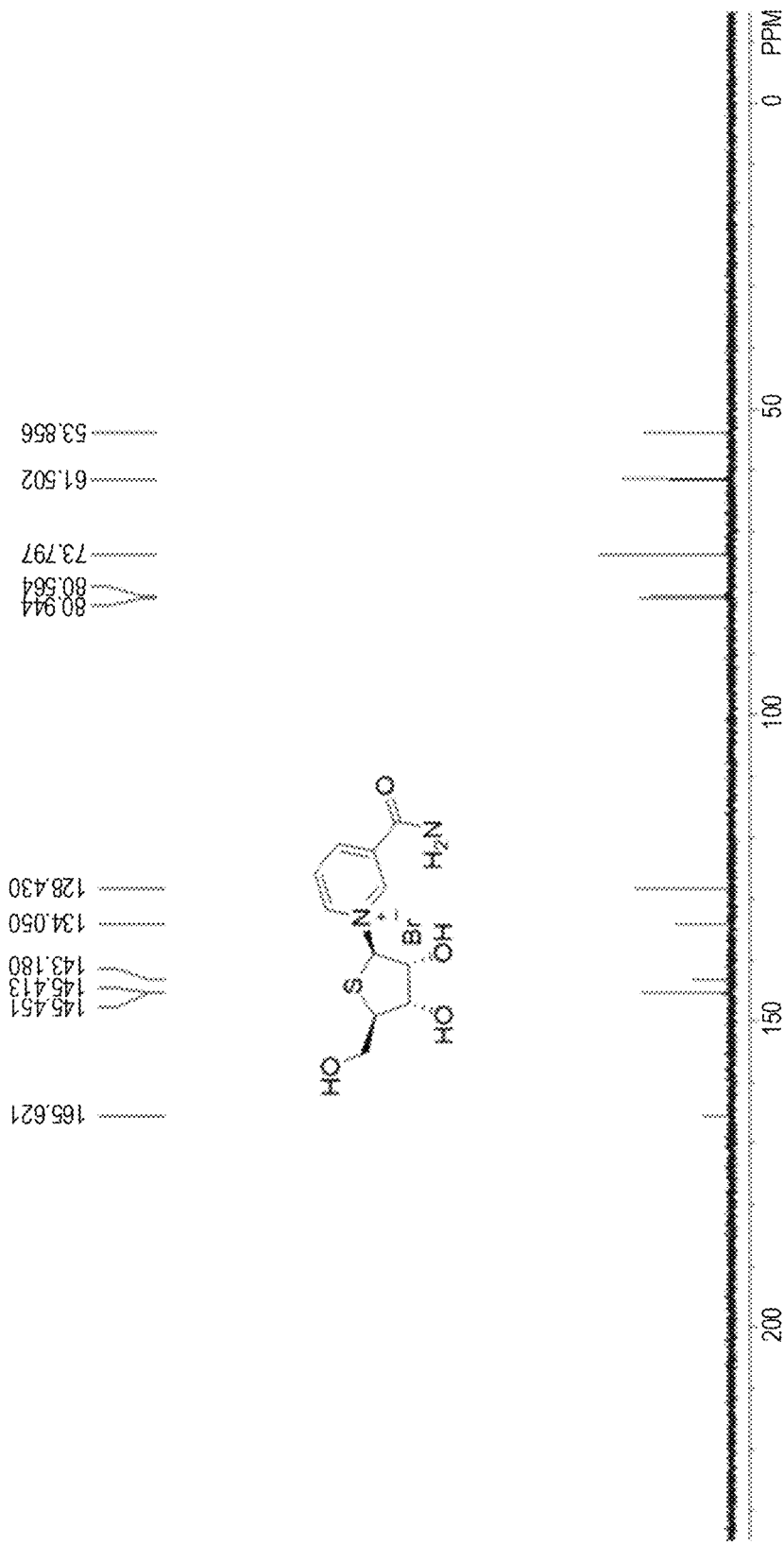
Figure 30A:
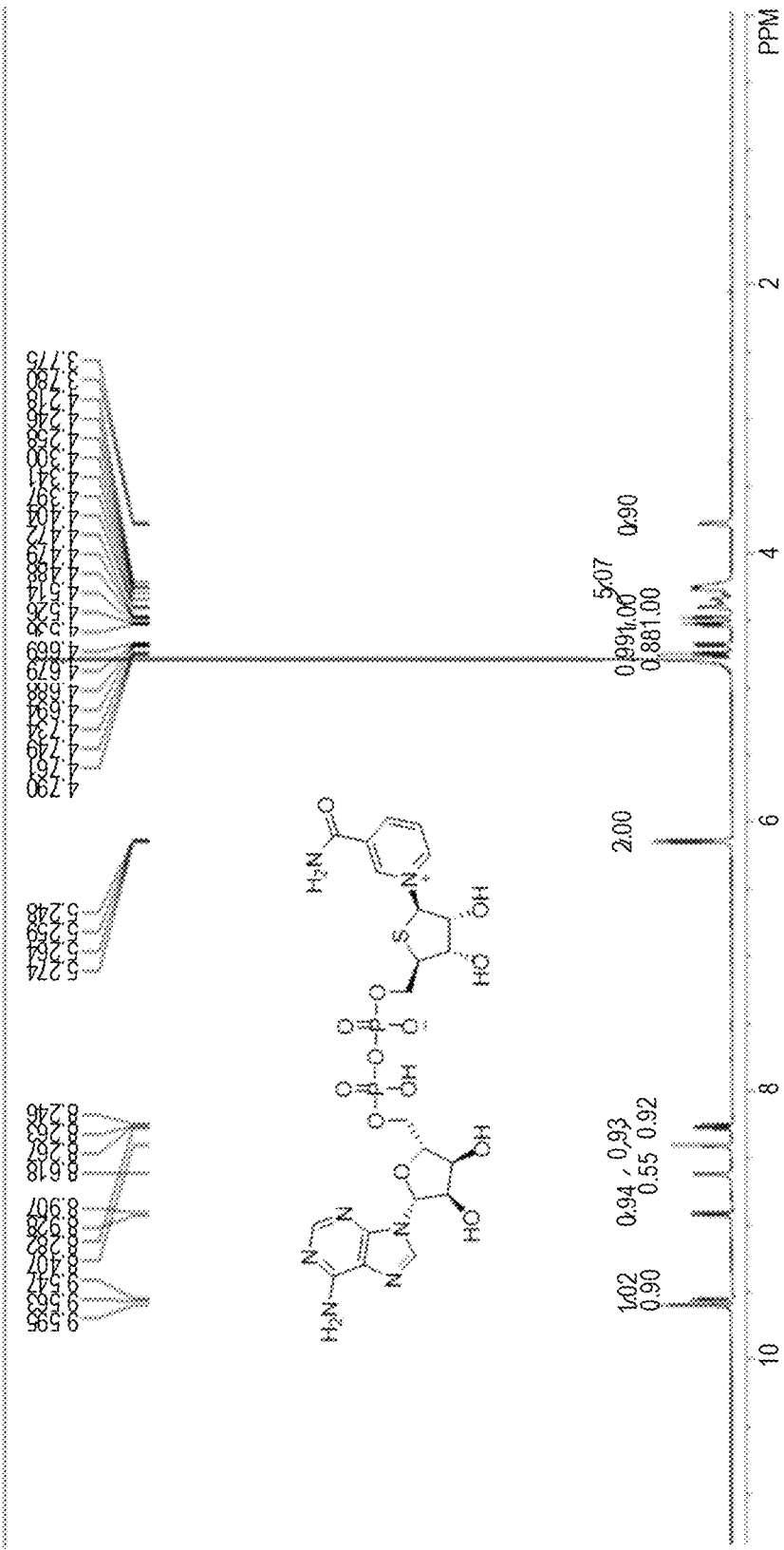
FIGS. 30A-30B: $^1H$ NMR spectra (FIG. 30A) and $^{13}C$ NMR spectra (FIG. 30B) of Compound $S-NAD^+$.
Figure 30B:
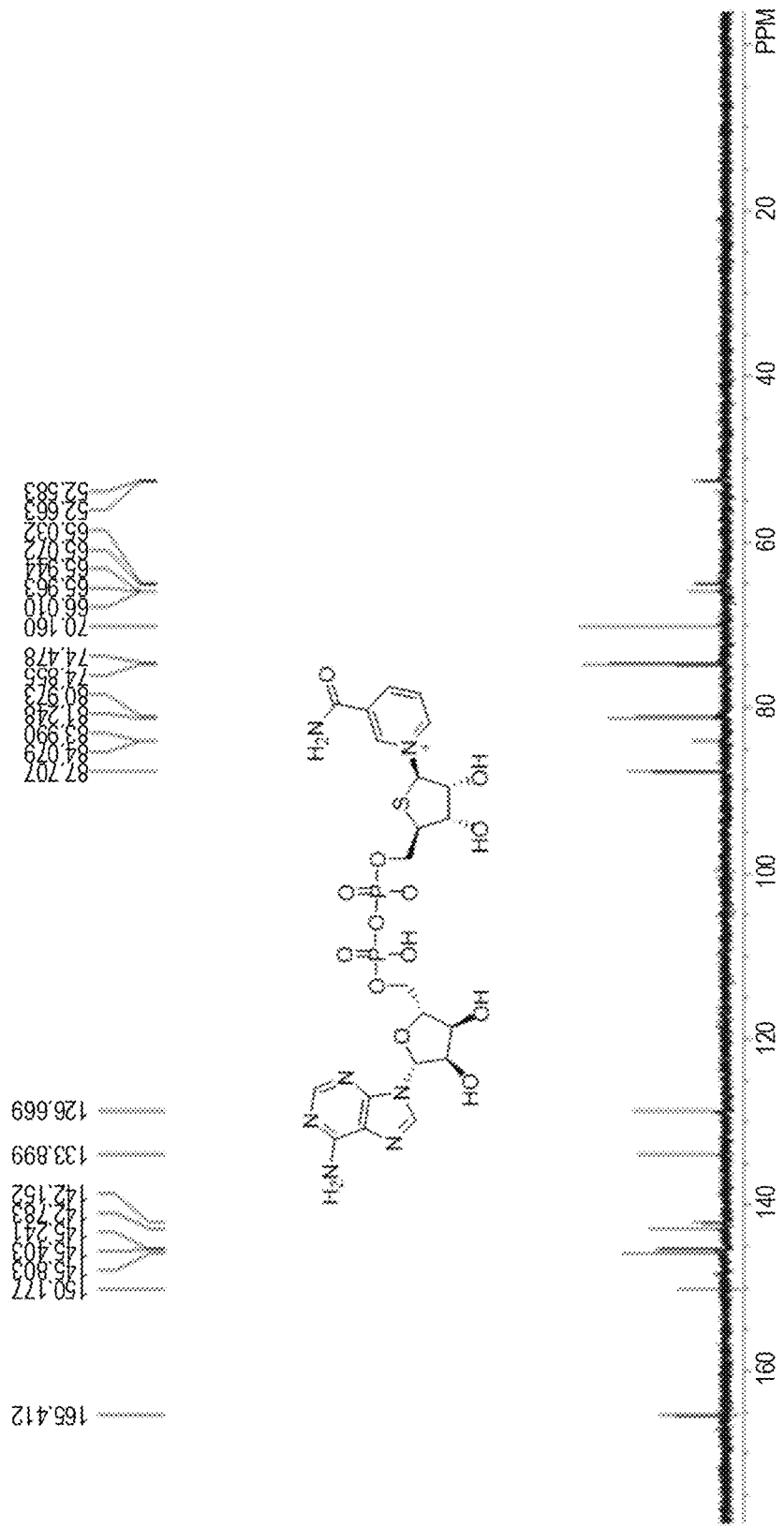

To test this notion, S—NR was first chemically synthesized. As shown in FIG. 18, 1-acetoxy thioribose 9 was prepared from D-gulonic acid γ-lactone according to the reported procedures.[43] Despite established methods for synthesis of NR via introduction of nicotinamide onto ribose, S—NR is yet to be developed.[44-47] By testing the substitution of nicotinamide for OAc group of 9, it was found that treatment of 9 with sequential HBr (33% (wt) in acetic acid) in toluene at 0° C. for 4 hours and nicotinamide in CH$_3$CN at room temperature for 18 hours successfully afforded 10 in a 58% yield (FIG. 18). S—NR was then generated through subsequent deprotections of the 4'-thioribose ring.

Figure 5A:
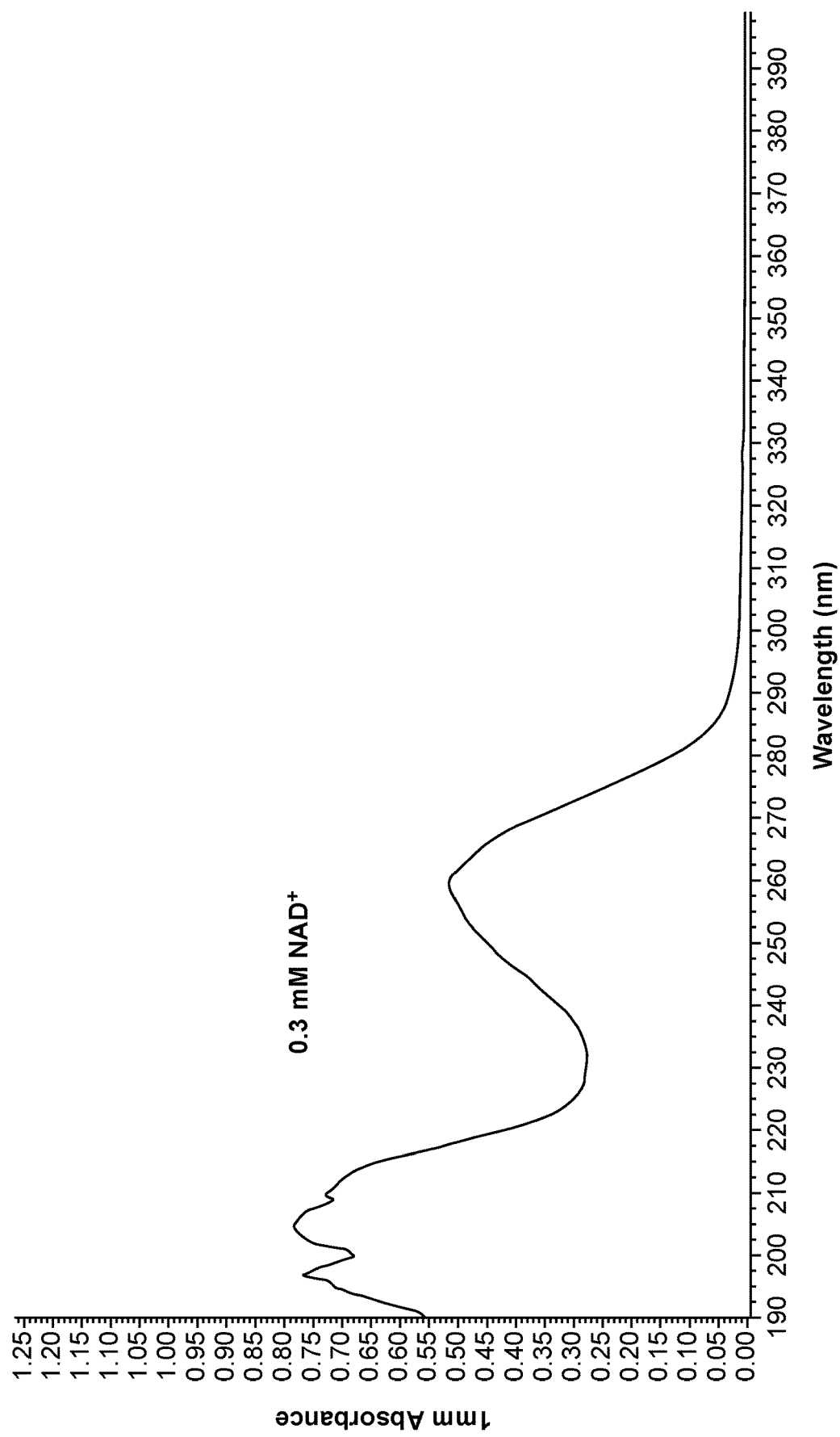
FIGS. 5A-5B: UV absorption spectra of $NAD^+$ and $S-NAD^+$. 0.3 mM $NAD^+$ (FIG. 5A) or $S-NAD^+$ (FIG. 5B) was used to measure the UV absorption spectra (190-400 nm) by a NanoDrop 2000C spectrophotometer.
Figure 5B:
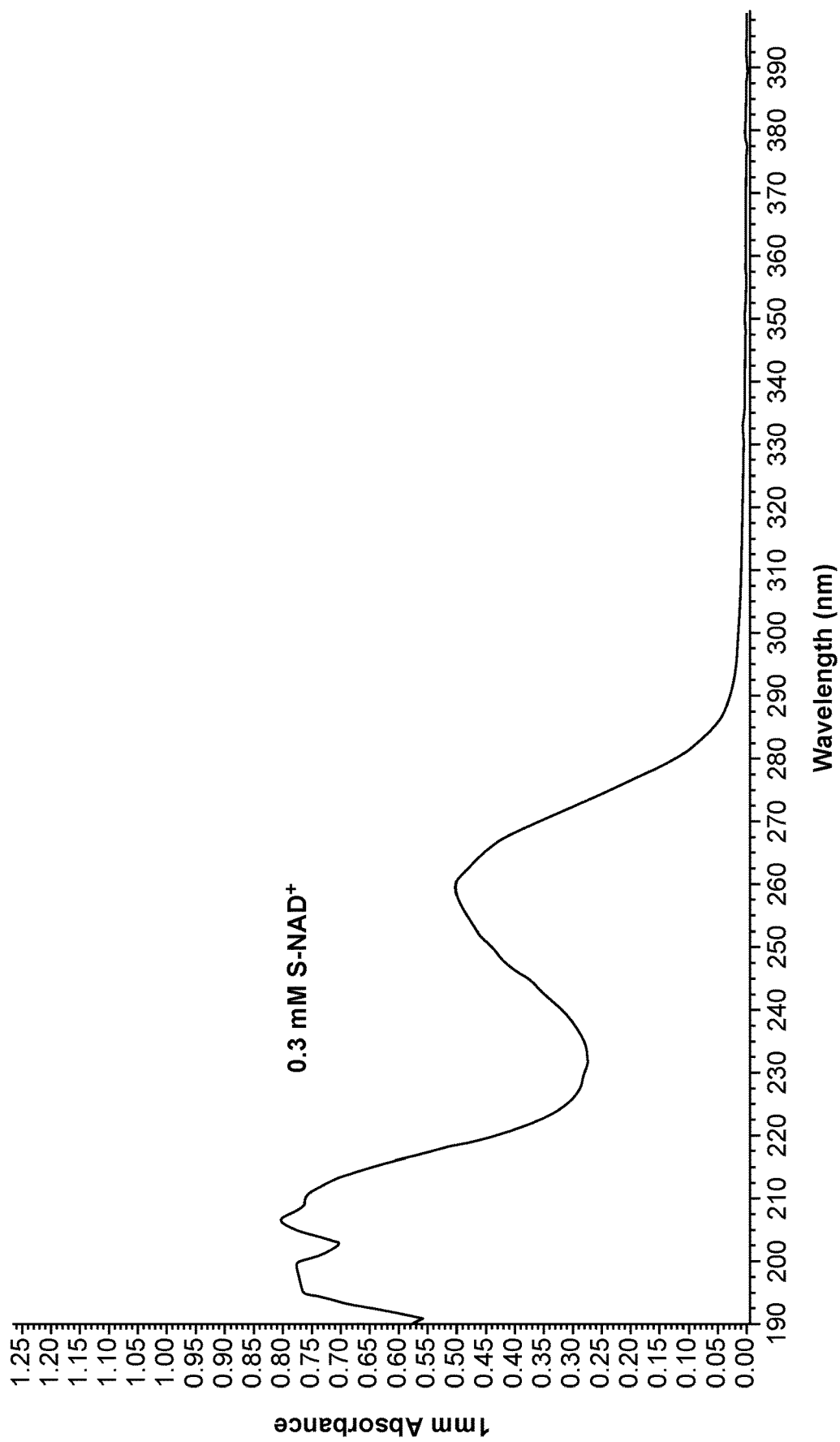

Human NRK1 and NMNAT1 were then expressed and purified from *Escherichia coli* (FIG. 1). In vitro biosynthesis of NAD+ and S-NAD+ from NR and S—NR, respectively, were carried out using purified NRK1 and NMNAT1. In the presence of NRK1 and NMNAT1 and ATP, a large amount of NAD+ and S-NAD+ were rapidly formed within 4-hour incubation (FIGS. 12B-12E and FIG. 2-FIG. 4). The formation rate of S-NAD+ was comparable to that of NAD+. In contrast to the last two steps of chemical synthesis of NAD+ analogues that usually take two to four days and are characterized by tedious purification procedures and low yields, enzymatic conversion of S—NR to S-NAD+ by NRK1 and NMNAT1 could be completed within four hours with a final yield of 70% and requires significantly less efforts on purification (FIG. 18). These results demonstrate a facile and efficient chemoenzymatic approach for the generation of S-NAD+. The sulfur substitution seemed to have no effect on substrate activities of S—NR and 4'-thioribose nicotinamide mononucleotide (S-NMN) for human NRK and NMNAT, respectively. In addition, the UV absorption spectrum of the generated S-NAD+ is nearly identical to that of NAD+ (FIG. 5).

Figure 13:
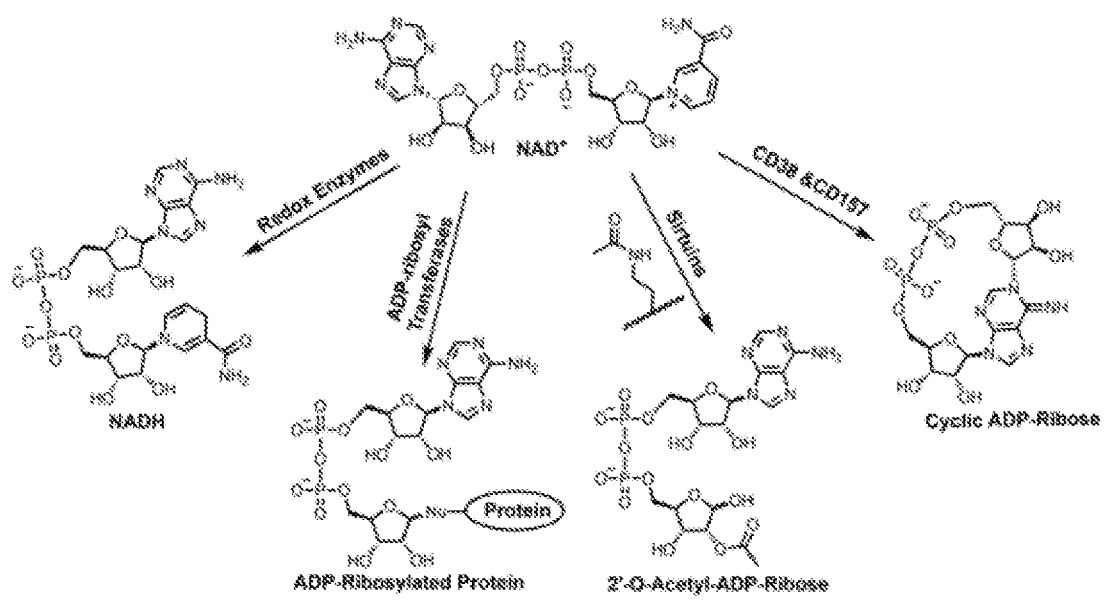
FIG. 13: $NAD^+$ participates in chemical reactions catalyzed by distinct classes of enzymes.

To evaluate chemical stability of the generated S-NAD+, recombinant extracellular domain of human CD38 was chosen as a model enzyme (FIG. 6), which catalyzes rapid formation of ADPR and cADPR from NAD+. HPLC analysis revealed that in contrast to NAD+ that was completely consumed by human CD38 after overnight reaction, S-NAD+ still remained unchanged after overnight incubation with CD38 (FIG. 13). These results indicate that relative to NAD+, the synthesized S-NAD+ is more resistant to cleavage catalyzed by CD38 enzyme and support that 4'-thioribose substitution for NR ribosyl group results in an NAD+ analogue chemically inert to catalysis for N-glycosidic bond breakage.

Figure 7:
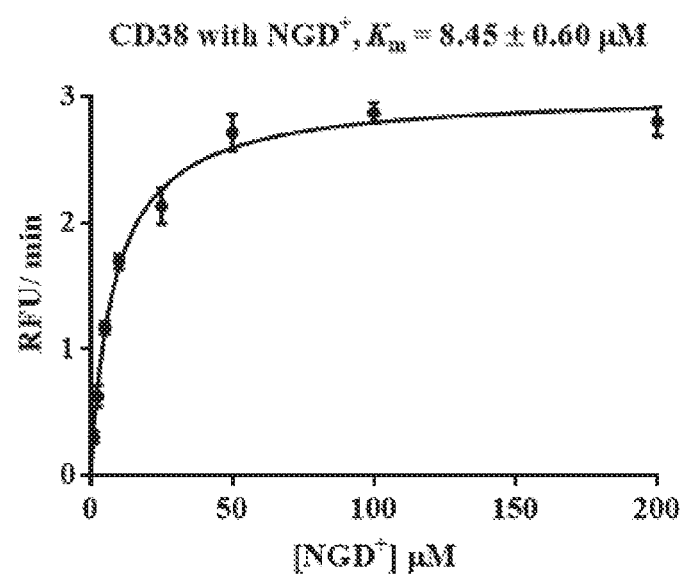
FIG. 7: Enzymatic parameter of the ADP-ribosyl cyclase activity of the purified human CD38 with $NGD^+$ as a substrate.
Figures 8A, 8B:
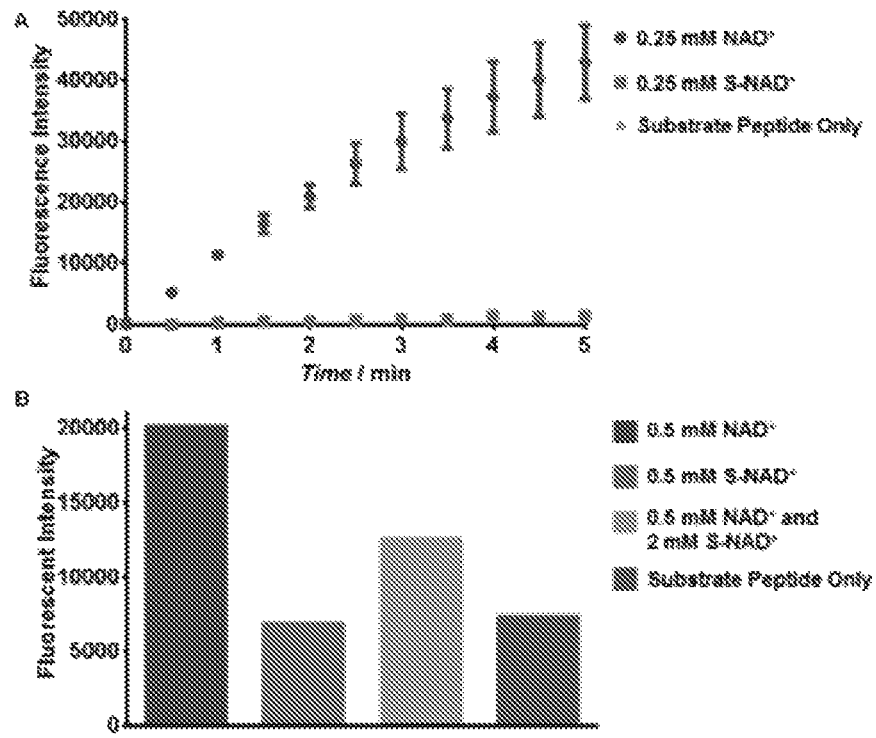
FIGS. 8A-8B: Substrate activities of $NAD^+$ and $S-NAD^+$ with human SIRT2. The deacetylation activity for recombinant human SIRT2 was measured using a trypsin-coupled fluorescence-based assay at 460 nm on the basis of the released 7-amino-4-methylcoumarin (AMC) from a deacetylate peptide substrate cleaved by trypsin.
Figures 14A, 14B, 14C, 14D, 14E:
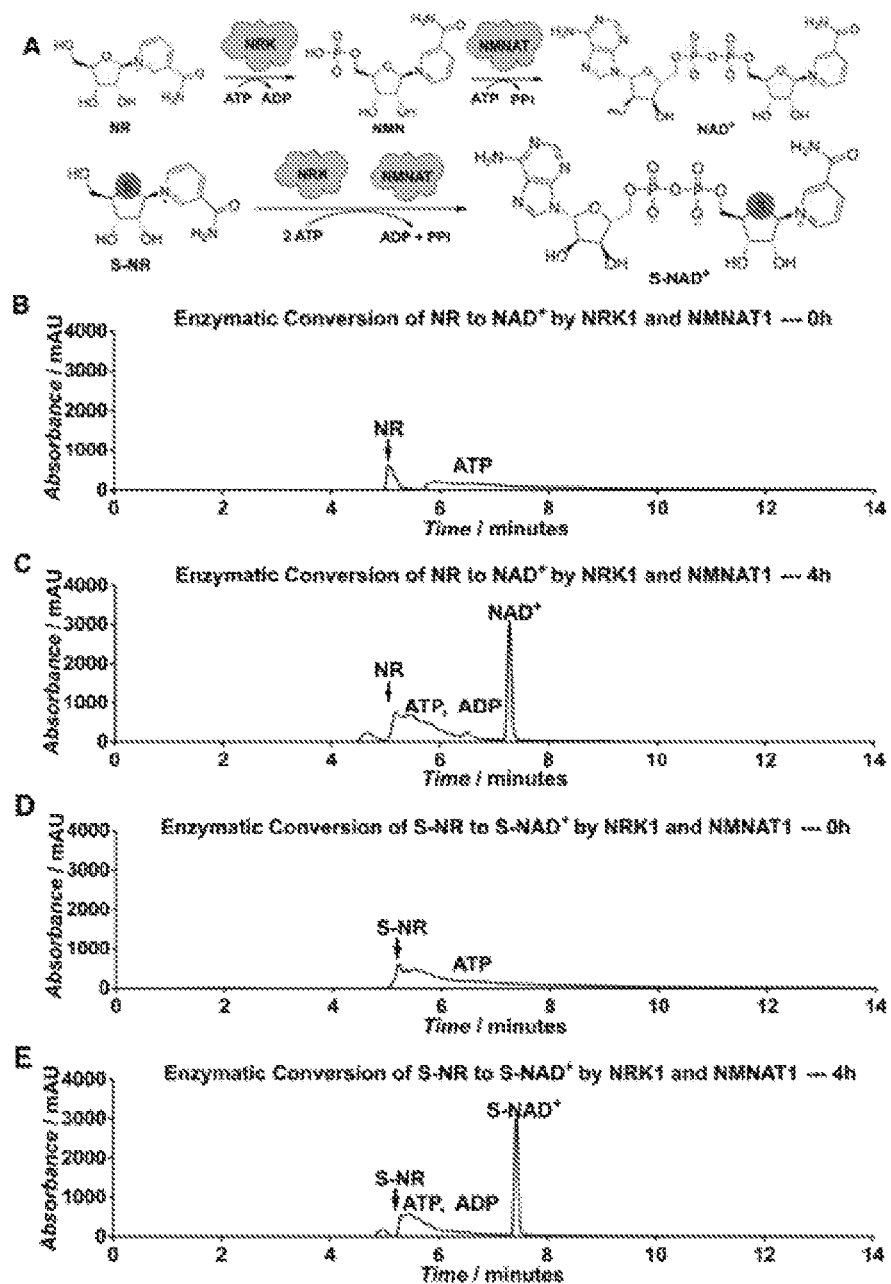
FIGS. 14A-14E: Enzymatic synthesis of $NAD^+$ and $S-NAD^+$.

Next, the generated S-NAD+ was examined for its competitive inhibition activity for human CD38 enzyme by performing a continuous fluorescence-based activity assay using nicotinamide guanine dinucleotide (NGD+) as a substrate. The cyclase activity of CD38 catalyzes formation of fluorescent cyclic GDP-ribose (cGDPR) from NGD+.[48] On the basis of cGDPR-derived fluorescence, kinetics for human CD38-catalyzed conversion of NGD+ to cGDPR was examined and the $K_m$ of NGD+ for human CD38 cyclase activity was determined to be 8.5±0.6 μM (FIG. 7). Competitive inhibition assays showed that S-NAD$^+$ exhibits a dose-dependent inhibition of cGDPR formation by CD38 with a $K_i$ of 28.5±3.1 µM (FIG. 14), comparable to previously determined $K_m$ values of NAD$^+$ for CD38 enzyme.[49,50] These results suggest that by mimicking NAD$^+$, S-NAD$^+$ could bind to the active site of human CD38 to inhibit its enzymatic activity and a single atomic substitution within the ribosyl ring seems to induce no adverse effects on its binding to the CD38 enzyme. Additionally, no slow-onset inhibition was observed for S-NAD$^+$ in direct competition assays with extended incubation or in studies of preincubating CD38 with S-NAD$^+$.

Figure 9:
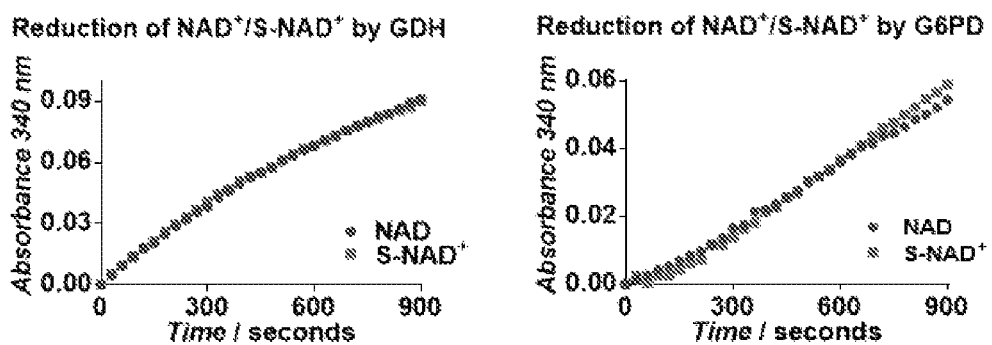
FIG. 9: Substrate activities of $NAD^+$ and $S-NAD^+$ with bovine GDH and *L. mesenteroides* G6PD enzymes. The reactions were monitored by UV absorbance at 340 nm.
Figures 10A, 10B, 10C, 10D:
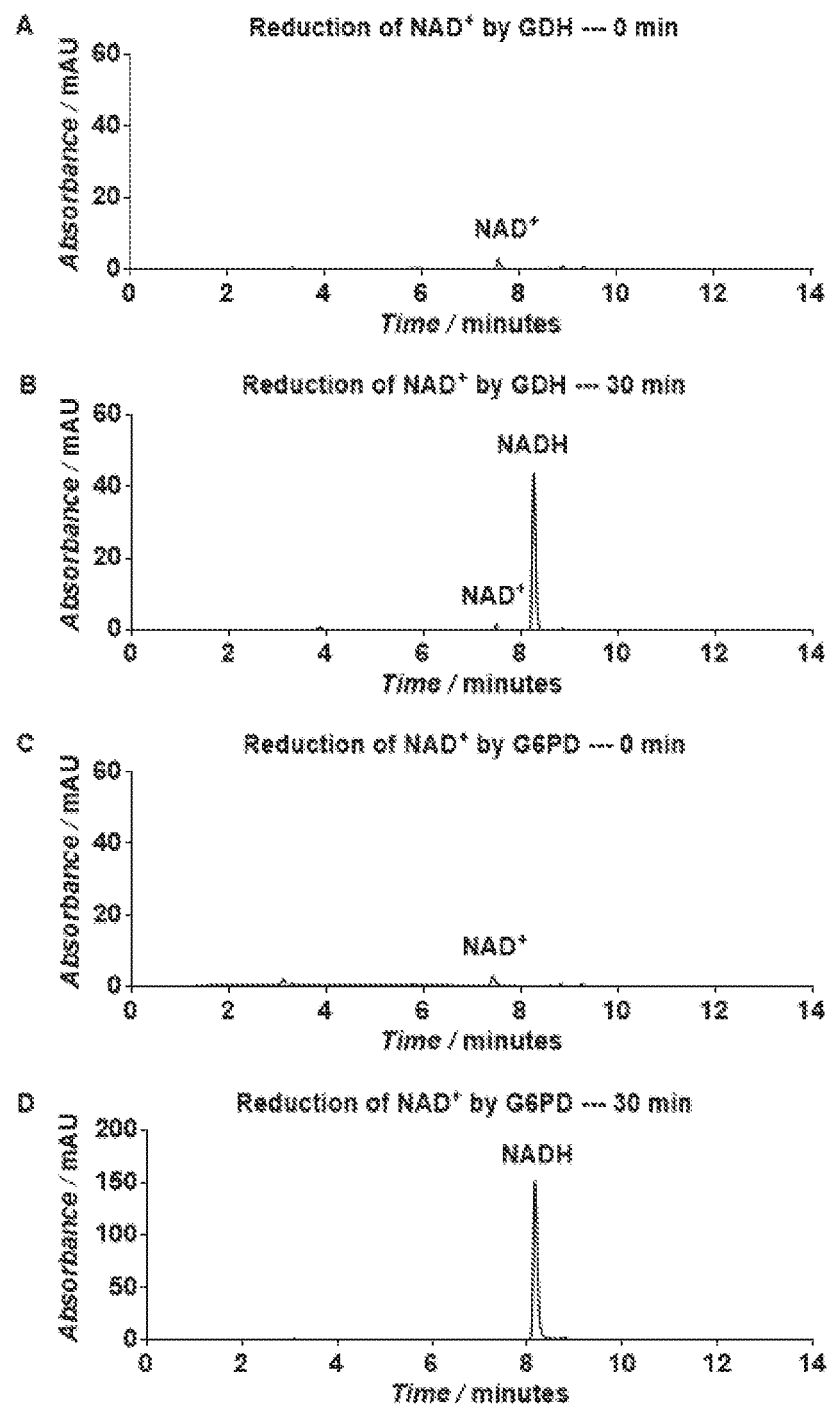
FIGS. 10A-10D: HPLC analysis of reduction of $NAD^+$ by bovine GDH and *L. mesenteroides* G6PDH as measured by UV absorbance at 340 nm.
Figures 11A, 11B, 11C, 11D:
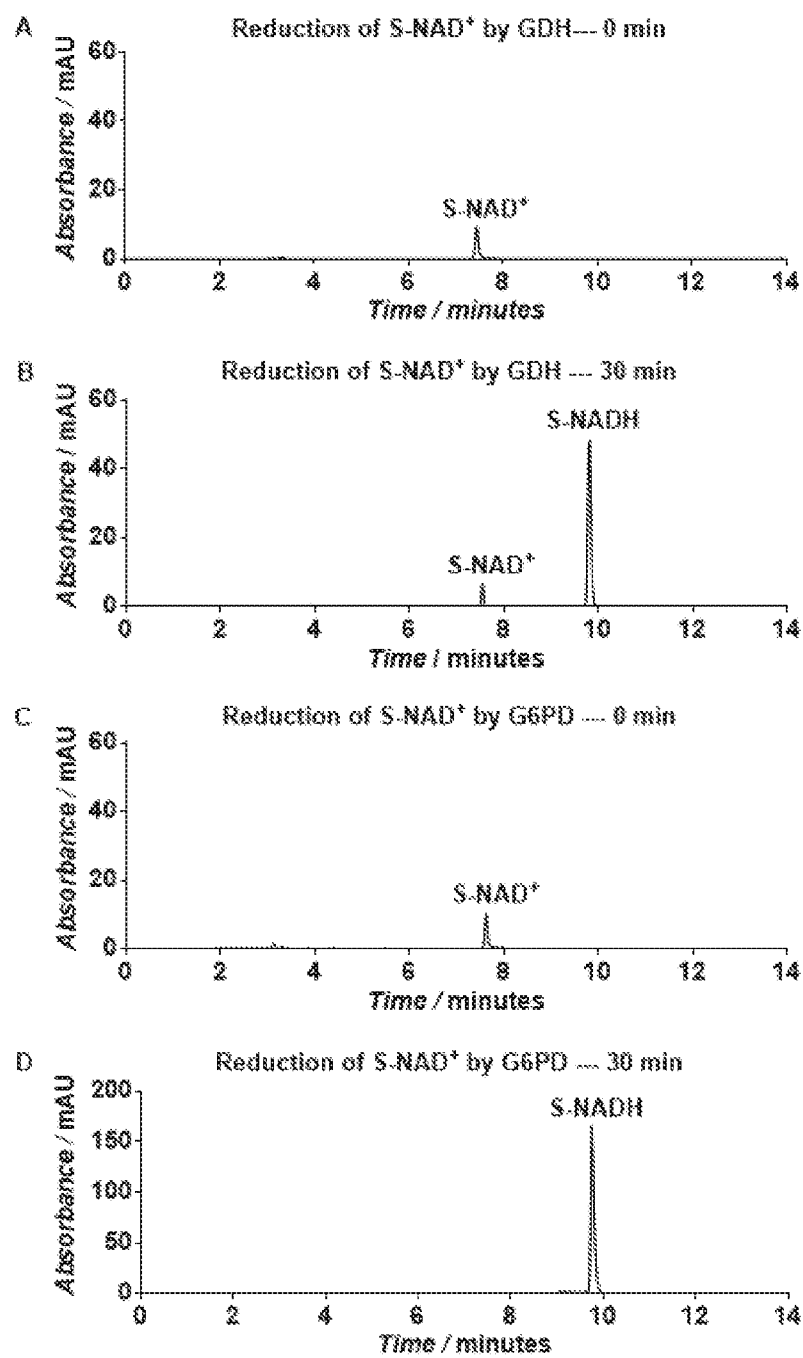
FIGS. 11A-11D: HPLC analysis of reduction of $S-NAD^+$ by bovine GDH and *L. mesenteroides* G6PDH as measured by UV absorbance at 340 nm.

In addition to enhancing stability of the N-glycosidic linkage between nicotinamide and ribose ring, replacing the endocyclic oxygen with sulfur is expected to have no impact on reduction of nicotinamide ring in oxidation-reduction reactions. To determine whether S-NAD$^+$ could participate in electron transfer reactions, bovine glutamate dehydrogenase (GDH) and *Leuconostoc mesenteroides* glucose-6-phosphate dehydrogenase (G6PDH) were utilized, which are known to catalyze oxidation of glutamate and gluocose-6-phosphate by NAD$^+$, respectively.[51,52] Enzymatic activity assays revealed that incubation of S-NAD$^+$ with bovine GDH and *L. Mesenteroides* G6PDH resulted in characteristic increases of UV absorbance at 340 nm in a manner similar to those of NAD$^+$-containing reactions (FIG. 9). HPLC analyses of the reduction of NAD$^+$ and S-NAD$^+$ by bovine GDH and *L. mesenteroides* G6PDH showed enzyme-dependent formation of NADH and S-NADH peaks, which were confirmed by mass spectrometry (FIG. 10 and FIG. 11). These results suggest that the single atomic substitution within NR ribosyl ring has little effects on accepting electrons and S-NAD$^+$ can participate in redox reactions.

Figure 6:
FIG. 6: SDA-PAGE gel of the purified extracellular domain of human CD38.
Figures 15A, 15B, 15C, 15D:
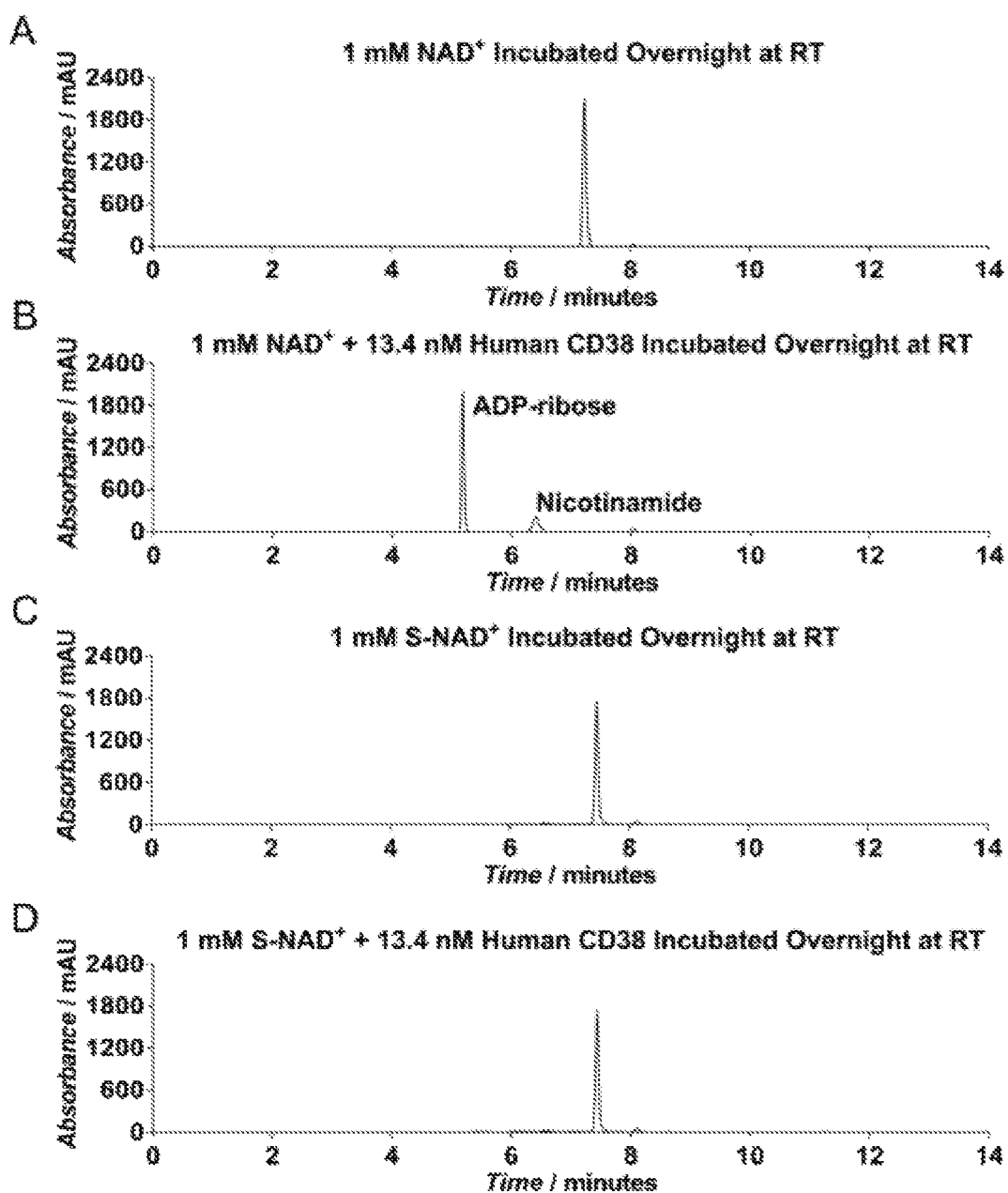
FIGS. 15A-15D: Activity of $NAD^+$ and $S-NAD^+$ for human CD38. HPLC analysis of substrate activities of $NAD^+$ (FIG. 15A-15B) and $S-NAD^+$ (FIG. 15C-15D) with human CD38 as measured by UV absorbance at 260 nm. 1 mM $NAD^+$ or $S-NAD^+$ was incubated without and with CD38 at RT overnight, followed by HPLC analysis.
Figure 16:
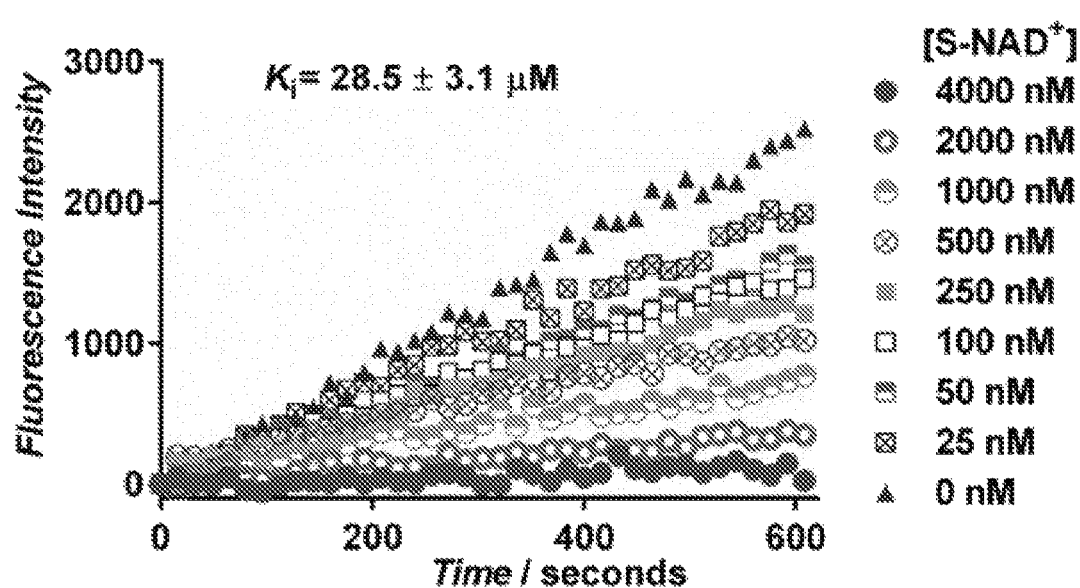
FIG. 16: Inhibition activity of $S-NAD^+$ for human CD38. Recombinant human CD38 (8 nM) was incubated with 50 µM $NGD^+$ in the presence of varied concentrations of $S-NAD^+$. CD38 cyclase activities were monitored on the basis of the formation of fluorescent cGDPR as measured at 410 nm.
Figures 17A, 17B, 17C:
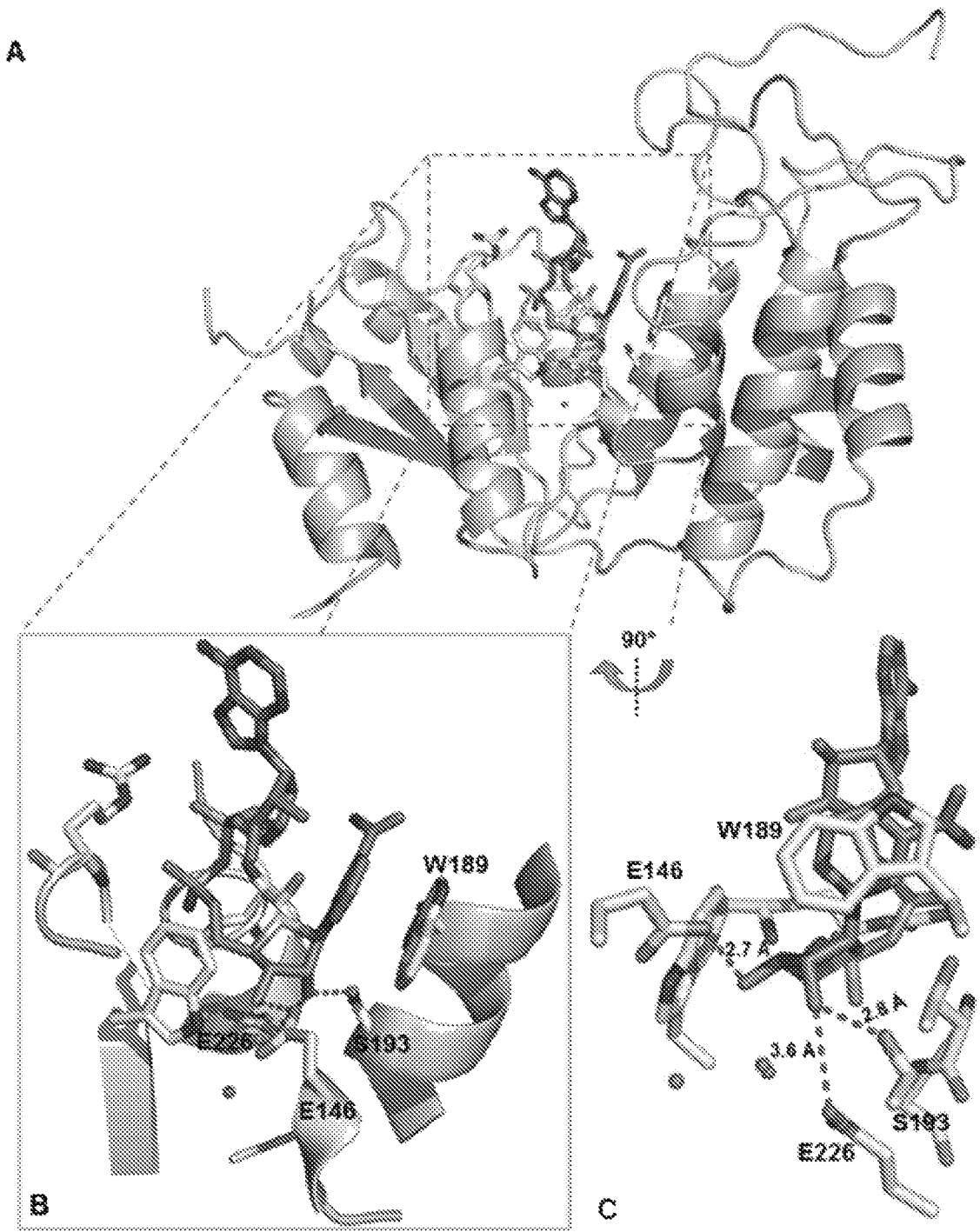
FIGS. 17A-17C: X-ray crystal structure of catalytically active human CD38 in complex with $S-NAD^+$. CD38 and $S-NAD^+$ are shown in grey and magenta, respectively.

To explore the binding mode of S-NAD$^+$ with human CD38, X-ray crystallographic analysis was carried out. The extracellular domain of wild-type human CD38 except four mutated glycosylation sites was recombinantly expressed in mammalian cells (FIG. 6). Enzymatic activities of purified CD38 were verified by fluorescence- and HPLC-based activity assays using NGD$^+$ and NAD$^+$ as substrates. Recombinant human CD38 in high purity was successfully cocrystallized with S-NAD$^+$ and its X-ray crystal structure was solved at a resolution of 2.4 Å (FIG. 15 and Table S2). The determined crystal structure clearly revealed the binding of S-NAD$^+$ to the active site of human CD38 and multiple interactions formed between S-NAD$^+$ and active site residues. The 4'-thioribose ring of S-NAD$^+$ adopted a C3'-endo-C2'-exo conformation. It was seen that the distances between S—NR 2'-OH of S-NAD$^+$ and side chains of S193 and E226 are 2.8 Å and 3.6 Å, respectively. The S—NR 3'-OH of S-NAD$^+$ is 2.7 Å away from the side chain of E146 (FIG. 15). These observations support that these three residues play important roles in catalysis of human CD38 and are consistent with previous reports, in which it was shown that E226 and S193 are catalytic residues involved in stabilization of formed oxacarbenium ion intermediate and E146 controls cyclizing and hydrolyzing activities.[22,31,53] The most striking finding for the determined X-ray structure is that the nicotinamide ring of S-NAD$^+$ is fully stacked on top of the indole ring of W189 (FIG. 15). The planes of S-NAD$^+$ nicotinamide and W189 indole are nearly parallel with an interplanar spacing of approximately 3.4 Å. On the basis of the solved X-ray structure, the relative position, orientation, and distance of the nicotinamide moiety of S-NAD$^+$ at the active site of human CD38 suggest that W189 plays an important role in activation of the leaving group upon binding of substrate. This finding is consistent with previous studies which showed that mutations of W189 cause significantly decreased enzymatic activities of human CD38. Taken together, the X-ray structure of S-NAD$^+$ with catalytically active human CD38 is consistent with the substrate and inhibition activities studies and demonstrates that as a stable mimic of NAD$^+$, the generated S-NAD$^+$ allows X-ray crystallographic characterization of reactive complexes of CD38 to elucidate its catalytic mechanism.

The methods of synthesis and compound testing herein may be further supplemented by those found in Zhang et al., *Nature Communications* volume 10, Article number: 4196 (2019), the entire disclosure of which is hereby incorporated by reference.

Conclusions

As a novel stable NAD$^+$ mimic, S-NAD$^+$ was successfully generated. By exploiting human NRK1 and NMNAT1, S-NAD$^+$ could be efficiently prepared from its chemically synthesized S—NR precursor through a two-step enzymatic process in a high yield. The generated S-NAD$^+$ is chemically inert to cleavage by human CD38, while functioning as an electron acceptor in redox reactions. The X-ray structure of S-NAD$^+$ with human CD38 demonstrates its binding to enzyme active site and revealed residues important for catalysis along the reaction coordinate. This work provides a facile and efficient chemoenzymatic approach for the generation of S-NAD$^+$ and a unique and important tool that can be extended to investigate NAD$^+$-dependent enzymes.

REFERENCES (1) Jeong, L. S.; Lee, H. W.; Jacobson, K. A.; Kim, H. O.; Shin, D. H.; Lee, J. A.; Gao, Z. G.; Lu, C.; Duong, H. T.; Gunaga, P.; Lee, S. K.; Jin, D. Z.; Chun, M. W.; Moon, H. R. Structure-activity relationships of 2-chloro-N6-substituted-4'-thioadenosine-5'-uronamides as highly potent and selective agonists at the human A3 adenosine receptor. *J. Med. Chem.* 2006, 49, 273.

(2) Khan, J. A.; Xiang, S.; Tong, L. Crystal structure of human nicotinamide riboside kinase. *Structure* 2007, 15, 1005.

(3) Raffaelli, N.; Sorci, L.; Amici, A.; Emanuelli, M.; Mazzola, F.; Magni, G. Identification of a novel human nicotinamide mononucleotide adenylyltransferase. *Biochemical and biophysical research communications* 2002, 297, 835.

(4) Preugschat, F.; Carter, L. H.; Boros, E. E.; Porter, D. J.; Stewart, E. L.; Shewchuk, L. M. A pre-steady state and steady state kinetic analysis of the N-ribosyl hydrolase activity of hCD157. *Archives of biochemistry and biophysics* 2014, 564, 156.

(5) Graeff, R. M.; Walseth, T. F.; Fryxell, K.; Branton, W. D.; Lee, H. C. Enzymatic synthesis and characterizations of cyclic GDP-ribose. A procedure for distinguishing enzymes with ADP-ribosyl cyclase activity. *Journal of Biological Chemistry* 1994, 269, 30260.

(6) Liu, Q.; Kriksunov, I. A.; Graeff, R.; Munshi, C.; Lee, H. C.; Hao, Q. Crystal structure of human CD38 extracellular domain. *Structure* 2005, 13, 1331.

(7) Liu, Q.; Kriksunov, I. A.; Graeff, R.; Munshi, C.; Lee, H. C.; Hao, Q. Structural basis for the mechanistic understanding of human CD38-controlled multiple catalysis. *Journal of Biological Chemistry* 2006, 281, 32861.

(8) Kabsch, W. Automatic processing of rotation diffraction data from crystals of initially unknown symmetry and cell constants. *Journal of applied crystallography* 1993, 26, 795.

(9) Winn, M. D.; Ballard, C. C.; Cowtan, K. D.; Dodson, E. J.; Emsley, P.; Evans, P. R.; Keegan, R. M.; Krissinel, E. B.; Leslie, A. G.; McCoy, A. Overview of the CCP4 suite and current developments. *Acta Crystallographica Section D: Biological Crystallography* 2011, 67, 235.

(10) Evans, P. Scaling and assessment of data quality. *Acta Crystallographica Section D. Biological Crystallography* 2006, 62, 72.

(11) McCoy, A. J.; Grosse-Kunstleve, R. W.; Adams, P. D.; Winn, M. D.; Storoni, L. C.; Read, R. J. Phaser crystallographic software. *Journal of applied crystallography* 2007, 40, 658.

(12) Langer, G.; Cohen, S. X.; Lamzin, V. S.; Perrakis, A. Automated macromolecular model building for X-ray crystallography using ARP/wARP version 7. *Nature protocols* 2008, 3, 1171.

(13) Murshudov, G. N.; Vagin, A. A.; Dodson, E. J. Refinement of macromolecular structures by the maximum-likelihood method. *Acta Crystallographica Section D: Biological Crystallography* 1997, 53, 240.

(14) Emsley, P.; Cowtan, K. Coot: model-building tools for molecular graphics. *Acta Crystallographica Section D: Biological Crystallography* 2004, 60, 2126.

(15) Moriarty, N. W.; Grosse-Kunstleve, R. W.; Adams, P. D. electronic Ligand Builder and Optimization Workbench (eLBOW): a tool for ligand coordinate and restraint generation. *Acta Crystallographica Section D: Biological Crystallography* 2009, 65, 1074.

(16) Adams, P. D.; Afonine, P. V.; Bunkoczi, G.; Chen, V. B.; Davis, I. W.; Echols, N.; Headd, J. J.; Hung, L.-W.; Kapral, G. J.; Grosse-Kunstleve, R. W. PHENIX: a comprehensive Python-based system for macromolecular structure solution. *Acta Crystallographica Section D: Biological Crystallography* 2010, 66, 213.

(17) Ryu, K. W.; Kim, D. S.; Kraus, W. L. New Facets in the Regulation of Gene Expression by ADP-Ribosylation and Poly(ADP-ribose) Polymerases. *Chem. Rev.* 2015.

(18) Lin, H. Nicotinamide adenine dinucleotide: beyond a redox coenzyme. *Org. Biomol. Chem.* 2007, 5, 2541.

(19) Imai, S.; Guarente, L. NAD+ and sirtuins in aging and disease. *Trends Cell Biol.* 2014, 24, 464.

(20) Verdin, E. NAD(+) in aging, metabolism, and neurodegeneration. *Science* 2015, 350, 1208.

(21) Yamamoto-Katayama, S.; Sato, A.; Ariyoshi, M.; Suyama, M.; Ishihara, K.; Hirano, T.; Nakamura, H.; Morikawa, K.; Jingami, H. Site-directed removal of N-glycosylation sites in BST-1/CD157: effects on molecular and functional heterogeneity. *Biochem. J.* 2001, 357, 385.

(22) Graeff, R.; Munshi, C.; Aarhus, R.; Johns, M.; Lee, H. C. A single residue at the active site of CD38 determines its NAD cyclizing and hydrolyzing activities. *J. Biol. Chem.* 2001, 276, 12169.

(23) Blacher, E.; Dadali, T.; Bespalko, A.; Haupenthal, V. J.; Grimm, M. O.; Hartmann, T.; Lund, F. E.; Stein, R.; Levy, A. Alzheimer's disease pathology is attenuated in a CD38-deficient mouse model. *Ann. Neurol.* 2015, 78, 88.

(24) Escande, C.; Nin, V.; Price, N. L.; Capellini, V.; Gomes, A. P.; Barbosa, M. T.; O'Neil, L.; White, T. A.; Sinclair, D. A.; Chini, E. N. Flavonoid apigenin is an inhibitor of the NAD+ ase CD38: implications for cellular NAD+ metabolism, protein acetylation, and treatment of metabolic syndrome. *Diabetes* 2013, 62, 1084.

(25) Tarrago, M. G.; Chini, C. C. S.; Kanamori, K. S.; Warner, G. M.; Caride, A.; de Oliveira, G. C.; Rud, M.; Samani, A.; Hein, K. Z.; Huang, R.; Jurk, D.; Cho, D. S.; Boslett, J. J.; Miller, J. D.; Zweier, J. L.; Passos, J. F.; Doles, J. D.; Becherer, D. J.; Chini, E. N. A Potent and Specific CD38 Inhibitor Ameliorates Age-Related Metabolic Dysfunction by Reversing Tissue NAD(+) Decline. *Cell metabolism* 2018, 27, 1081.

(26) Camacho-Pereira, J.; Tarrago, M. G.; Chini, C. C. S.; Nin, V.; Escande, C.; Warner, G. M.; Puranik, A. S.; Schoon, R. A.; Reid, J. M.; Galina, A.; Chini, E. N. CD38 Dictates Age-Related NAD Decline and Mitochondria) Dysfunction through an SIRT3-Dependent Mechanism. *Cell metabolism* 2016, 23, 1127.

(27) Blacher, E.; Ben Baruch, B.; Levy, A.; Geva, N.; Green, K. D.; Garneau-Tsodikova, S.; Fridman, M.; Stein, R. Inhibition of glioma progression by a newly discovered CD38 inhibitor. *Int. J. Cancer* 2015, 136, 1422.

(28) Morandi, F.; Horenstein, A. L.; Chillemi, A.; Quarona, V.; Chiesa, S.; Imperatori, A.; Zanellato, S.; Mortara, L.; Gattorno, M.; Pistoia, V.; Malavasi, F. CD56brightCD16− NK Cells Produce Adenosine through a CD38-Mediated Pathway and Act as Regulatory Cells Inhibiting Autologous $CD_4$+ T Cell Proliferation. *J. Immunol.* 2015, 195, 965.

(29) Chatterjee, S.; Daenthanasanmak, A.; Chakraborty, P.; Wyatt, M. W.; Dhar, P.; Selvam, S. P.; Fu, J.; Zhang, J.; Nguyen, H.; Kang, I.; Toth, K.; Al-Homrani, M.; Husain, M.; Beeson, G.; Ball, L.; Helke, K.; Husain, S.; Garrett-Mayer, E.; Hardiman, G.; Mehrotra, M.; Nishimura, M. I.; Beeson, C. C.; Bupp, M. G.; Wu, J.; Ogretmen, B.; Paulos, C. M.; Rathmell, J.; Yu, X. Z.; Mehrotra, S. CD38-NAD(+) Axis Regulates Immunotherapeutic Anti-Tumor T Cell Response. *Cell metabolism* 2018, 27, 85.

(30) Hassa, P. O.; Haenni, S. S.; Elser, M.; Hottiger, M. O. Nuclear ADP-ribosylation reactions in mammalian cells: where are we today and where are we going? *Microbiol. Mol. Biol. Rev.* 2006, 70, 789.

(31) Liu, Q.; Kriksunov, I. A.; Graeff, R.; Munshi, C.; Lee, H. C.; Hao, Q. Structural basis for the mechanistic understanding of human CD38-controlled multiple catalysis. *J. Biol. Chem.* 2006, 281, 32861.

(32) Liu, Q.; Kriksunov, I. A.; Graeff, R.; Lee, H. C.; Hao, Q. Structural basis for formation and hydrolysis of the calcium messenger cyclic ADP-ribose by human CD38. *J. Biol. Chem.* 2007, 282, 5853.

(33) Hoff, K. G.; Avalos, J. L.; Sens, K.; Wolberger, C. Insights into the sirtuin mechanism from ternary complexes containing NAD+ and acetylated peptide. *Structure* 2006, 14, 1231.

(34) Zatorski, A.; Watanabe, K. A.; Carr, S. F.; Goldstein, B. M.; Pankiewicz, K. W. Chemical synthesis of benzamide adenine dinucleotide: inhibition of inosine monophosphate dehydrogenase (types I and II). *J. Med. Chem.* 1996, 39, 2422.

(35) Langelier, M. F.; Zandarashvili, L.; Aguiar, P. M.; Black, B. E.; Pascal, J. M. NAD(+) analog reveals PARP-1 substrate-blocking mechanism and allosteric communication from catalytic center to DNA-binding domains. *Nature communications* 2018, 9, 844.

(36) Szczepankiewicz, B. G.; Dai, H.; Koppetsch, K. J.; Qian, D.; Jiang, F.; Mao, C.; Perni, R. B. Synthesis of carba-NAD and the structures of its ternary complexes with SIRT3 and SIRT5. *J. Org. Chem.* 2012, 77, 7319.

(37) Sauve, A. A.; Schramm, V. L. Mechanism-based inhibitors of CD38: a mammalian cyclic ADP-ribose synthetase. *Biochemistry* 2002, 41, 8455.

(38) Shrimp, J. H.; Hu, J.; Dong, M.; Wang, B. S.; Mac-Donald, R.; Jiang, H.; Hao, Q.; Yen, A.; Lin, H. Revealing

(39) Jiang, H.; Congleton, J.; Liu, Q.; Merchant, P.; Malavasi, F.; Lee, H. C.; Hao, Q.; Yen, A.; Lin, H. Mechanism-based small molecule probes for labeling CD38 on live cells. *J Am Chem Soc* 2009, 131, 1658.

(40) Sorci, L.; Cimadamore, F.; *Scotti, S.*; Petrelli, R.; Cappellacci, L.; Franchetti, P.; Orsomando, G.; Magni, G. Initial-rate kinetics of human NMN-adenylyltransferases: substrate and metal ion specificity, inhibition by products and multisubstrate analogues, and isozyme contributions to NAD+ biosynthesis. *Biochemistry* 2007, 46, 4912.

(41) Berger, F.; Lau, C.; Dahlmann, M.; Ziegler, M. Subcellular compartmentation and differential catalytic properties of the three human nicotinamide mononucleotide adenylyltransferase isoforms. *J. Biol. Chem.* 2005, 280, 36334.

(42) Tempel, W.; Rabeh, W. M.; Bogan, K. L.; Belenky, P.; Wojcik, M.; Seidle, H. F.; Nedyalkova, L.; Yang, T.; Sauve, A. A.; Park, H. W.; Brenner, C. Nicotinamide riboside kinase structures reveal new pathways to NAD+. *PLoS Biol* 2007, 5, e263.

(43) Jeong, L. S.; Lee, H. W.; Jacobson, K. A.; Kim, H. O.; Shin, D. H.; Lee, J. A.; Gao, Z.-G.; Lu, C.; Duong, H. T.; Gunaga, P. Structure—Activity Relationships of 2-Chloro-N 6-substituted-4-thioadenosine-5'-uronamides as Highly Potent and Selective Agonists at the Human A3 Adenosine Receptor. *Journal of medicinal chemistry* 2006, 49, 273.

(44) Yang, T.; Chan, N. Y.-K.; Sauve, A. A. Syntheses of nicotinamide riboside and derivatives: effective agents for increasing nicotinamide adenine dinucleotide concentrations in mammalian cells. *Journal of medicinal chemistry* 2007, 50, 6458.

(45) Dowden, J.; Moreau, C.; Brown, R. S.; Berridge, G.; Galione, A.; Potter, B. V. Chemical synthesis of the second messenger nicotinic acid adenine dinucleotide phosphate by total synthesis of nicotinamide adenine dinucleotide phosphate. *Angewandte Chemie* 2004, 116, 4737.

(46) Dowden, J.; Brown, R. S.; Moreau, C.; Galione, A.; Potter, B. V. Chemical synthesis of the novel Ca2+ messenger NAADP. *Nucleosides, Nucleotides and Nucleic Acids* 2005, 24, 513.

(47) Cen, Y.; Sauve, A. A. Transition state of ADP-ribosylation of acetyllysine catalyzed by *Archaeoglobus fulgidus* Sir2 determined by kinetic isotope effects and computational approaches. *Journal of the American Chemical Society* 2010, 132, 12286.

(48) Graeff, R. M.; Walseth, T. F.; Fryxell, K.; Branton, W. D.; Lee, H. C. Enzymatic synthesis and characterizations of cyclic GDP-ribose. A procedure for distinguishing enzymes with ADP-ribosyl cyclase activity. *J. Biol. Chem.* 1994, 269, 30260.

(49) Orsomando, G.; Polzonetti, V.; Natalini, P. NAD(P)(+)-glycohydrolase from human spleen: a multicatalytic enzyme. *Comp. Biochem. Physiol. B. Biochem. Mol. Biol.* 2000, 126, 89.

(50) Wall, K. A.; Klis, M.; Kornet, J.; Coyle, D.; Ame, J. C.; Jacobson, M. K.; Slama, J. T. Inhibition of the intrinsic NAD+ glycohydrolase activity of CD38 by carbocyclic NAD analogues. *Biochem. J.* 1998, 335 (Pt 3), 631.

(51) Li, M.; Smith, C. J.; Walker, M. T.; Smith, T. J. Novel inhibitors complexed with glutamate dehydrogenase: allosteric regulation by control of protein dynamics. *J. Biol. Chem.* 2009, 284, 22988.

(52) Olive, C.; Geroch, M. E.; Levy, H. R. Glucose 6-phosphate dehydrogenase from *Leuconostoc mesenteroides*. Kinetic studies. *J. Biol. Chem.* 1971, 246, 2047.

(53) Munshi, C.; Aarhus, R.; Graeff, R.; Walseth, T. F.; Levitt, D.; Lee, H. C. Identification of the enzymatic active site of CD38 by site-directed mutagenesis. *J. Biol. Chem.* 2000, 275, 21566.

(54) Liu, Q.; Kriksunov, I. A.; Graeff, R.; Munshi, C.; Lee, H. C.; Hao, Q. Crystal structure of human CD38 extracellular domain. *Structure* 2005, 13, 1331.

---

What is claimed is:

1. A method of synthesizing a compound of formula I:

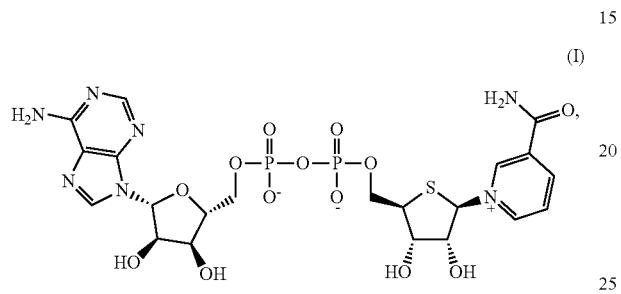

(I)

or a pharmaceutically acceptable salt or solvate thereof, comprising the step of enzymatically converting a compound of formula IV:

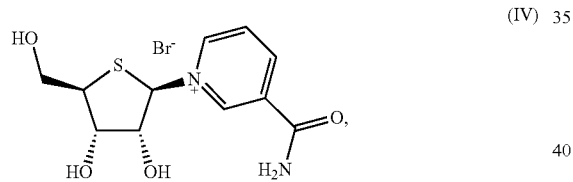

(IV)

to the compound of formula I.

2. The method of claim 1, wherein enzymatically converting the compound of formula IV to the compound of formula I comprises contacting the compound of formula IV with adenosine triphosphate (ATP), nicotinamide riboside kinase (NRK), and nicotinamide mononucleotide adenylyltransferase (NMNAT).

3. The method of claim 1, wherein the contacting is for less than 5 hours.

4. The method of claim 1, further comprising the step of converting a compound of formula II:

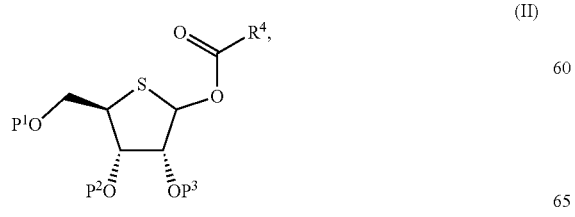

(II)

into a compound of formula III:

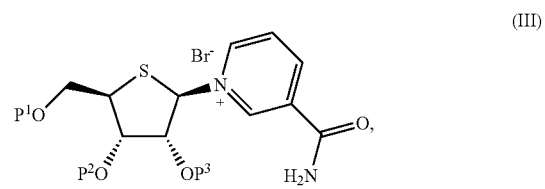

(III)

wherein $R^4$ is an optionally substituted $C_1$-$C_8$ alkyl;

$P^1$, $P^2$ and $P^3$ are protecting groups each independently selected from the group consisting of 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), benzyloxymethyl acetal (BOM), methoxymethyl acetal (MOM), methoxypropyl acetal (MOP), methyl ether, tetrahydropyranyl acetal (THP), triethylsilyl ether (TES), triisopropylsilyl ether (TIPS), trimethylsilyl ether (TMS), tert-Butyldimethylsilyl ether (TBS, TBDMS), and tert-butyldiphenylsilyl ether (TBDPS); or $P^2$ and $P^3$ together with the oxygens to which they are attached, together form an acetonide, benzaldehyde acetal or carbonate.

5. The method of claim 4, wherein $R^4$ is methyl.

6. The method of claim 4, wherein $P^1$ is Bz.

7. The method of claim 4, wherein $P^2$ and $P^3$ along with the oxygens to which they are attached, together form an acetonide.

8. The method of claim 4, further comprising the step of deprotecting the compound of formula III to produce the compound of formula IV.

9. The method of claim 8, wherein:

$P^1$ is Bz;

$P^2$ and $P^3$ along with the oxygens to which they are attached, together form an acetonide; and wherein deprotecting the compound of formula III to produce the compound of formula IV comprises contacting the compound of formula III with trifluoroacetic acid (TFA) to produce a compound of formula V:

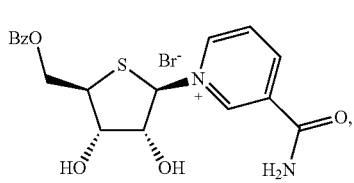

followed by deprotection of the compound of formula V to produce the compound of formula IV.

10. The method of claim 9, wherein deprotection of the compound of formula V to produce the compound of formula IV comprises contacting the compound of formula V with ammonia and methanol.

11. A method of inhibiting enzymatic activity of CD38, comprising contacting CD38 with a compound of formula I or pharmaceutically acceptable salts and solvates thereof:

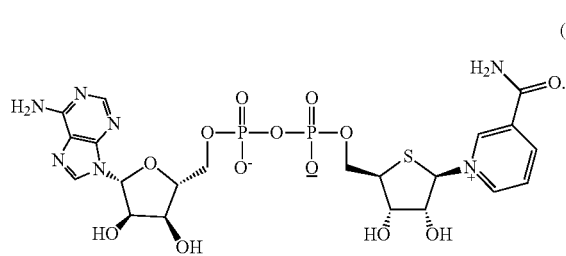

12. A compound of formula I-A and pharmaceutically acceptable salts and solvates thereof:

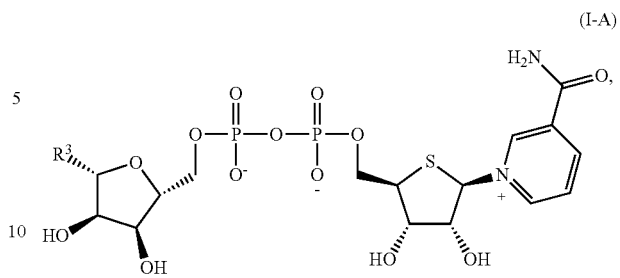

wherein $R^3$ is selected from thymine, cytosine, adenine, uracil or guanine.

13. The compound of claim 12, of formula I:

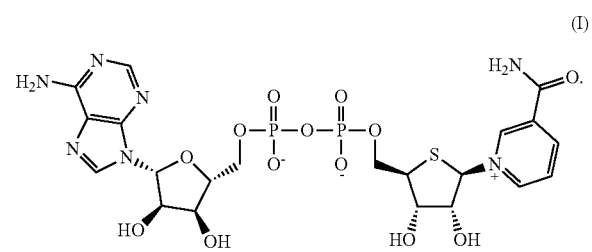

14. A pharmaceutical composition comprising a pharmaceutically effective amount the compound of claim 12 and a carrier.

15. A kit comprising the compound of claim 12 and instructions for use.

* * * * *

SEQUENCE LISTING

```
<160> NUMBER OF SEQ ID NOS: 10

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccatggatga aacatttat cattggaatc agtgg                              35

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcgagtgct gtcacttgca aacacttttg                                   30

<210> SEQ ID NO 3
```

```
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccatggatgc accaccacca ccaccacgaa aattccgaga agactgaagt g           51

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcgagctac tactatgtct tagcttctgc agtgtttc                          38

<210> SEQ ID NO 5
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Arg Phe Val Ile Gly Ile Gly Val Thr Asn Gly Gly Lys
1               5                   10                  15

Thr Thr Leu Ala Lys Ser Leu Gln Lys His Leu Pro Asn Cys Ser Val
            20                  25                  30

Ile Ser Gln Asp Asp Phe Phe Lys Pro Glu Ser Glu Ile Asp Ile Asp
        35                  40                  45

Glu Asn Gly Phe Leu Gln Tyr Asp Val Leu Glu Ala Leu Asn Met Glu
    50                  55                  60

Lys Met Met Ser Ala Val Ser Cys Trp Met Glu Asn Pro Gly Ser Ser
65                  70                  75                  80

Ala Gly Pro Ala Ala Leu Glu Ser Ala Gln Gly Val Pro Ile Leu Ile
                85                  90                  95

Ile Glu Gly Phe Leu Leu Phe Asn Tyr Lys Pro Leu Asp Thr Ile Trp
            100                 105                 110

Asn Arg Ser Tyr Phe Leu Thr Val Pro Tyr Glu Glu Cys Lys Arg Arg
        115                 120                 125

Arg Ser Thr Arg Val Tyr Glu Pro Pro Asp Pro Gly Tyr Phe Asp
    130                 135                 140

Gly His Val Trp Pro Met Tyr Leu Lys His Arg Gln Glu Met Ser Ser
145                 150                 155                 160

Ile Thr Trp Asp Ile Val Tyr Leu Asp Gly Thr Arg Ser Glu Asp
                165                 170                 175

Leu Phe Ser Gln Val Tyr Glu Asp Val Lys Gln Glu Leu Glu Lys Gln
            180                 185                 190

Asn Gly Leu His His His His His
        195                 200

<210> SEQ ID NO 6
<211> LENGTH: 285
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 6

```
Met Glu Asn Ser Glu Lys Thr Glu Val Leu Leu Ala Cys Gly Ser
1               5                   10                  15

Phe Asn Pro Ile Thr Asn Met His Leu Arg Leu Phe Glu Leu Ala Lys
                20                  25                  30

Asp Tyr Met Asn Gly Thr Gly Arg Tyr Thr Val Val Lys Gly Ile Ile
            35                  40                  45

Ser Pro Val Gly Asp Ala Tyr Lys Lys Gly Leu Ile Pro Ala Tyr
    50                  55                  60

His Arg Val Ile Met Ala Glu Leu Ala Thr Lys Asn Ser Lys Trp Val
65                  70                  75                  80

Glu Val Asp Thr Trp Glu Ser Leu Gln Lys Glu Trp Lys Glu Thr Leu
                85                  90                  95

Lys Val Leu Arg His His Gln Glu Lys Leu Glu Ala Ser Asp Cys Asp
                100                 105                 110

His Gln Gln Asn Ser Pro Thr Leu Glu Arg Pro Gly Arg Lys Arg Lys
            115                 120                 125

Trp Thr Glu Thr Gln Asp Ser Ser Gln Lys Lys Ser Leu Glu Pro Lys
130                 135                 140

Thr Lys Ala Val Pro Lys Val Lys Leu Leu Cys Gly Ala Asp Leu Leu
145                 150                 155                 160

Glu Ser Phe Ala Val Pro Asn Leu Trp Lys Ser Glu Asp Ile Thr Gln
                165                 170                 175

Ile Val Ala Asn Tyr Gly Leu Ile Cys Val Thr Arg Ala Gly Asn Asp
            180                 185                 190

Ala Gln Lys Phe Ile Tyr Glu Ser Asp Val Leu Trp Lys His Arg Ser
        195                 200                 205

Asn Ile His Val Val Asn Glu Trp Ile Ala Asn Asp Ile Ser Ser Thr
    210                 215                 220

Lys Ile Arg Arg Ala Leu Arg Arg Gly Gln Ser Ile Arg Tyr Leu Val
225                 230                 235                 240

Pro Asp Leu Val Gln Glu Tyr Ile Glu Lys His Asn Leu Tyr Ser Ser
                245                 250                 255

Glu Ser Glu Asp Arg Asn Ala Gly Val Ile Leu Ala Pro Leu Gln Arg
            260                 265                 270

Asn Thr Ala Glu Ala Lys Thr His His His His His
        275                 280                 285
```

<210> SEQ ID NO 7
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His Pro Glu
                20                  25                  30

Met Arg His Val Asp Cys Gln Ser Val Trp Asp Ala Phe Lys Gly Ala
            35                  40                  45
```

```
Phe Ile Ser Lys His Pro Cys Asp Ile Thr Glu Glu Asp Tyr Gln Pro
 50                  55                  60

Leu Met Lys Leu Gly Thr Gln Thr Val Pro Cys Asn Lys Ile Leu Leu
 65                  70                  75                  80

Trp Ser Arg Ile Lys Asp Leu Ala His Gln Phe Thr Gln Val Gln Arg
                 85                  90                  95

Asp Met Phe Thr Leu Glu Asp Thr Leu Leu Gly Tyr Leu Ala Asp Asp
                100                 105                 110

Leu Thr Trp Cys Gly Glu Phe Ala Thr Ser Lys Ile Asn Tyr Gln Ser
            115                 120                 125

Cys Pro Asp Trp Arg Lys Asp Cys Ser Asn Asn Pro Val Ser Val Phe
130                 135                 140

Trp Lys Thr Val Ser Arg Arg Phe Ala Glu Ala Ala Cys Asp Val Val
145                 150                 155                 160

His Val Met Leu Asp Gly Ser Arg Ser Lys Ile Phe Asp Lys Asp Ser
                165                 170                 175

Thr Phe Gly Ser Val Glu Val His Asn Leu Gln Pro Glu Lys Val Gln
                180                 185                 190

Thr Leu Glu Ala Trp Val Ile His Gly Gly Arg Glu Asp Ser Arg Asp
            195                 200                 205

Leu Cys Gln Asp Pro Thr Ile Lys Glu Leu Glu Ser Ile Ile Ser Lys
210                 215                 220

Arg Asn Ile Gln Phe Ser Cys Lys Asn Ile Tyr Arg Pro Asp Lys Phe
225                 230                 235                 240

Leu Gln Cys Val Lys Asn Pro Glu Asp Ser Ser Cys Thr Ser Glu Ile
                245                 250                 255

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agtcttgcac ttgtcacgaa ttcgcatcat cac                                33

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgtctggcc agctagcact tatcag                                       26

<210> SEQ ID NO 10
<211> LENGTH: 6
<212> TYPE: PRT
<213> ORGANISM: Artificial Sequence
```

-continued

```
<220> FEATURE:
<223> OTHER INFORMATION: Description of Artificial Sequence: Synthetic
      6xHis tag

<400> SEQUENCE: 10

His His His His His His
1               5
```